US008318094B1

(12) United States Patent
Bayandorian et al.

(10) Patent No.: US 8,318,094 B1
(45) Date of Patent: Nov. 27, 2012

(54) SUBSTRATE ANALYSIS SYSTEMS

(75) Inventors: Hovig Bayandorian, Berkeley, CA (US); Yujuan Cheng, Foster City, CA (US); John Dixon, Moss Beach, CA (US); Kevin Hester, Belmont, CA (US); Yanqiao Huang, San Mateo, CA (US); Paul Lundquist, San Francisco, CA (US); Joy Roy, San Jose, CA (US); Stephen Turner, Menlo Park, CA (US); Peiqian Zhao, Mountain View, CA (US); Cheng Frank Zhong, Fremont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 13/162,433

(22) Filed: Jun. 16, 2011

Related U.S. Application Data

(60) Provisional application No. 61/397,948, filed on Jun. 18, 2010.

(51) Int. Cl.
*G01N 31/00* (2006.01)
(52) U.S. Cl. ............ 422/63; 422/62; 422/67; 422/68.1; 422/82.05; 422/400; 436/43; 436/164
(58) Field of Classification Search ............... 422/62–63, 422/67, 68.1, 50, 82.05–82.09, 400; 436/43, 436/164
See application file for complete search history.

(56) References Cited

U.S. PATENT DOCUMENTS

| | | | | |
|---|---|---|---|---|
| 5,125,748 A * | 6/1992 | Bjornson et al. | ............... | 356/414 |
| 6,255,083 B1 | 7/2001 | Williams | | |
| 6,556,923 B2 * | 4/2003 | Gallagher et al. | ............... | 702/23 |
| 6,652,015 B1 * | 11/2003 | Carney et al. | ................ | 294/86.4 |
| 6,787,308 B2 | 9/2004 | Balasubramanian | | |
| 6,917,726 B2 | 7/2005 | Levene | | |
| 7,056,661 B2 | 6/2006 | Korlach | | |
| 7,170,050 B2 | 1/2007 | Turner et al. | | |
| 7,316,801 B2 * | 1/2008 | Kercso et al. | .................... | 422/65 |
| 7,352,889 B2 * | 4/2008 | Ganz et al. | .................... | 382/141 |
| 8,021,611 B2 * | 9/2011 | Roach et al. | .................... | 422/63 |
| 8,222,048 B2 * | 7/2012 | Fritchie et al. | ................ | 436/526 |
| 2003/0045000 A1 * | 3/2003 | Frank et al. | .................... | 436/180 |
| 2003/0215862 A1 | 11/2003 | Parce | | |
| 2005/0232821 A1 * | 10/2005 | Carrillo et al. | ................ | 422/100 |
| 2009/0068062 A1 * | 3/2009 | Jafari et al. | ...................... | 422/64 |
| 2009/0180931 A1 * | 7/2009 | Silbert et al. | .................... | 422/63 |
| 2009/0285719 A1 * | 11/2009 | Hirano et al. | ................. | 422/68.1 |
| 2011/0256630 A1 * | 10/2011 | Clinton | .......................... | 436/48 |

FOREIGN PATENT DOCUMENTS

| | | |
|---|---|---|
| WO | 91/06678 A1 | 5/1991 |
| WO | 96/27025 A1 | 9/1996 |
| WO | 99/05315 A2 | 2/1999 |

OTHER PUBLICATIONS

Eid et al, "Real-time DNA sequencing from single polymerase molecules" Science (2009) 323(5910):133-138.
Levene et al., "Zero-mode waveguides for single molecule analysis at high concentrations" Science (2003) 299:682-686.

* cited by examiner

*Primary Examiner* — Brian R Gordon
(74) *Attorney, Agent, or Firm* — Robert H. Reamey

(57) ABSTRACT

This invention provides systems for analyzing substrates. Also provided by the invention are improved optical systems for enhanced multiplex illumination, optical systems with compact multi-wavelength illumination architectures, optical systems for enhanced detection of optical signals, and optical systems for reduced autofluorescence background noise.

15 Claims, 61 Drawing Sheets

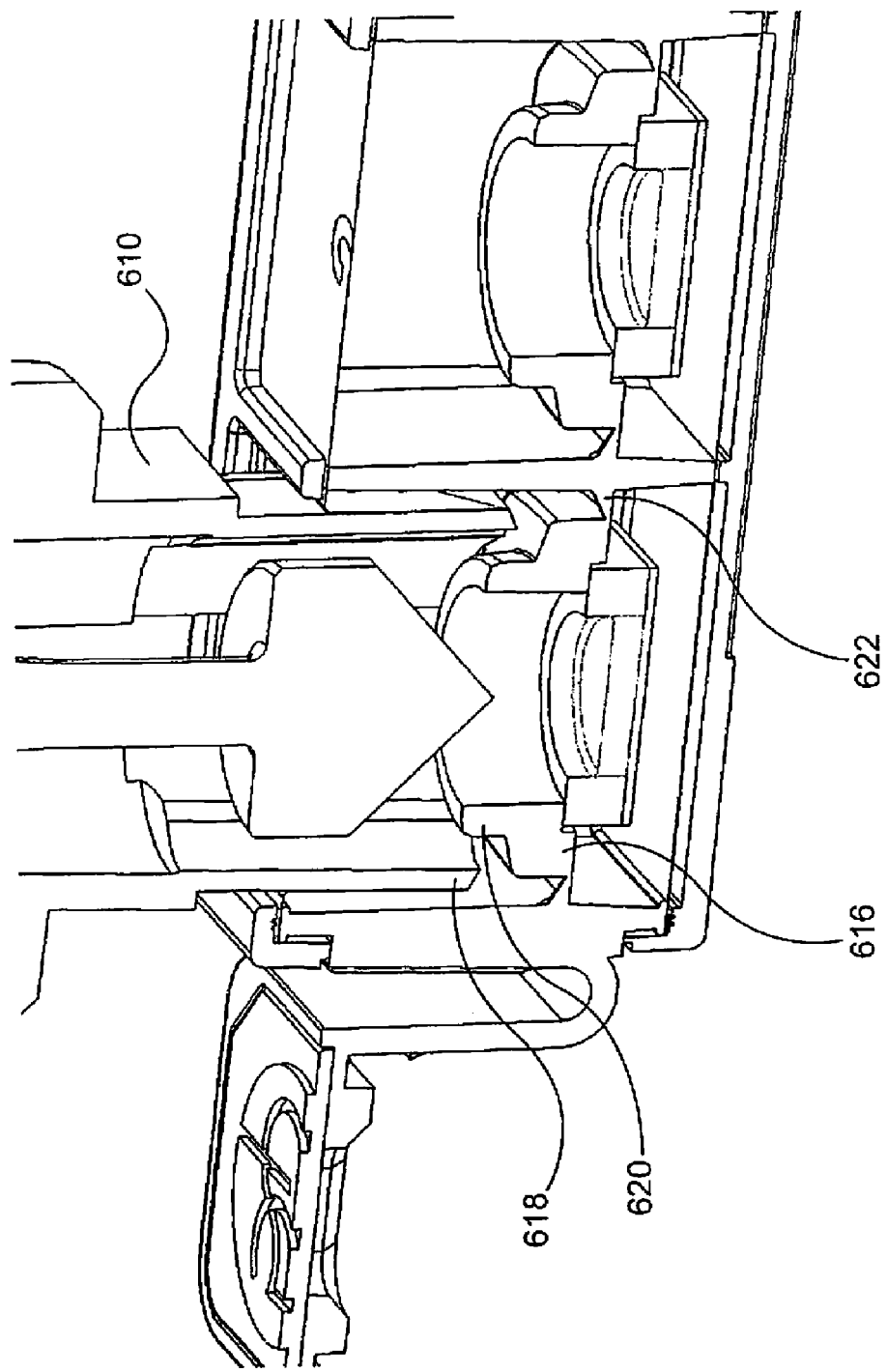

SUBSTRATE ANALYSIS SYSTEMS

CROSS REFERENCE TO RELATED APPLICATIONS

This application claims priority to Provisional U.S. Patent Application No. 61/397,948, filed Jun. 18, 2010, the full disclosure of which is hereby incorporated herein by reference in its entirety for all purposes.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

The individual identification, distinction and/or quantitation of different optical signals from a collection of such signals is of major importance in a number of different fields. Of particular note is the use of multiplexed analytical operations, e.g., nucleic acid analysis, biological assays, chemical assays, etc., which rely on optical signaling.

A variety of automated laboratory systems are available and have been described in the literature. For an introduction to the topic, see, e.g, Inglese (Editor) (2006) *Methods in Enzymology, Volume* 414: *Measuring Biological Responses with Automated Microscopy* Academic Press; $1^{st}$ edition ISBN-10: 0121828190; Haney (Editor) (2008) *High Content Screening: Science, Techniques and Applications* Wiley-Interscience ISBN-10: 047003999X; Janzen and Bernasconi (Editors) (2009) *High Throughput Screening: Methods and Protocols (Methods in Molecular Biology)* Humana Press; $2^{nd}$ ed. edition, ISBN-10: 1603272577; and Clemons, Tolliday and Wagner (Editors) (2009) *Cell-Based Assays for High-Throughput Screening: Methods and Protocols (Methods in Molecular Biology)* ISBN-10: 1603275444.

Useful analytical assays include nucleic aid sequencing, e.g., whole genome sequencing, medical diagnostic tests, food and other industrial process analyses, and basic tools of biological research and development. For example, a variety of commercial nucleic acid sequencing systems are available. These include traditional Sanger capillary sequencing instruments such as the 3500 and 3500xl systems from Applied Biosystems, the SOLiD Sequencer from Life Technologies, automated pyrosequencing systems such as the Genome Sequencer FLX instrument from 454 Life Sciences (Roche), and many others.

While a wide variety of optical and chemical approaches have been applied toward analysis of optical signals, such systems often include a level of complexity and/or cost that detracts from the overall utility of the approach, particularly for operations that require high levels of sensitivity. The present invention addresses these shortcomings.

SUMMARY OF THE INVENTION

Substrate analysis systems of the invention find use in various applications, e.g., for analyte analysis, monitoring of enzymatic reactions, such as nucleic acid and polypeptide polymerization reactions, detecting binding and other intermolecular interactions, genotyping, and many others. The systems are particularly suitable for detecting, monitoring, and analyzing single molecules, molecular complexes, or intermolecular reactions. As opposed to technologies that allow only bulk detection, the ability to detect individual molecules and reactions facilitates analyses that are not possible with bulk detection, e.g., measurements of kinetics of an individual enzyme or enzyme complex in real time. For example, single polymerase or ribosome complexes can be monitored during polymerization of nucleic acids or polypeptides, respectively.

In one aspect, the invention provides substrate analysis systems that include one or more substrate preparation station(s) configured to deliver one or more reactant(s) to at least one reaction site on at least one substrate, a substrate analysis mount configured to accept at least one substrate, a substrate transporter that transports the substrate between the substrate preparation station and the substrate analysis mount, and at least one optical train configured to illuminate the substrate and to receive optical signals from the substrate, wherein the system is capable of illuminating different portions of the substrate at different times, e.g., through controllable patterned illumination, or movement of one or more of the stage, chip or chip mount and optical train relative to each other. The substrate preparation station(s) optionally includes an automatic pipetting station, or a thermal controller that controls a temperature of the substrate when present in the station, or both. The substrate preparation station(s) can include a pipettor station that loads reactants onto the substrate, and an incubation station where the substrate with loaded reactants is incubated at a selected temperature prior to being transported to the substrate analysis mount, or afterwards, or both. Optionally, the substrate transporter of the analysis system includes an automated gripper configured to grasp the substrate.

Analysis systems of the invention optionally include a substrate container storage tray, where the automated gripper is configured to puncture a seal on a substrate container mounted in the storage tray and to grasp the substrate inside of the container. During operation of the system, the gripper removes the substrate from the container and delivers it to the substrate preparation station. The substrate can include one or more detents that mate with corresponding grasping features (e.g., a "tooth" or one or more "teeth") of the gripper when the gripper grasps the substrate. The gripper can be configured to move the substrate from the sample preparation station to the substrate analysis mount.

Substrates that find use in the analysis systems typically include one or more regions wherein an analytic reaction takes place. An example reaction region that can be disposed upon or within a substrate of the invention is a zero-mode waveguide. In one aspect, the substrates can include one or more zero-mode waveguides, e.g., a plurality of zero-mode waveguides (e.g., about 80,000 or more zero-mode waveguides).

Optionally, the temperature of one or more components of the analysis systems of the invention is controlled, e.g., the substrate analysis mount and/or the optical train can be operably coupled to one or more low-vibration cooling structure. For example, the optical train can include one or more fluid cooling structures and/or the substrate analysis mount can include or is coupled proximal to at least one heat sink or Peltier cooling structure. In a related aspect, the substrate analysis mount or the optical train optionally includes one or more leveling or vibration damping components.

Analysis systems of the invention include an optical system that includes one or more optical excitation sources (e.g., two, three or more optical excitation sources) for providing excitation radiation to the substrate in the mount. In one aspect, a mirror (e.g., a fluorescence transmissive or fluorescence reflective mirror) directs the excitation radiation from the optical excitation source to the substrate. For applications where it is desirable to provide two or more beams of excitation radiation to the substrate (e.g., where each beam is dedicated to illuminating one of a plurality of reaction regions on the substrate), the optical train can include a diffractive optical element that splits a co-directed beam of excitation radiation from the one or more optical excitation source into two or more beamlets of excitation radiation. The mirror described above can be configured to direct the two or more beamlets of excitation radiation to two or more reaction regions on the substrate.

Optical trains of the invention optionally include one or more signal detectors that detect optical signals reflected from a surface of the substrate and/or emanating from reaction regions on or in the substrate. The one or more signal detectors can be any suitable detector for detecting optical signals, e.g., one or more complementary metal oxide semiconductor (CMOS) detectors. In one embodiment, the analysis system includes one or more mirror (e.g., three mirrors) that directs the optical signals emanating from the reaction regions to the one or more signal detectors (e.g., four signal detectors), the one or more mirror being reflective for optical signals within a spectral range and transmissive for optical signals not within the spectral range. One or more optical filters can be positioned between the one or more mirror and the one or more signal detector. Optionally, an objective is disposed within an optical path between the substrate and the one or more optical excitation source and/or the one or more signal detectors.

The invention also provides improved focusing, leveling, and alignment modules for enhanced substrate illumination and/or detection of optical signals emanating from the substrate. In one aspect, substrate analysis systems of the invention include one or more optical detector that detects optical signals reflected from a surface of the substrate and/or emanating from reaction regions on or in the substrate, and an autofocus module that determines the distance between two surfaces of the substrate and aligns the substrate to the focal plane of the one or more signal detector. The autofocus module optionally includes a position sensitive detector (PSD) that detects optical energy emanating from the substrate and through the objective. The objective can be disposed at a first position such that optical energy emanating from the optical energy source reflects off a first surface of the substrate, back through the objective and onto the PSD to provide z position information for the first surface of the substrate. During operation of the system, the objective is moved to a second position such that optical energy emanating from the optical energy source reflects off a second surface of the substrate, back through the objective and onto the position sensitive detector to provide z position information for the second surface of the substrate, such that the difference between the z positions for the first and second surfaces of the substrate is utilized to determine the distance between the first and second surfaces of the substrate.

Also provided is an alignment module for aligning an optical axis of the objective with an optical path of the optical energy passing through the objective, where the alignment module aligns the optical axis of the objective to a reference plane attached to a mounting of the objective such that the optical energy passing through the objective is perpendicular to the reference plane and parallel to the objective optical axis. The alignment module optionally includes a source of optical energy configured to direct an incident beam of optical energy toward a surface of the objective, and an interference detector that detects a pattern of interference between the incident beam and back reflected wavefronts from the objective, where the alignment module positions the objective such that the back reflected wavefronts are axially symmetric about the incident beam.

In another aspect of the invention, the analysis system includes an autofocus and/or alignment module that captures fscore values of detected images resulting from optical signals emanating from reaction regions on or in the substrate, where the module utilizes the fscore values to determine an optimal z focus position and correction collar setting for the optical train.

In still other aspects, the invention provides analysis systems that include a mask disposed between the substrate and the one or more optical detectors, which mask prevents detection by the one or more optical detectors of out-of-focus light emanating from the substrate. Optionally, the one or more optical detectors detect optical energy emanating from fiducial marks disposed on the substrate in a detectable area between an outer edge of the mask and an outer edge of the field of view of the one or more optical detectors. The fiducial marks facilitate alignment of reaction regions on the substrate with the optical train.

The invention also provides systems that include one or more lenses in an illumination path and/or a collection path of the optical train, the one or more lens compensating for variation of the focal length of the objective to maintain constant magnification within the optical train. In a related aspect, one or more tube lens are disposed in an illumination path and/or a collection path of the optical train, such that the front focal plane of the one or more tube lens coincides with the back focal plane of the objective. Optionally, a parallel glass plate can be disposed between the objective and the tube lens to achieve a magnification equal to the focal length ratio of the tube lens and the objective.

In another aspect, compact illumination architectures are provided. For example, the substrate analysis system optionally includes two or more sources of excitation radiation and a prism that combines excitation radiation emanating from the two or more sources of excitation radiation into a collinear beam of excitation radiation.

Also provided is a substrate analysis system that includes a reflective mirror group disposed between the mirror and the substrate, the reflective mirror group configured to establish an indirect illumination path between the mirror and the substrate, and a refractive lens group disposed in a collection path of the optical train between the mirror and the one or more signal detector, the refractive lens group configured to correct for high order aberrations in the optical train.

Analysis systems where transmission illumination is used to illuminate reaction regions on the substrate are also provided. In one embodiment, the analysis system includes a transmission illumination and detection subsystem that detects optical signals emanating from one or more reaction regions on or in the substrate. Optionally, the transmission illumination and detection subsystem includes one or more source(s) of transmission excitation radiation that directs excitation radiation toward the substrate, and one or more signal detector(s) that detects optical signals emanating from one or more reaction region (e.g., one or more zero-mode waveguide) on the substrate, where the one or more source(s) of excitation radiation and the one or more signal detector(s) are disposed on opposite sides relative to the substrate. In this aspect, an objective can be disposed in a collection path between the substrate and the one or more signal detector.

In yet another aspect, the substrate analysis system includes a module for determining positional information of the substrate about more than one axis. The module can include a dichroic mirror, a camera or one or more position sensitive detectors (PSDs); one or more laser source that directs laser light energy at the substrate, and one or more transmitted light source that directs transmitted light at the substrate. Laser light energy and transmitted light reflected off the substrate, and through the objective, is reflected off the dichroic mirror and directed toward the camera or one or more PSDs, such that the position of the reflected light on the camera or one or more PSDs facilitates determination of the positional information of the substrate about the more than one axis.

The invention also provides analysis systems that include a source of transmission illumination optical energy, a substrate comprising an opaque layer disposed upon or within a first portion of the substrate, where optically detectable features are disposed through the opaque layer of the substrate, which optically detectable features are transmissive to optical energy emanating from the source of transmission illumination optical energy. This particular system also includes a mask that includes an opaque layer disposed upon or within a first portion of the mask, where optically detectable features are disposed through the opaque layer of the mask, which optically detectable features are transmissive to optical energy emanating from the source of transmission illumination optical energy. Also provided in this aspect is one or more optical detectors configured to detect optical energy emanating from the source of transmission illumination optical energy and through the optically detectable features of the substrate and mask, and an alignment module that aligns the substrate and mask by comparing the relative position and/or orientation of images derived from the optically detectable features of the substrate and mask, which images are captured by the one or more optical detectors. Optionally, this aspect of the invention includes a transillumination mask disposed between the source of transmission illumination optical energy and the substrate, the transillumination mask preventing transmission illumination optical energy from illuminating analytic reaction regions of the substrate.

In another aspect, systems of the invention include an autofocus and/or substrate leveling module that aligns the substrate to the focal plane of the one or more signal detector. Optionally, the autofocus and/or substrate leveling module includes a beam expander that expands a beam of optical energy emanating from the one or more optical excitation source, and a polarized beam splitter that divides the expanded beam of optical energy into two or more Z-focus beams and one or more substrate leveling beam. This particular system can further include a pinhole grating that converts the two or more z-focus beams into two smaller beams, a mirror that directs the two smaller beams through one or more beam splitters, an objective that optically couples the two smaller beams with a reflective surface of the substrate, a first polarizer that polarizes the z-focus beams reflected from the reflective surface of the substrate, and a lens that optically couples the polarized z-focus beams to the one or more signal detector. The polarized z-focus beams optionally pass through a second polarizer positioned between the lens and the one or more signal detector. The system can further include a beam splitter through which the one or more substrate leveling beam passes, a mirror that directs the one or more substrate leveling beam through a polarized beam splitter, an objective through which the leveling beam passes as the leveling beam travels toward or reflects from the substrate, a lens that optically couples the one or more leveling beam to the one or more signal detector. The one or more leveling beam optionally passes through a second polarizer positioned between the lens and the one or more signal detector. The substrate optionally includes a microlens array that reflects two or more z-focus beams and/or one or more substrate leveling beam.

Systems with substrate drift tracking modules are also provided. An example system includes an optical energy source that directs optical energy toward the substrate, and one or more optical energy detector that detect optical energy emanating from the optical energy source, where the optical energy source and the one or more optical energy detector are disposed on opposite sides relative to the substrate. Here, the detection of optical energy emanating from the optical energy source and/or the substrate provides information relating to drift in the position of the substrate. Optionally, the optical energy source intermittently directs optical energy toward the substrate and the one or more optical energy detector detects the intermittent optical energy emanating from the optical energy and/or the substrate. The drift tracking module can include an image algorithm that utilizes data from the one or more optical energy detector to determine the presence or absence of drift in the position of the substrate, where the drift tracking module is configured to align the optical train and/or substrate when the module determines the presence of drift in the position of the substrate.

In yet another aspect, systems of the invention can include an alignment module that aligns two or more beamlets of excitation radiation with two or more reaction regions on the substrate. One or more micromirror are optionally disposed proximal to each of the two or more reaction regions on the substrate. The alignment module can include an optical energy source that directs optical energy toward the substrate, and an optical energy detector configured to detect optical energy reflected from the one or more micromirror disposed proximal to each of the two or more reaction regions of the substrate. The alignment module can include a lens through which optical energy reflected from the one or more micromirror passes prior to reaching the optical energy detector, which detector can be configured to detect the positions of the two or more beamlets of excitation radiation on the substrate. The alignment module optionally compares the position on the detector of the detected optical energy reflected from the one or more micromirror and the positions of the two or more beamlets of excitation radiation on the substrate to align the two or more beamlets with the two or more reaction regions.

In a related aspect, systems of the invention include an alignment module that includes an objective that transmits and/or refracts optical energy traveling toward and reflecting from the substrate, where a portion of the optical energy is targeted to one or more non-reaction region features of the substrate. Also included is one or more optical detector configured to detect optical energy reflected from the one or more non-reaction region features of the substrate, as well as a pickoff window that directs optical energy reflected from the one or more non-reaction region features of the substrate toward the one or more optical detector. Optionally, a tube lens that optically couples optical energy traveling from the pickoff window toward the optical detector is provided. According to this aspect of the invention, the intensity of the optical energy reflected from the one or more non-reaction region features of the substrate, as detected by the optical detector, is indicative of the alignment between the two or more beamlets of excitation radiation and the two or more reaction regions on the substrate. The one or more non-reaction region features of the substrate optionally include one or more diffraction features (e.g., one or more micromirrors), such that an angular shift on the optical detector of the optical energy reflected from the one or more diffraction features is indicative of the alignment between the two or more beamlets of excitation radiation and the two or more reaction regions on the substrate.

Analysis systems of the invention can also include autofocus modules that include an optical energy source, an optical element that blocks a portion of a beam of optical energy emanating from the optical energy source, an objective lens configured to focus optical energy not blocked by the optical element onto a surface of the substrate, which focused optical energy is reflected off the surface of the substrate, and an optical detector that detects the optical energy reflected off the surface of the substrate. Optionally, the module includes a dichroic mirror that directs the optical energy reflected off the surface of the substrate toward the optical detector, which mirror is optionally coupled to the optical detector via a lens.

In another aspect, systems of the invention include an optical train that provides a plurality of excitation radiation beamlets to the substrate at a first pitch, where an array of reaction regions is disposed upon or within the substrate at a second pitch that is less than the first pitch (e.g., the second pitch can be about one half as compared to the first pitch). Optionally, the plurality of excitation radiation beamlets are positioned to illuminate a first group of reaction regions within the array of reaction regions, and then subsequently repositioned to illuminate a second group of reaction regions within the array of reaction regions.

Also provided are analysis systems that include a substrate leveling module that aligns the substrate to the focal plane of the one or more signal detector, the leveling module including a translatable and/or rotatable substrate mount (e.g., a hexapod stage as described in detail below). The substrate leveling module is optionally configured to translate the substrate mount to two or more z locations, where the one or more signal detector acquires one or more image of the substrate at the two or more z locations, and where the substrate leveling module calculates focal scores for one or more blocks within the one or more image at the two or more z locations. According to this aspect of the invention, the substrate leveling module can effectuate the translatable and/or rotatable substrate mount based on the focal scores at the two or more z locations to align the substrate to the focal plane of the one or more signal detector.

In a further aspect, systems of the invention can include an output that delivers optical signal data from the optical train to a signal analysis module. Optionally included in the system are one or more camera or CCD coupled to the signal analysis module, which signal analysis module provides a virtual focus feature that filters signals received by the camera or CCD.

Also provided are systems that include at least one environmental control module that controls one or more environmental parameters of the substrate preparation station(s), the analysis mount, the optical train, the cabinet, and the like. The substrate preparation station(s), the substrate mount and the substrate transporter are optionally housed in an upper portion of a cabinet, with the optical train being housed in a lower portion of the cabinet. The environmental control system controls pressure or humidity in the upper or lower portion of the cabinet. Optionally, the system includes a machine vision subsystem that monitors aspects of the system such as substrate transport, substrate positioning, transporter position, transporter movement, activity of the substrate preparation station, and the like. A user interface that accepts user instructions to control one or more feature of the system is optionally provided. Optionally, the substrate preparation system delivers nucleic acid sequencing reagents, the substrates comprise one or more zero mode waveguides in which sequencing reactions are performed and the system detects signals from the substrate when mounted in the substrate mount that can be converted to provide nucleic acid sequencing information. Systems of the invention can also include instructions that direct movement of the substrate during operation of the device, such that a sequencing or other reaction in or on the substrate is partly performed in the analysis mount, the substrate is moved to an incubation station, where the reaction proceeds further, and the substrate is moved back to the analysis mount, where the reaction again proceeds further.

In yet another aspect, high-throughput substrate analysis systems are provided. Such systems can include a substrate container storage tray configured to accept a plurality of substrate containers, a substrate preparation station configured to deliver one or more reactant to at least one reaction site on at least one substrate, an automated gripper configured to puncture a seal on a substrate container mounted in the storage tray, and to grasp the substrate inside of the container, such that during operation of the system, the gripper removes the substrate from the container and delivers it to the substrate preparation station. An optional incubation station that incubates the substrate is provided, where the automated gripper moves the substrate from the substrate preparation station to the incubation station. The high-throughput substrate analysis systems further include an analysis mount configured to accept at least one substrate from the substrate preparation station or the incubation station for analysis, an environmental control module that controls one or more environmental parameters of the substrate preparation station, incubation station, or the analysis mount, and a machine vision system for monitoring one or more of substrate transport, substrate positioning, gripper position, gripper movement, or activity of the substrate preparation station, the incubation station, or the analysis mount. Also included in the system is an optical train configured to illuminate the substrate in the substrate mount and to receive optical signals from the substrate, the substrate holder or the optical train being adjustable relative to one another. In addition, included is an autofocus module configured to monitor the quality of optical signal detection and adjust the relative positions of the substrate and one or more components of the optical train to enhance detection of optical signals from the substrate, an output that delivers optical signal data from the optical train to an analysis module, at least one low vibration cooling element that cools the substrate when mounted in the substrate mount, or that cools the substrate mount, or that cools the optical train, or a combination thereof and a user interface that accepts user instructions to control the substrate preparation station, gripper, analysis mount, environmental control module, or low vibration cooling element.

The high-throughput substrate analysis systems can include a cabinet, the cabinet including an upper region and a lower region, the upper region housing the substrate container storage tray, the substrate preparation station, the automated gripper, and the analysis mount, and the lower region housing the optical train. Optionally, during operation of the system, the environmental control system maintains a positive cabinet pressure in at least a portion of the cabinet. The optical train or the mount optionally includes one or more leveling or vibration damping components.

BRIEF DESCRIPTION OF THE DRAWINGS

FIG. 4C schematically illustrates a structure having a reaction region extending into the micromirror, and illustrates the incorporation of an optical component such as a filter into the micromirror structure.

FIG. 8 schematically illustrates an example optical system of the invention.

DETAILED DESCRIPTION

I. Overview

Figure 1:
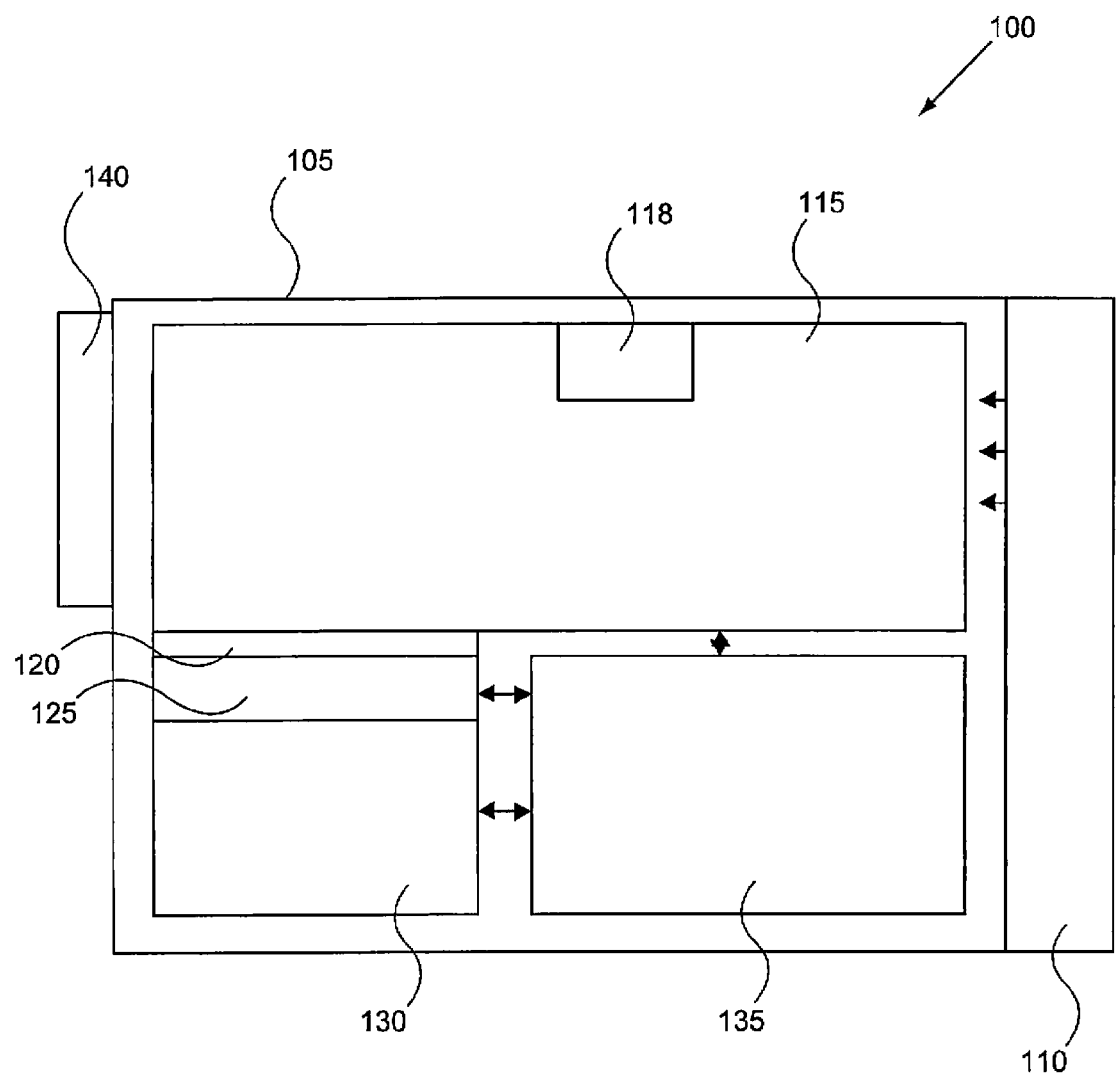
FIG. 1 is a schematic illustration of a substrate analysis system of the invention.

The present invention is generally directed to substrate analysis systems, devices and methods for the facile, efficient and cost effective analysis and/or management of collections of optical signals and the data derived from those signals. Of particular interest is the application of these devices, systems and methods in analyzing reactions of interest, e.g., chemical and biochemical reactions such as nucleic acid synthesis, and the characterization of the steps involved in those reactions.

While the overall systems, devices and methods of the invention can be employed broadly in a wide range of different applications, of particular interest is the use of these systems and methods in the analysis and characterization of chemical and/or biochemical reactions, which either naturally or artificially produce differing optical signals during the reaction process. There are a wide variety of different analytical reactions that produce multiple optical signals that benefit from the present invention. These include reactions that use optical signals of differing wavelengths, e.g., fluorescent and/or fluorogenic reactants or products, luminescent reactants or products, chromophoric and/or chromogenic reactants or products, etc. In a particularly preferred aspect, the systems, devices and methods of the invention are applied in analyses of replication, transcription and translation reactions, such as nucleic acid analyses and particularly nucleic acid sequence analyses.

The substrate analysis systems of the invention typically include one or more cabinets for housing the various components of the system. The cabinet can be environmentally closed to provide a user of the system with precise control over certain internal environment parameters, e.g., temperature, air pressure, humidity, and the like. The system can include an environmental control unit within (or operatively coupled to) the cabinet, which unit effects the environmental parameters chosen by the user. The system further includes a portion within the cabinet dedicated to substrate storage, the storage and handling of reagents and samples to be analyzed, and substrate preparation (e.g., the provision of reagents and samples to an analysis portion of one or more substrates). This portion of the system also includes robotics for moving one or more substrates, samples, reagents and the like between various locations of the system, as well as a monitoring system for tracking the location of such components within the cabinet, such as machine vision systems. Analysis systems of the invention include other portions within the cabinet for mounting the substrate and/or controlling the position of the substrate in multiple dimensions. Interfaced with the substrate mounting and control portion of the system is an optical system for providing excitation radiation to one or more reaction regions of the substrate, collecting optical signals emanating from the one or more reaction regions. The optical system includes components for optimizing signal collection, e.g., autofocus and/or alignment components that permit the quality of optical signals to be monitored and, in the event of suboptimal signal quality, enhanced. Also contained within the cabinet is a portion of the substrate analysis system for computational data analysis (e.g., for single molecule sequencing applications, determining and characterizing nucleotide incorporation events) and computer-implemented control functions, e.g., controlling the robotics, environmental conditions, focus and/or alignment of the various components of the optical system. Also provided is a user interface operatively coupled to the cabinet or components housed in the cabinet, permitting a user of the system to initiate and terminate an analysis, control various parameters (e.g., with respect to analysis conditions, internal cabinet environment, etc.), and manage/receive data (e.g., nucleic acid sequence data) obtained by the system.

An example substrate analysis system of the invention is schematically illustrated in FIG. 1. As shown, various components of substrate analysis system 100 are housed within cabinet 105. Cabinet 105 can be environmentally closed, such that the internal environment of the system (pressure, humidity, temperature, etc.) can be selected by a user and implemented by environmental control unit 110. Internal to the cabinet, the system includes portion 115 for substrate storage, reagent/sample storage and handling, substrate preparation, robotics for substrate movement and preparation, as well as monitoring functionality, e.g., machine vision system 118. The substrate can be placed at substrate mounting portion 120, where the position and/or orientation of a substrate analysis mount (and accordingly, the substrate) can be controlled by a positional control unit at portion 125. Optical system 130 includes optical components (e.g., optical energy sources, optical trains, optical detectors, etc.) for providing excitation radiation to reaction regions of the substrate, collecting optical signals from the reaction regions, and monitoring the focus/alignment of the substrate to enhance the quality of data collection. Provided at portion 135 are computational components for optical data interpretation, as well as components for controlling the various functions performed in other portions of the system. A user of the substrate analysis systems of the invention can control the various functions performed by the system, and manage/receive data, via user interface 140. It will be understood that certain portions/components of the substrate analysis systems are operably and/or physically coupled to one another, as indicated by the arrows in FIG. 1.

Also provided by the present invention are optical systems and/or modules for enhanced multiplex illumination of arrayed reaction regions disposed upon or within the substrate(s) to be analyzed, and for enhanced detection of optical signals emanating from reaction regions of the substrates.

Various system components, e.g., cabinets, environmental control units, substrates, substrate containers, automated grippers, substrate preparation stations, substrate analysis mounts, machine vision systems, optical systems/modules, signal analysis modules and user interfaces, as well as the functions and applications of the substrate analysis and optical systems of the invention are set forth in greater detail below.

II. Cabinet and Environmental Control Units

Substrate analysis systems of the invention include a cabinet for housing the substrates, samples, reagents, robotics, optical systems, compute/control components, and various other system components described herein. The cabinets of the invention are useful for providing a barrier between the internal and external environment of the system, e.g., preventing exposure of internal system components to unwanted particulate matter, electromagnetic radiation, temperature fluctuations, etc. that are present in the external environment. In preferred aspects, the cabinet consists of at least one opaque layer that prevents extraneous electromagnetic radiation from entering the internal portion of the system, which electromagnetic radiation can damage photolabile reagents and interfere with the optical systems of the invention. The cabinet optionally includes an insulating layer that facilitates the maintenance of a desired internal system temperature. Further, a light source, e.g., a UV light source, can be attached to an inner wall of the cabinet to irradiate internal components of the system, thereby preventing microbial growth inside the cabinet while the system is otherwise idle.

It is desirable for certain internal environmental parameters to be controlled while samples and reagents are present in the system, as well as during substrate preparation and analysis. For example, certain cooling components of the system are designed to store samples and reagents at a temperature (e.g., about 4° C.) where the samples and reagents are relatively stable during the period prior to analysis. Other heating or cooling components (e.g., Peltier heating or cooling structures) are optionally included for increasing or reducing the temperature of components that are prone to heating during operation of the system, e.g., substrates, substrate analysis mounts and optical elements that may increase in temperature due to, e.g., the generation and presence of excitation radiation. Such cooling components can lead to, e.g., unwanted water vapor condensation within the cabinet that can adversely affect the performance of the system. To this end, an environmental control unit that includes an optional dehumidifier can be operably coupled to the cabinet to reduce or eliminate humidity within the cabinet to prevent the build up of condensation on system components.

The environmental control unit can be configured to control additional environmental parameters within the substrate analysis systems of the invention. For example, the unit can create positive air pressure inside the cabinet to prevent contaminants (e.g., bacteria, viruses, and other airborne contaminants) which could introduce analysis interfering nucleic acids, nucleases, and the like, from entering the system. As will be appreciated, the cabinet can include an insulating layer as well as materials for sealing the junctions between one or more cabinet doors and the cabinet (e.g., sealing strips made of silicon, rubber, plastic, a polymer or other suitable sealing material around the perimeter of one or more cabinet doors)—to permit positive pressure within the cabinet and facilitate the control of other environmental parameters within the cabinet (e.g., humidity, temperature, etc.).

III. Substrates

Substrates that can be used with the substrate analysis systems of the invention can take any of a variety of physical configurations, e.g., planar, substantially planar, cubic, spherical, etc. As a general matter, the substrates typically provide a location for the production of multiple discrete sources of optical signals, e.g., from discrete reactions on a surface or other region of the substrates. In the case of systems for monitoring reactions, signal sources can arise from discrete regions of the substrate, in which reactions are taking place and from which discrete optical signals can emanate. In a broad sense, such different regions can comprise reaction wells, or zones that are maintained discrete from other regions by any of a number of different mechanisms, including chemical, electrical, optical or physical confinements. Merely by way of example, such regions can comprise discrete patches or zones of immobilized molecules on a surface of the substrate, such as in nucleic acid, protein, antibody or other immuno-arrays. Where the reaction being monitored is the association of analytes with such immobilized molecules, the regions can include channels within a substrate, e.g., microfluidic channel regions, aggregations of capillaries or multiple regions within individual capillaries, or the like.

Alternatively or additionally, such regions optionally include structural confinements that maintain the reaction components within the discrete regions. Such structural confinements optionally include wells, depressions, channels, or other structures that retain reaction constituents. Such confinements can also include other barriers that effectively provide structural confinement through, e.g., the use of chemical barriers, e.g., hydrophobic regions surrounding hydrophilic regions on the substrate surface to retain aqueous reaction constituents within the hydrophilic regions.

In still other aspects, such regions optionally include combinations of the above, e.g., including immobilized reactants within structural confinements. In addition to structural confinements, the reaction regions can comprise optical confinements that can function as or in addition to structural confinements on the substrates, that serve to minimize observation volumes on the substrate through the confinement of excitation illumination and/or the collection of emitted optical signals from relatively small areas or volumes at the reaction region. Such optical confinements optionally include, e.g., confinement structures, such as zero mode waveguides, TIRF surfaces, and the like. Additional optical elements may optionally be included within or on the substrates, including, e.g., waveguides, optical gratings, optical coatings or the like, e.g., that can yield the excitation or observation volumes desired on the reaction regions on the substrates.

Typically, the substrates can comprise an optically transparent layer upon which are disposed the reaction regions that provide the discrete sources of optical signals. The optically transparent layer can generally comprise any of a number of transparent solid materials, depending upon other components of the substrate. Such materials include inorganic materials, such as glass, quartz, fused silica, and the like. Alternatively, such materials may include organic materials, such as polymeric substrates such as polystyrene, polypropylene, polyethylene, polymethylmethacrylate (PMMA), and the like, where PMMA is particularly useful in illuminated reactions such as fluorescent or fluorogenic reactions, as it has relatively low autofluorescence.

In preferred aspects, the substrates include zero mode waveguides as the optical confinements to define the discrete reaction regions on the substrate. Zero mode waveguides have been described in, e.g., U.S. Pat. No. 6,917,726, the full disclosure of which is incorporated herein by reference in its entirety for all purposes. Briefly, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between 1 nm and 200 nm, and are preferably between about 10 and 100 nm, and more preferably between about 30 and about 100 nm in diameter.

Optical confinements are typically provided upon the substrate in an array format where a plurality of confinements are provided upon the substrate. In accordance with the invention, arrays of confinements, e.g., zero mode waveguides, are provided in arrays of more than 1000, more than 10,000, more than 50,000 (e.g., 80,000) more than 100,000, or even more than 1,000,000 separate zero mode waveguides on a single substrate. In addition, the waveguide arrays typically comprise a relatively high density of waveguides on the surface of the substrate. Such high density typically includes waveguides present at a density of greater than 10 zero mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format.

As noted above, other optical confinement strategies may additionally or alternatively be employed, including, for example, the use of optical waveguides disposed within or upon the surface of a substrate which can deliver an evanescently decaying illumination of materials at or near the surface of the waveguides. Such systems are described, for example, in Published U.S. Patent Application No. 2008-0128627, the full disclosure of which is hereby incorporated herein by reference in its entirety for all purposes.

Optical systems often include a number of optical aberrations, including, e.g., astigmatism, chromatic aberrations, coma, distortion, field curvature, and spherical aberration. In many instances, these optical aberrations become more pronounced as a function off distance from the axial center of the optical imaging system, such that the magnitude of the aberration varies as a function of field position. Accordingly, the optical image is typically most free of aberrations at or near the center of the object field, and is more distorted at the periphery of the object field and system pupil. Because of such aberrations, resolution and accurate monitoring of arrays of discrete nanometer or micron scale sources of optical signals that are provided in a relatively high density becomes increasingly problematic away from the center of the object field. Consequently, performing analyses in a highly multiplexed array of waveguides or other signal sources becomes more difficult.

Therefore, the sources of discrete optical signals, e.g., the optical confinements, i.e., zero mode waveguides, in array formats, can be arranged within the array in a non-regular format, to minimize or otherwise adjust for the impact of these expected optical aberrations, and as a result permit more effective multiplexed analyses. In particular, individual sources of signal in the array may be positioned to account for reduced resolution, e.g., between neighboring sources, as a function of distance from the center of the object image. Additionally, or alternatively, the discrete sources may be dimensioned to account for reduced resolution and accuracy at the periphery of the object field. The variance in optical resolution, or conversely, aberration, as a function of distance from the center of the object field are particularly noteworthy in systems that rely upon imaging based detection systems, e.g., that effectively image an entire array or region of an array, that includes multiple different signal sources. Examples of such systems include detector arrays, such as diode arrays, CCDs, i.e., ICCDs and EMCCDs, and/or CMOS based image sensors, where signals are detected at individual or small groups of pixels on the detector. For example, in CCD based detectors, as signals become more distorted away from the axial center of the imaging system, it becomes increasingly difficult to assign pixel areas on the CCD that correspond to a given signal source in the array of signal sources.

Figure 2:
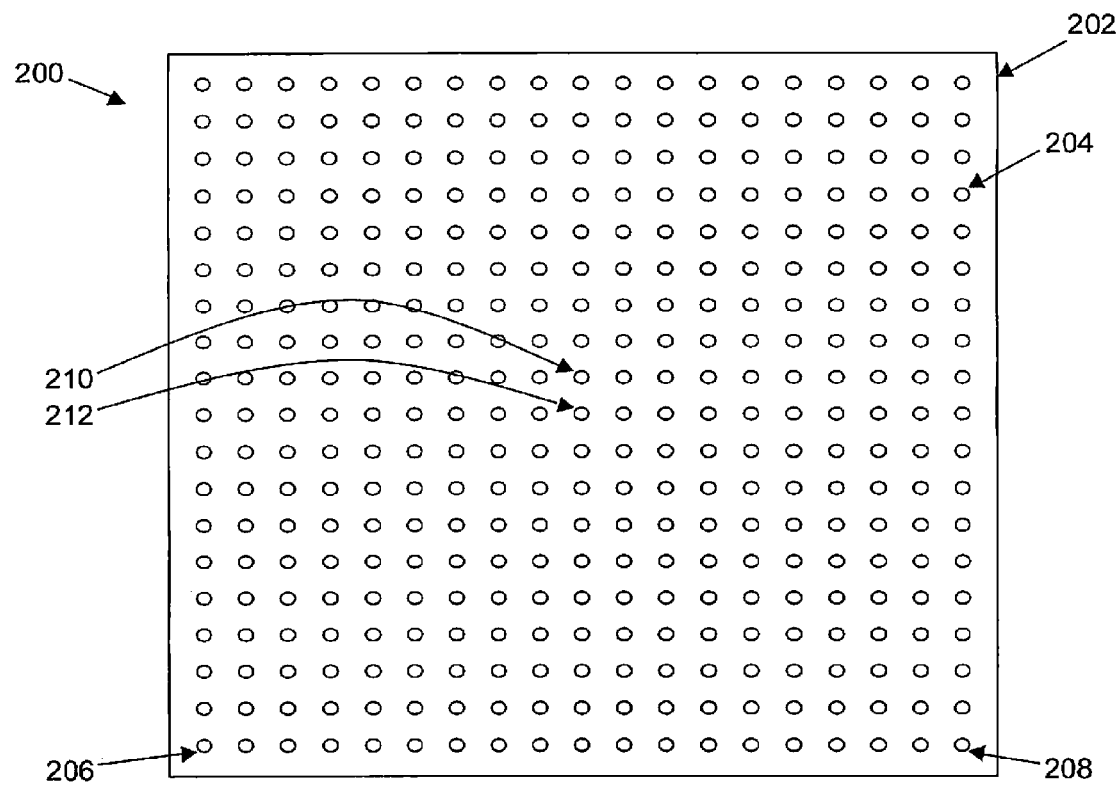
FIG. 2 provides a schematic illustration of an array of signal sources on a substrate, such as zero mode waveguides.
Figure 3:
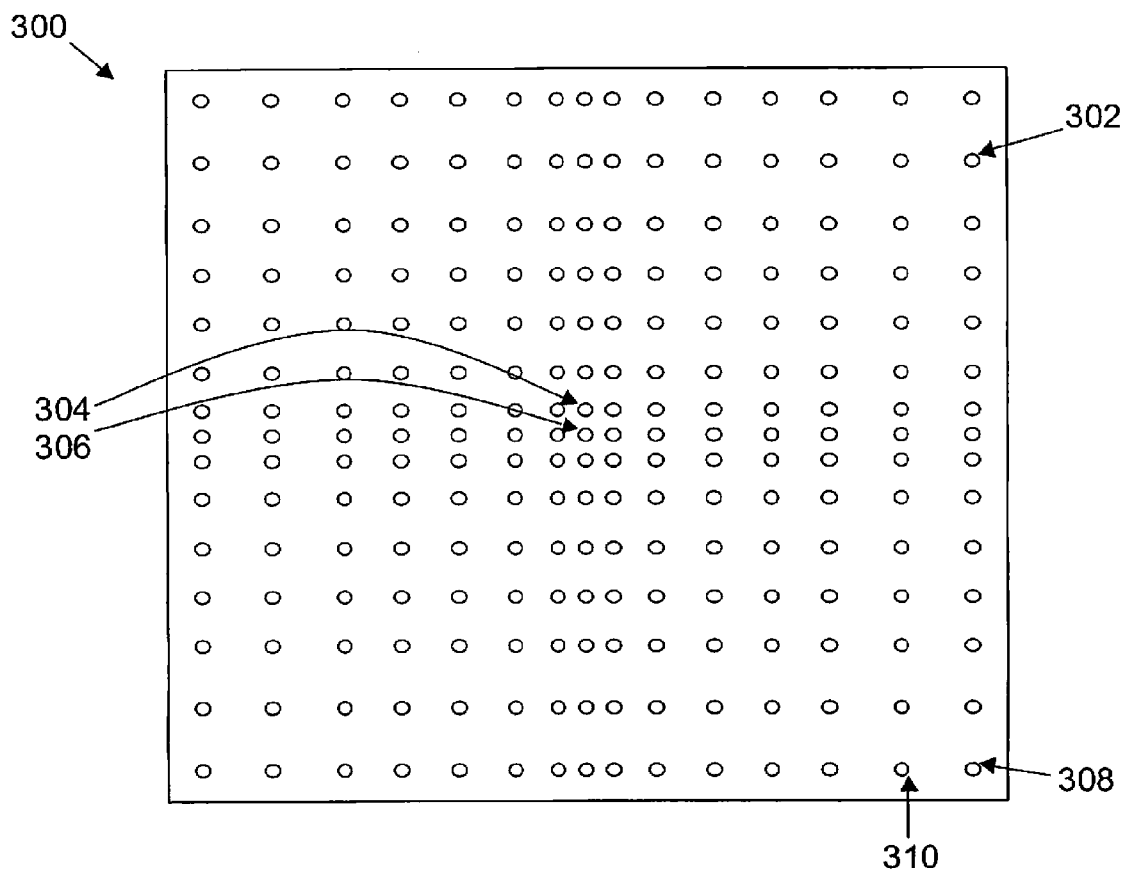
FIG. 3 provides a schematic illustration of an alternative spacing and/or orientation scheme for an array of signal sources, in accordance with certain aspects of the invention.

FIG. 2 and FIG. 3 show a comparative illustration of arrays of sources of optical signals. FIG. 2 shows an array 200 of sources of optical signals (shown as an array of zero mode waveguides 204 in a substrate 202) that includes regularly spaced and consistently sized sources of optical signals. As noted previously, in some cases the sources at the periphery of the array, e.g., sources 206 and 208 would be less resolved, optically, than, e.g., sources 210 and 212. In some cases, it may be the case that aberrations could be sufficient to prevent resolution of the peripheral sources, e.g., 206 and 208. Accordingly, as shown in FIG. 3, an array 300 of sources 302 is provided where the spacing between adjacent sources is increased as a function of the distance from the center of the object image. For example, as shown, signal sources that are nearer the center of the object field represented by the array 300, e.g., sources 304 and 306 are closer together in at least one dimension, than are sources that further away from the center of the object field, e.g., sources 308 and 310, which are more widely spaced in at least one dimension than the more central signal sources. Thus, the space, in at least one dimension between two sources at a first distance from the center of the object field of the optical system will be less than the space, again in at least one dimension, between two sources that are at a second, greater distance from the center of the object field. The spacing between adjacent signal sources may be varied in only one dimension, e.g., varied from left to right, but not from top to bottom, or it may be varied in both dimensions. In the case where the spacing is varied in both dimensions, it will be appreciated that the distance between any two signal sources at the center of the object field, e.g., is less than the space between any two signal sources further away from the center, i.e., on the periphery, of the object field. The foregoing permits greater effective multiplex analysis of arrays of signal sources, such as ZMWs.

Additional arrangements of array elements can be specifically tailored to fit a particular aberration of particular optical systems. For example, if a dominant optical aberration forms a resulting image spot size or shape that is dependent upon field location, then that size or shape can be accommodated in the design of the array of sources by, e.g., appropriately spacing the sources to avoid overlap in image of adjacent sources, or the like. Similarly, if the shape of an imaged source is distorted in one dimension so as to potentially overlap with images of neighboring sources, that source can be dimensioned to reduce that dimension and avoid the overlap, e.g., providing elliptical or rectangular sources. In a simpler aspect, the signal sources may also be spaced to account for optical manipulations of the signals emanating therefrom. For example, as discussed in greater detail below, in some cases, optical signals are spatially separated into component elements, e.g., light of different wavelength ranges, indicative of different signaling elements, i.e., fluorescent reagents having differing emission spectra. In such cases, it may be desirable to provide sufficient spacing between adjacent signal sources on the substrate to prevent overlap of the spatially separated signals derived from those sources, when those separated signals are incident upon the detector, as set forth below. In this case, increased spacing may only be required in one dimension, e.g., providing sufficient spacing between rows of signal sources, but not necessarily between the columns of signal sources in the array. Alternatively, such additional spacing may be provided in two dimensions. In the case of arrays of signal sources where the signals are subjected to spatial separation before detection, such spacing between adjacent signal sources may generally range from about 0.1 µm to about 10 µm or more, and is preferably from about 0.8 µm to about 3 µm or more.

Substrates that can be used with the substrate analysis systems of the invention optionally comprise an array of shaped micromirrors wherein each micromirror is associated with an optical confinement (e.g., a zero mode waveguide), and in particular an array of shaped micromirrors that is incorporated into the same substrate that comprises the optical confinements. Such micromirror arrays are useful for minimizing optical cross-talk among signals emanating from reaction regions of the substrate and providing for increased levels of illumination by directing illumination light into a reaction region on an array, such as an array of zero-mode waveguides. Further details regarding micromirror arrays can be found in International patent application PCT/US2009/005319 by Zaccarin et al. entitled "ULTRA-HIGH MULTI-PLEX ANALYTICAL SYSTEMS AND METHODS", filed Sep. 25, 2009, the full disclosure of which is incorporated herein by reference in its entirety for all purposes. Details regarding intermittent illumination and/or detection approaches that find use with micromirror arrays are described in, e.g., United States Patent Publication No. US 2010/0075327 by Maxham et al. entitled "INTERMITTENT DETECTION DURING ANALYTICAL REACTIONS", the full disclosure of which is incorporated herein by reference in its entirety for all purposes.

Figure 4A:
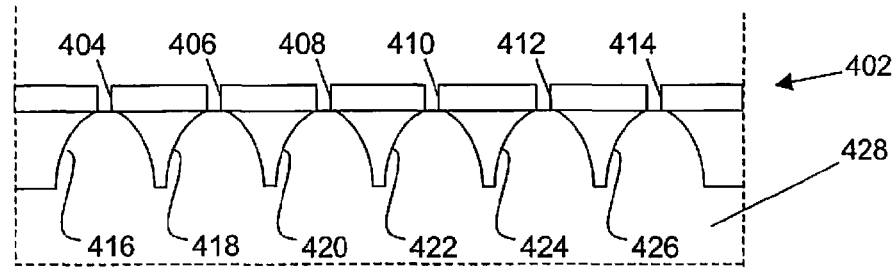
FIGS. 4A, 4B and 4C schematically illustrate a substrate employing shaped mirrors as focusing optics for efficient light collection from reaction regions on the substrate and for efficient illumination of the reaction regions.

An example of an array of shaped micromirrors in accordance with the invention is illustrated in FIG. 4A. As shown, the overall substrate 402 includes an array of reaction regions, such as zero-mode waveguides 404-414, disposed upon its surface. Conical or parabolic mirrors 416-426 are integrated into the underlying transparent substrate 428, and are configured to redirect or to focus both the incoming and outgoing light to and from the ZMWs in the array. In particular, the conical or parabolic mirrors are typically comprised of a reflective material, such as a metal layer, e.g., aluminum, silver, gold, chrome, or the like, manufactured into the underlying substrate to provide the mirror surfaces.

Figure 4B:
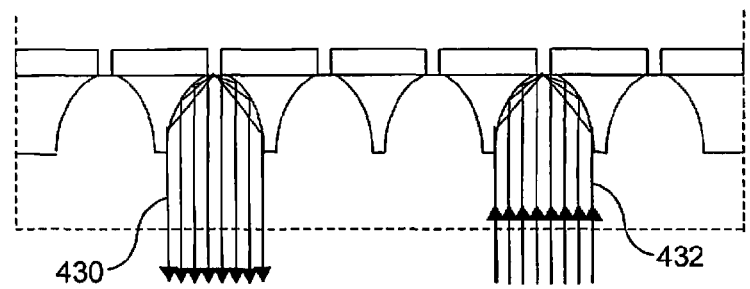

As shown in FIG. 4B, fluorescent signals 430 emitted from the reactions within the ZMWs are redirected or focused by a mirror, such as a parabolic or conical mirror, increasing the efficiency with which such signals are collected. As shown here, for example omni-directional emitted light coming into the reaction regions on the substrate is redirected such that it is more readily detected. In some cases, as illustrated here, the light can be at least partially collimated. In addition, for each reaction region or ZMW, the mirror structure reduces or eliminates inter-ZMW cross-talk within the substrate itself. In addition to the reduction in cross-talk, it will be appreciated that the enhanced collection efficiency resulting from redirection or focusing of the emitted light also increases the sensitivity of the system. Likewise, the shaped optic elements will also serve to focus incoming illumination, e.g., light 432, onto the reaction regions such as ZMWs 404-414.

Figure 4C:
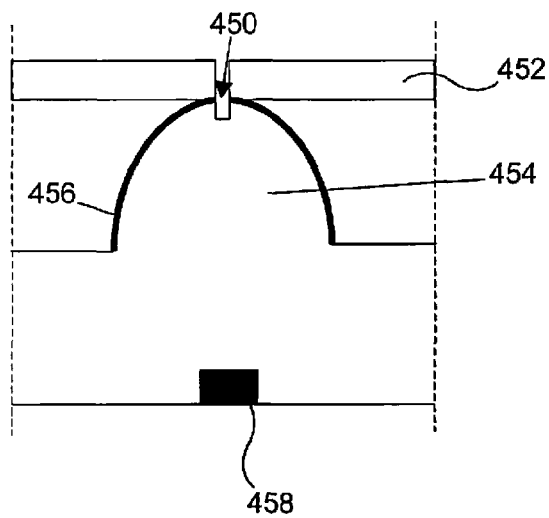

Alternative configurations may also be adopted for the devices incorporating these conical mirrors. For example, a zero mode waveguide core region may be extended into the underlying substrate. This example is illustrated in FIG. 4C, in which the reaction region 450 extends beyond cladding layer 452, and into the underlying substrate 454, allowing in some cases for more efficient signal transfer to and from the reaction region 450, that is reflected off of mirror 456. Optional components such as light blocking regions or filter components may be additionally included within the overall structure, including, for example, mask 458, to further enhance the optical properties of the mirror system.

The shaped mirrors are generally micromirrors, meaning that the mirrors are small, generally having dimensions on the order of microns or tens of microns. In some cases the term microreflector is also used to refer to a micromirror. The mirrors can have a cross-sectional dimension from about 0.1 micron to about 100 microns, about 1 micron to about 50 microns, or about 2 microns to about 20 microns. While the mirrors typically have dimensions on the order of microns to tens of microns, in some cases, the shaped mirrors of the invention can be larger, for example from about 100 microns to about 1 mm or greater.

The micromirror arrays can be fabricated at a high density as described above for ZMW arrays. The density of micromirrors associated with reactive regions can be, for example, anywhere from 1000 ZMWs per $cm^2$, to 1,000,000 ZMWs per $cm^2$, or more. At any given time, it may be desirable to analyze the reactions occurring within 1000, 10,000, 20,000, 50,000, 80,000, 100,000 or 1 Million, 10 Million or more ZMWs or other reaction regions on a single substrate or within a single substrate analysis system using the micromirror arrays described herein.

IV. Substrate Containers and Substrate Container Storage Trays

Substrate analysis systems of the invention can include a region within the cabinet for storing substrates. In one useful configuration, the substrates are enclosed within a sealed tray to prevent undesirable substances from contacting the substrates prior to loading analytes onto the substrates. As the substrate analysis systems are configured to analyze multiple substrates in rapid succession (or to analyze multiple substrates in an alternating fashion), substrate container storage trays can be configured to store one or more substrates in a single tray, e.g., 1, 5, 8, 10 or more substrates in a single tray. Further, the tray can include fiducials (registration marks) that assist in the localization of the one or more substrates by the analysis system's robotics components.

Each cell of the substrate container storage tray is sealed from the external environment. For example, the tray may comprise a plastic, metal or other material at the base or sides of the tray. Each cell of the tray can include a face, e.g., an upper face, made of a pierceable material (e.g., foil, a plastic membrane, or the like) that forms a seal at the face and permits ready removal of the substrate for subsequent preparation and analysis. To permit storage of a large number of substrates, multiple substrate container storage trays can be present simultaneously within the cabinet.

Figure 5:
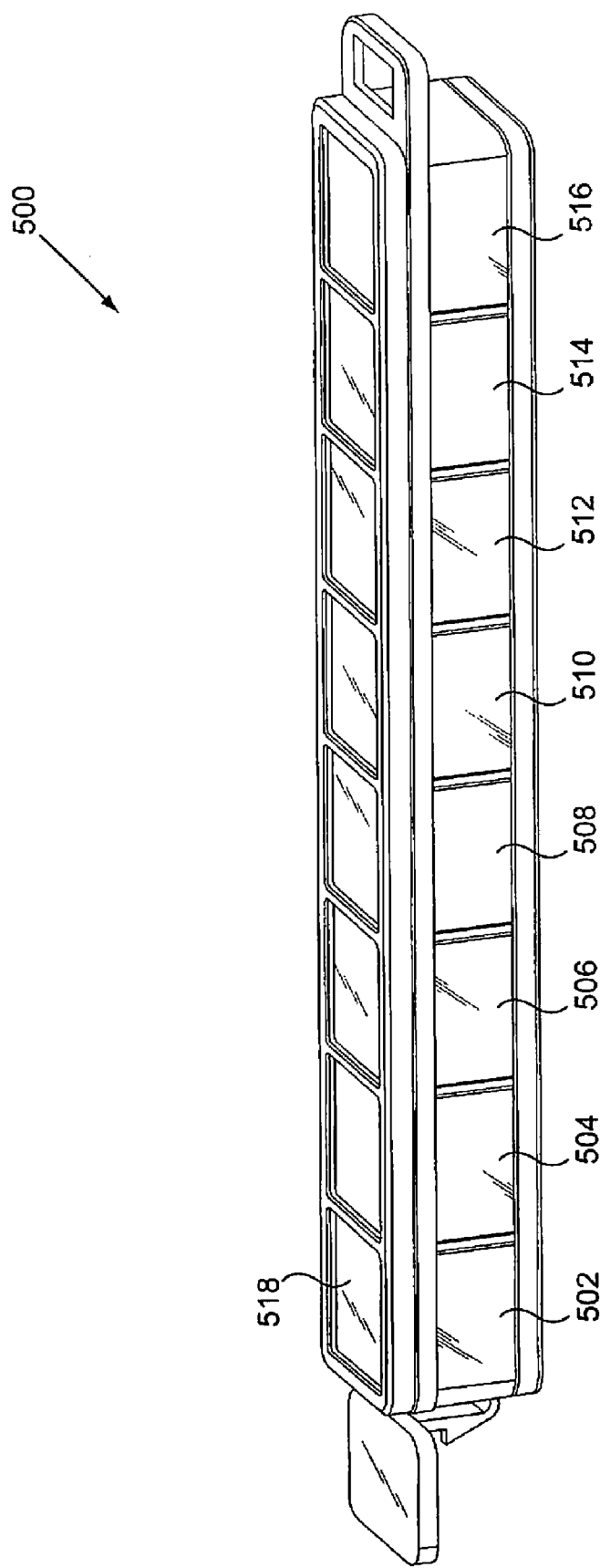
FIG. 5 is an illustration of an example substrate container storage tray of the invention.

An example substrate container storage tray of the invention is illustrated in FIG. 5. In this example, tray 500 is configured to store eight substrates (not shown), where each substrate is stored in a separate cell of the tray, e.g., cells 502-516. A face of each compartment, e.g., foil face 518, is made of a pierceable material that facilitates extraction of a substrate by a gripper, e.g., an automated gripper of the present invention as described herein. Further details regarding substrate containers and substrate container storage trays can be found, for example, in U.S. Patent Application No. 61/261,212 filed on Nov. 13, 2009, the full disclosure of which is incorporated herein by reference in its entirety for all purposes.

V. Automated Gripper

As noted herein, substrate analysis systems of the invention typically include robotics for moving one or more substrates, samples, reagents and the like between various locations of the system. With respect to the movement of substrates, the present invention provides an automated gripper operably connected (e.g., physically, electronically, or the like, as appropriate to the gripper) to the robotics, where the gripper is capable of attaching to a substrate carrier physically associated with the substrate and moving the carrier and associated substrate to precise locations within the cabinet. The substrate carrier serves as an intermediary between the gripper and the substrate and eliminates any requirement for the gripper to come into direct contact with the substrate. The gripper optionally includes teeth for enhanced gripping of the substrate carrier.

When one or more substrates are stored in a substrate container storage tray with a pierceable face on each cell of the tray, the gripper can have a piercing shaft to penetrate the pierceable face and to enter the cell with an end-effector and extract the substrate from the tray via a complementary physical interaction between the end-effector and substrate carrier. Optionally, the gripper and associated robotics can be configured to detect fiducials on the storage tray to determine the precise location of one or more cells of the tray.

Figure 6A:
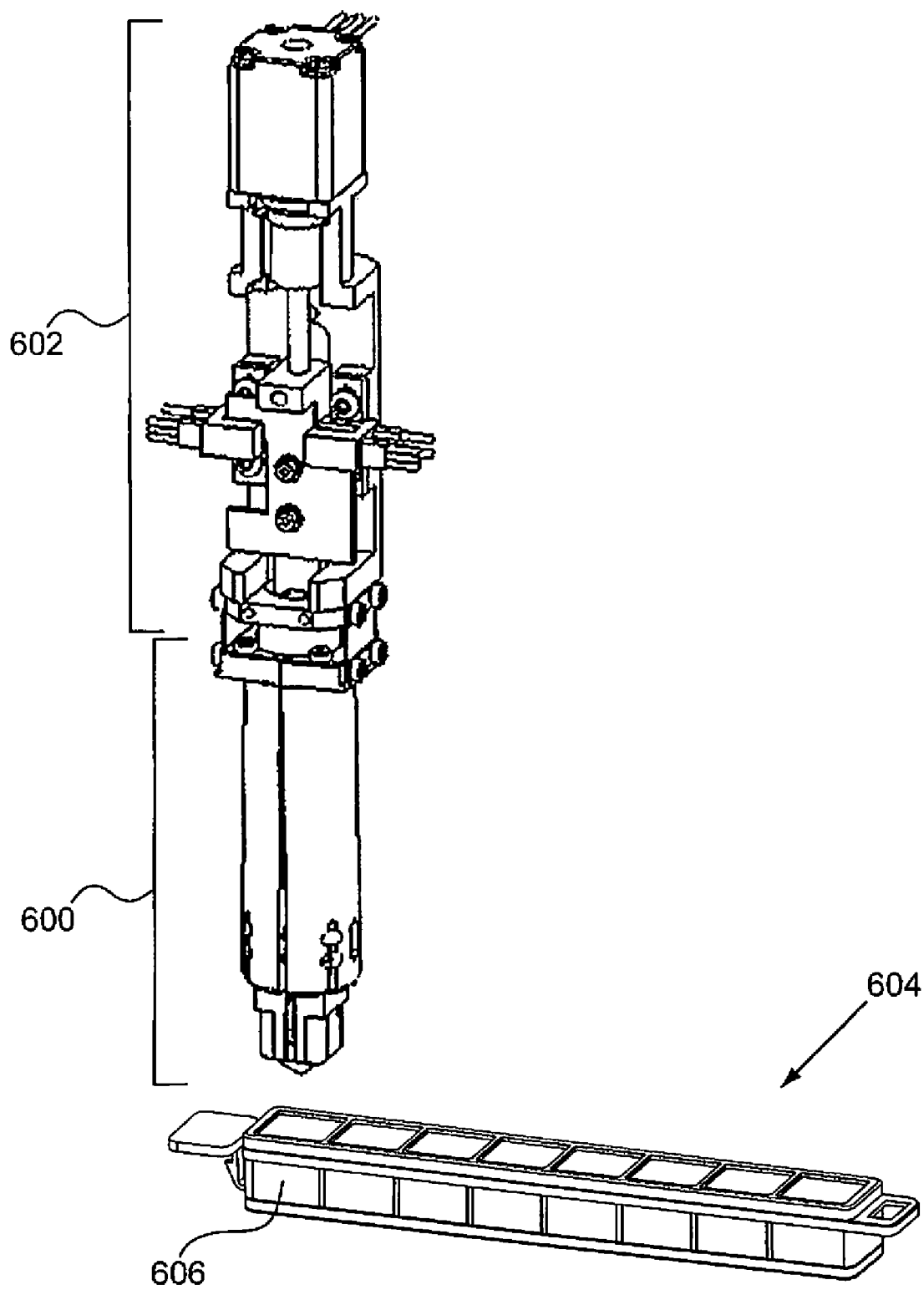
FIG. 6 is an illustration of an automated gripper of the invention.
Figure 6B:
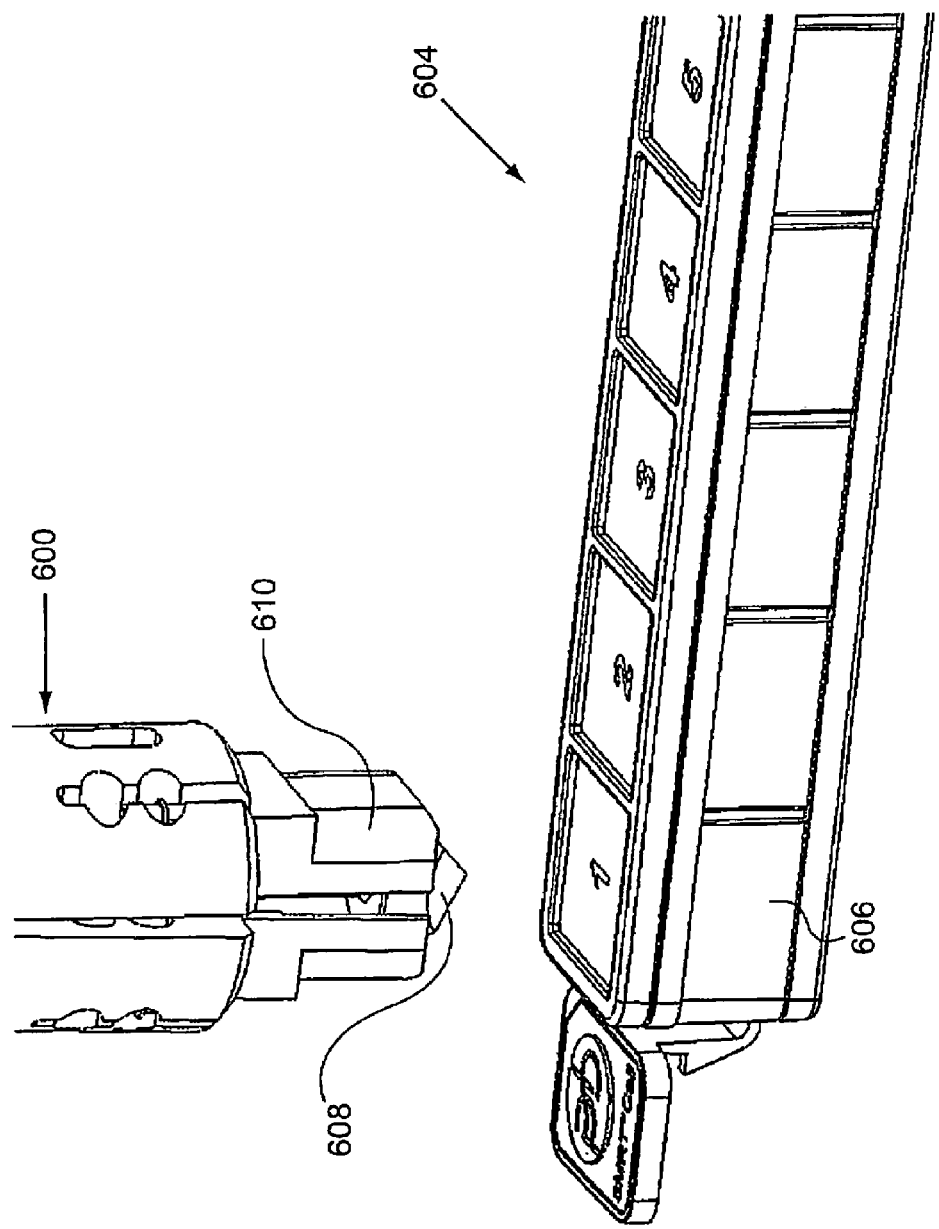
Figure 6C:
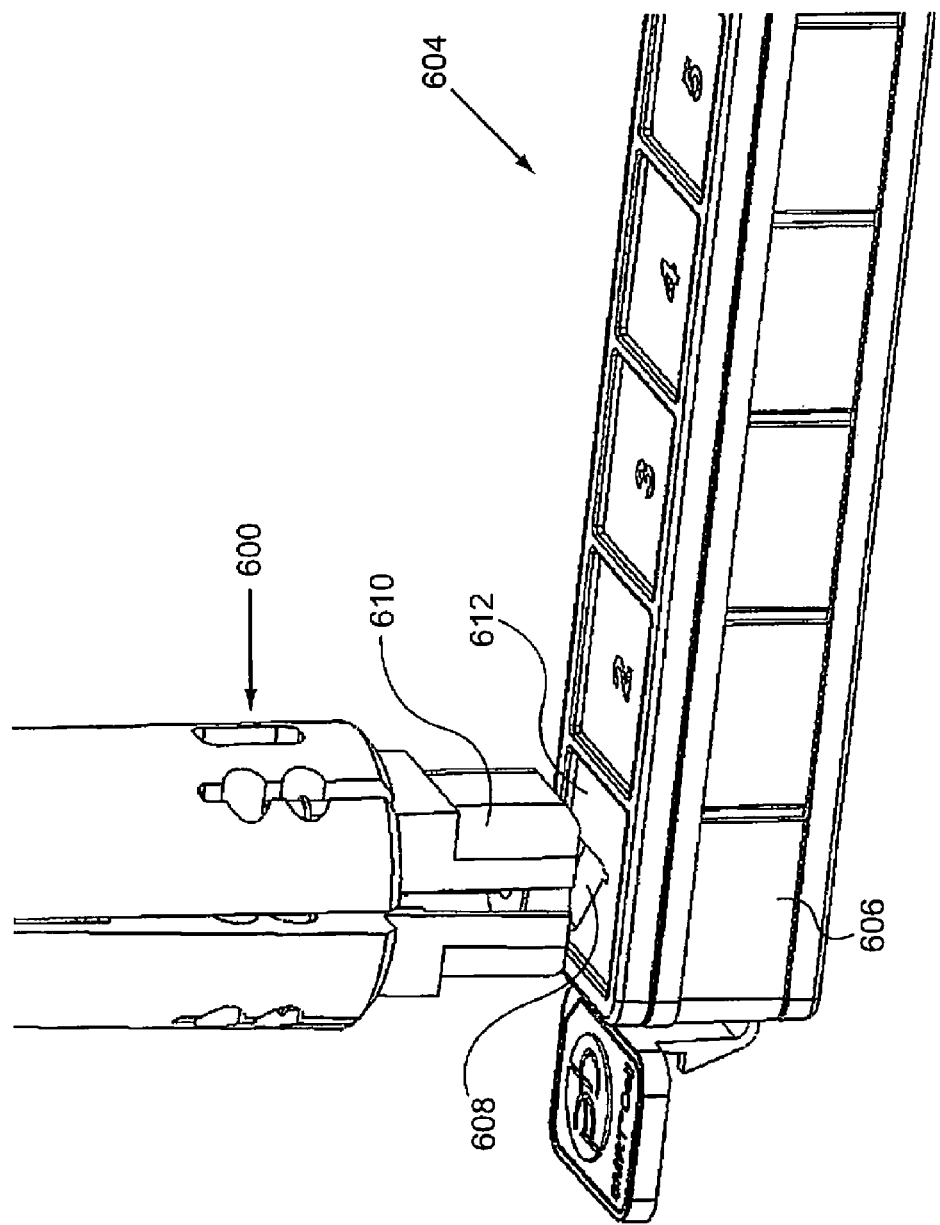
Figure 6D:
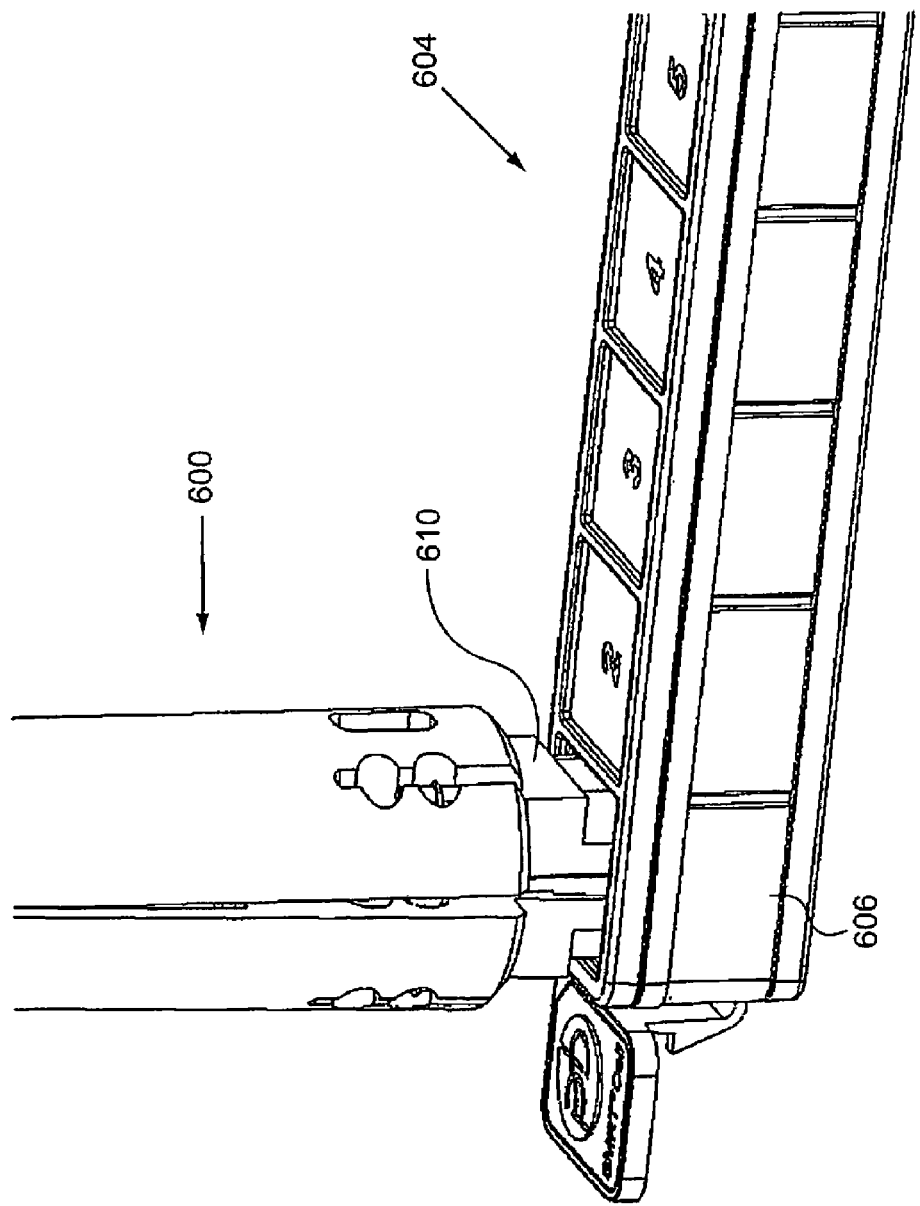
Figure 6E:
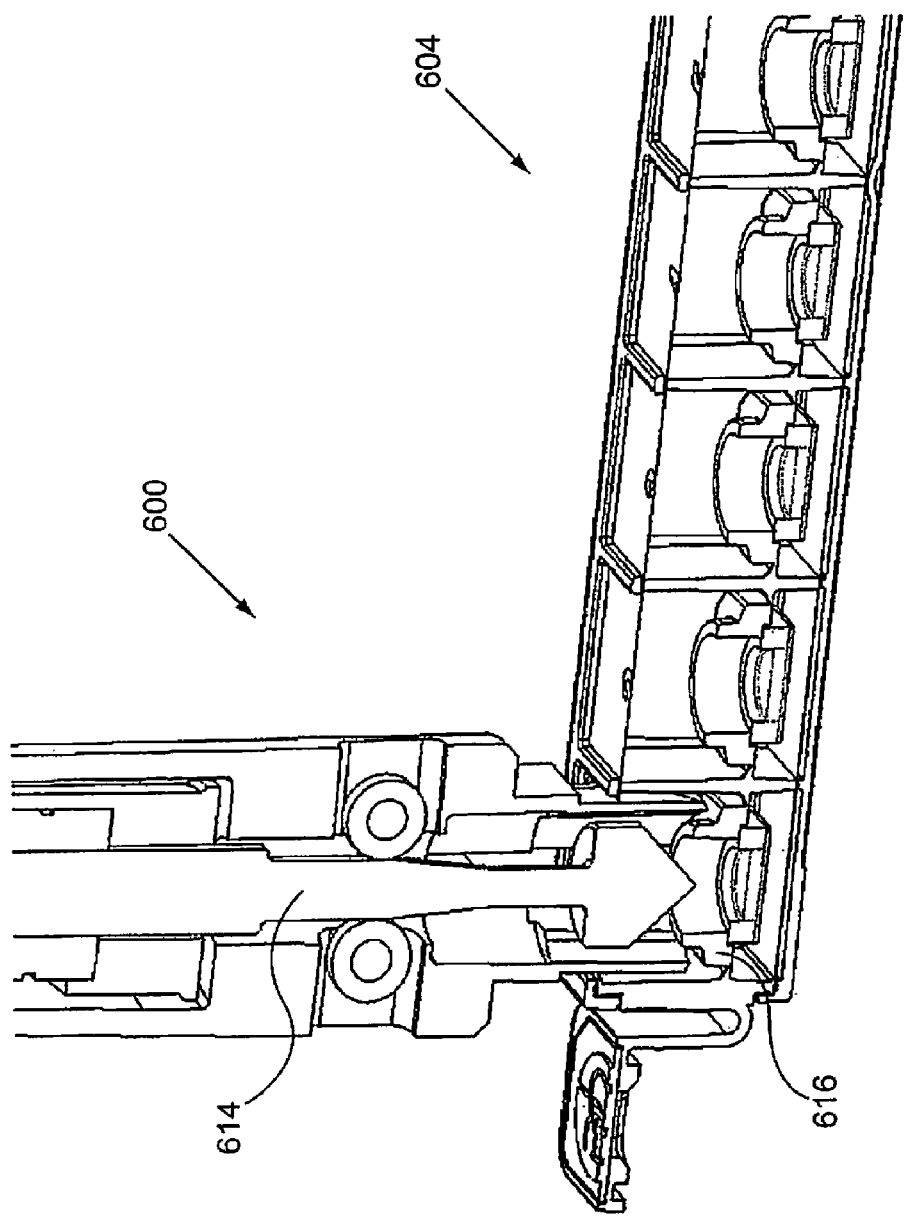
Figure 6G:
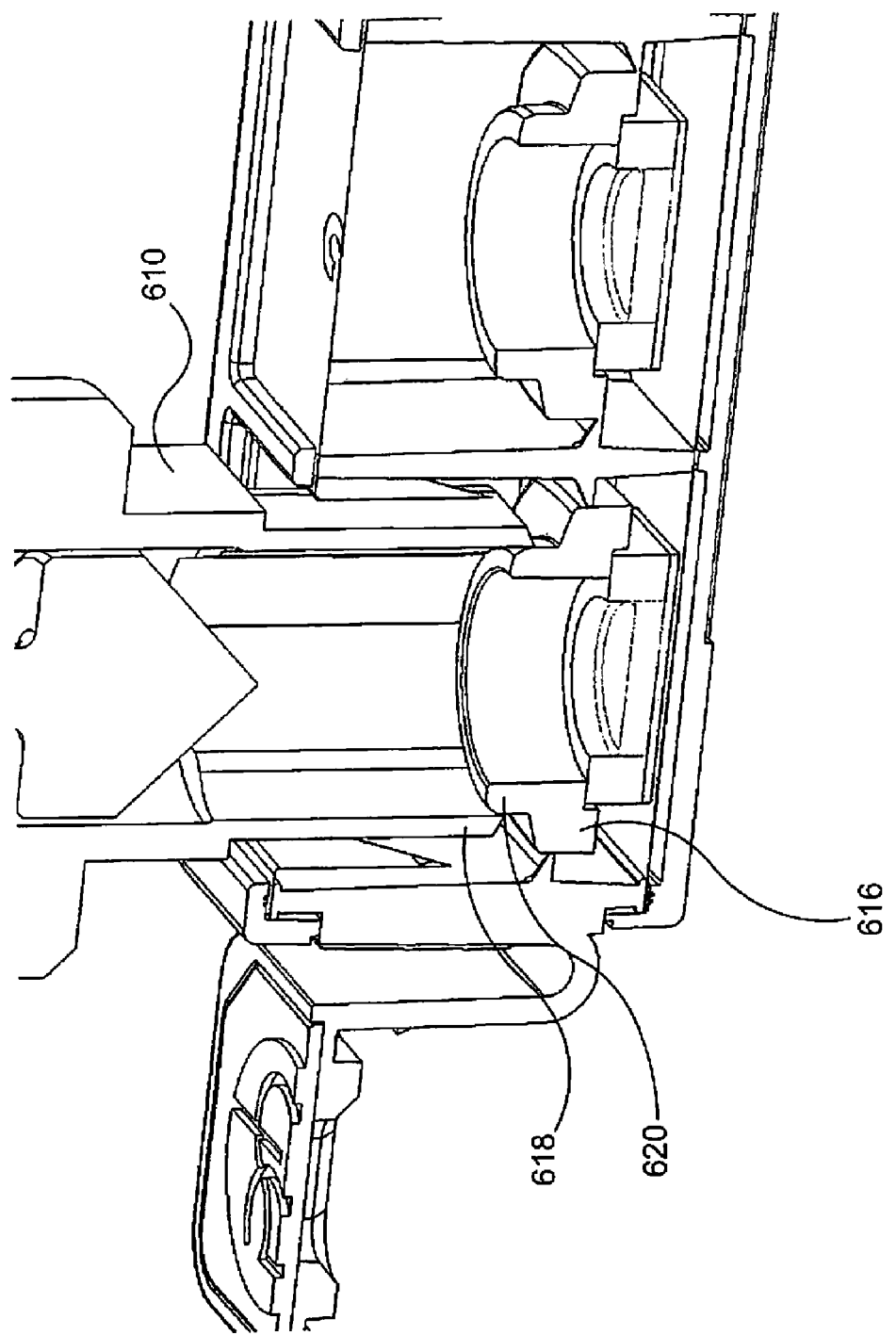
Figure 6H:
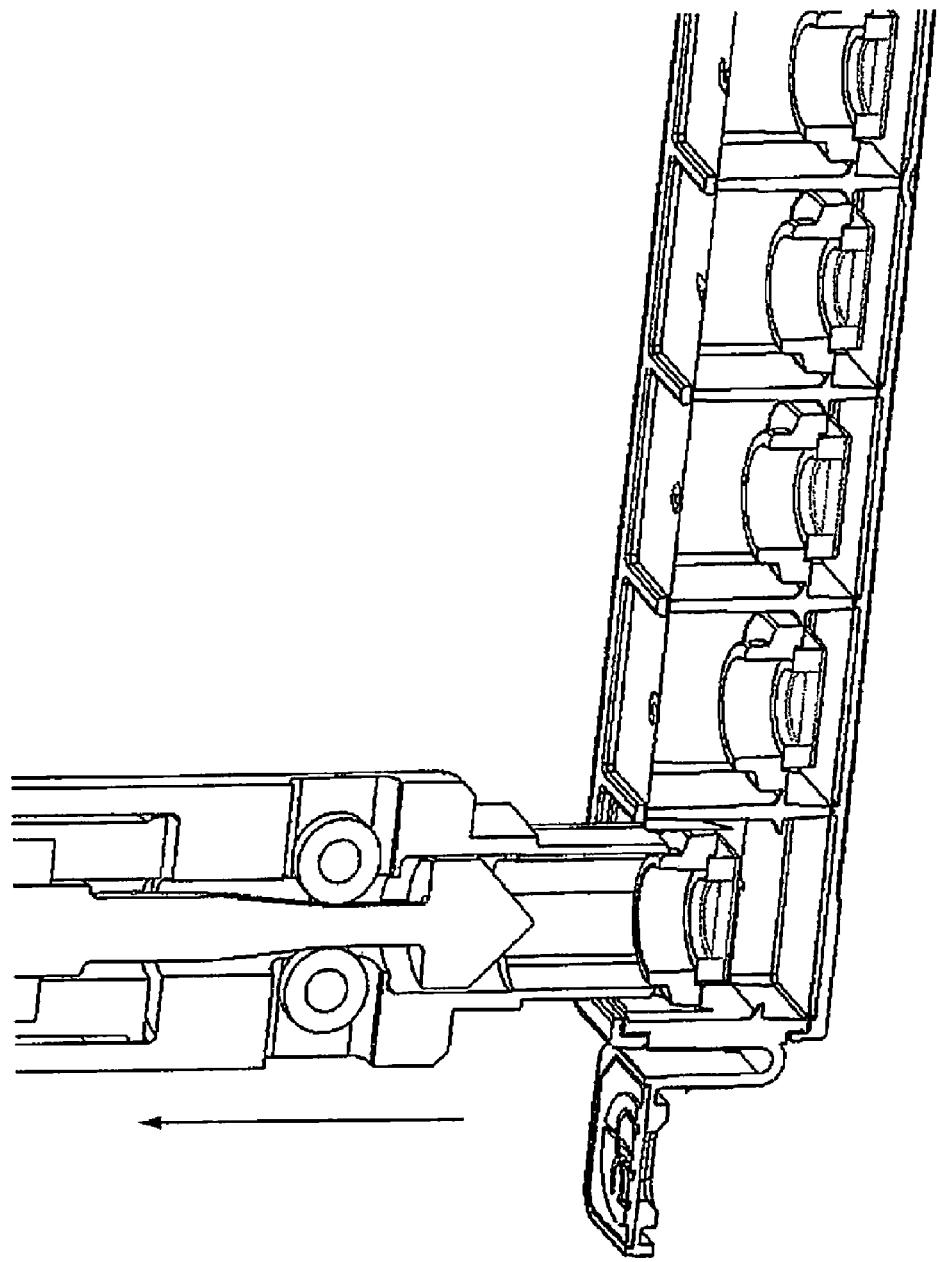
Figure 61:
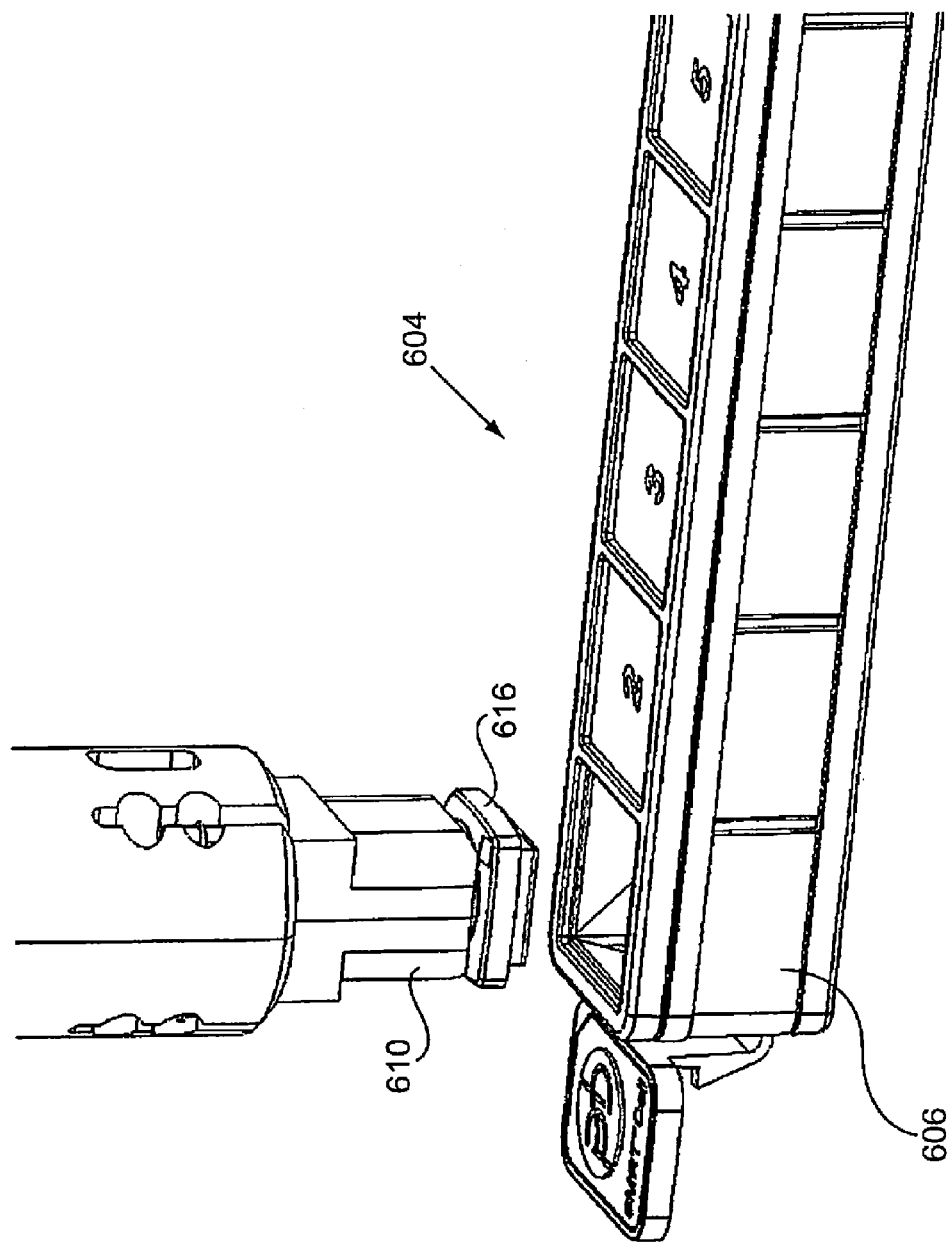

The elements and operation of an example automated gripper of the invention is illustrated in FIGS. 6A-6I. As shown in FIG. 6A, automated gripper 600 and associated robotic arm 602 can utilize fiducials (not shown) on substrate container storage tray 604 to become positioned above cell 606. The gripper includes a piercing shaft with an associated piercing member at the terminus of the shaft. Turning to FIG. 6B, as the piercing shaft extends, piercing member 608 emerges from end effector 610 at the lower portion of gripper 600. Emergence of piercing member 608 can occur prior to, or during downward movement of, the robotic arm and associated gripper. As shown in FIG. 6C, downward movement of the arm and gripper initiates contact between piercing member 608 and a pierceable face of the tray, e.g, foil seal 612. Subsequent to piercing of foil seal 612, the piercing member retracts back into the gripper and end effector 610 enters cell 606 as the robotic arm and gripper continue to move downward, as shown in FIG. 6D. FIG. 6E shows a horizontal section through the midline of gripper 600 and substrate container storage tray 604. Piercing shaft 614 is visible in this view. Also visible are substrate carriers of the invention, e.g., substrate carrier 616 disposed within cell 606. As shown in FIG. 6F, once the substrate carrier is located by the gripper, terminal portion 618 of end effector 610 grasps the substrate carrier by carrier collar 620. Substrate carrier 616 can be supported above the substrate (not shown) by support collar 622. When the robotic arm and gripper supply a minimum amount of downward pressure on the carrier, mediated by the interaction of terminal portion 618 of end effector 610 with carrier collar 618, support collar 620 can be sheared as the substrate carrier is pushed downward to secure the substrate, as shown in FIG. 6G. Extraction of the substrate carrier and associated substrate commences as the gripper moves upward towards its original position, as shown in FIG. 6H. FIG. 6I shows substrate carrier 616 and associated substrate (not shown) fully extracted from cell 606 of tray 604, mediated by grasping of the carrier by end effector 610 of gripper 600.

VI. Substrate Preparation Stations

Samples, reagents, and the like, are typically delivered to an analysis portion of a substrate (e.g., at least one reaction site, e.g., ZMW array) before analysis of the substrate is performed. Accordingly, substrate analysis systems of the invention include one or more substrate preparation stations within the cabinet to which substrates are transported from a substrate storage area, and where reactants are functionally delivered to the substrate. Once the reactants are delivered to the substrate and other conditions established by a user of the system are met, the substrate is then moved to a substrate analysis mount where analysis of the substrate commences.

Delivery of reactants to reaction sites of a substrate can be achieved, e.g., via pipettor-mediated delivery. In one class of examples, the substrate preparation station includes an automatic pipetting station for automated delivery of the reactants to the substrate. By way of example, the pipetting station can consist of one or more pipette tip storage boxes (e.g., providing micropipettes in 96 well or other format) and a plate or plates containing one or more reactants in one or more wells of the plates. A robotic arm configured to grasp (or mate with) one or more pipettes can submerge the tips of the one or more pipettes in the well(s) of a plate, create negative pressure within the one or more pipettes to draw the solution into the one or more pipettes, and move the tip to a position proximal to the substrate (e.g., immediately above the substrate) and deliver the reactants to the substrate. As will be appreciated, the robotic arm can deliver individual reactants to the substrate in a stepwise fashion, or the arm can be configured to mix two or more reactants (or a complete reaction mixture) and deliver the reactant mixture to the substrate. It may be desirable for some applications to deliver a reaction mixture in which a necessary component (e.g., one or more divalent metal ion catalysts, e.g., in a single molecule sequencing application) is absent from a reactant mixture initially delivered to the substrate, but which component is added immediately prior to, or after, transfer of the substrate from the substrate preparation station to an analysis mount. The substrate analysis systems of the invention are capable of providing this functionality.

Controlling the temperature of the substrate while the substrate is being prepared for analysis is desirable, as the temperature of the substrate (and accordingly, reactants delivered to the substrate), can affect the stability of the reactants and/or cause the reaction to commence prematurely. To this end, the substrate preparation station optionally includes a substrate incubation station with associated thermal controller for maintaining the substrate (and reactants) at a desired temperature prior to being transferred to the substrate analysis mount, or upon returning to the substrate preparation station from the substrate analysis mount after a non-final analysis "run" has been completed. In one aspect, the incubation station can be programmed by a user of the system to carry out a "hot start" reaction, where one or more reaction components (e.g., a nucleic acid polymerase) become active only after prolonged incubation at high temperature (e.g., between about 90° C. and 97° C.).

As will be appreciated, certain substrate analysis applications benefit from iterative analysis of one or more substrates, where one or more substrates are cycled (typically, one substrate at a time) between the preparation station and the substrate analysis mount. Such cycling of substrates between the substrate preparation station and the analysis mount may be particularly useful for intermittent detection of analytical reactions as a means to collect reliable data from times during the reaction that are less or not able to be analyzed if detection is constant throughout the reaction. For example, certain detection methods can cause damage to reaction components, and such intermittent detection allows the damage to be avoided or at least delayed, thereby facilitating detection of the reaction at later stages. Further details regarding intermittent detection approaches can be found in United States Patent Publication No. US 2010/0075327 by Maxham et al. entitled "INTERMITTENT DETECTION DURING ANALYTICAL REACTIONS", the full disclosure of which is incorporated herein by reference in its entirety for all purposes.

VII. Substrate Analysis Mounts

The substrates of the invention are typically interfaced with the overall substrate analysis system through an appropriate mounting stage that secures the substrate, provides translational capability to the substrate, e.g., relative to the optical system, and optionally provides additional functionalities, e.g., fluidic interfaces, thermal regulation, e.g., heating or cooling, positional registration, and the like. The mounting stage may comprise the same location upon which the preparation processes occurred. However, in preferred aspects, the preparation and analyses will occur at different locations within the system, as such processes may require differing conditions, and it also may be desirable to avoid damaging or fouling of the analysis stage. The analysis and/or mounting stage will also typically include a positioning element that ensures proper positioning and/or orientation of a substrate upon the stage, for subsequent analysis. Such positioning systems can be keyed structures on the substrate that are complementary to a corresponding structure on the mounting stage. These can include simple structures, e.g., tooth/notch structures, truncated corner structures, or other distinctive and complementary structures. Alternatively, the keying elements can include electronic keys, such as metal contacts and associated electronic components on the substrate and mounting stage, that indicate when a substrate is positioned properly and in the correct orientation for subsequent analysis. Such key elements may be provided encoded for each substrate, e.g., through incorporated memory elements on the substrate, or through the position and orientation of electrical contacts, to indicate a specific substrate, e.g., lot number, etc. Such identification systems may provide an ability to ascertain whether a given substrate has been used previously, and to what effect. Typically, the mounting stage includes a well or recessed component configured to receive the substrate or the packaged, structure containing the substrate, e.g., a multiwell plate format, as well as a biasing mechanism, e.g., spring, clip or other mechanism, for forcibly retaining the substrate in a fixed position on the stage.

By way of example, a mounting stage typically includes a platform or holder having a mounting region or mounting regions that receive(s) the substrate. For example, a mounting region is typically disposed over an aperture in the platform that allows observation of the substrate from underneath. Also, a mounting stage typically includes structures that facilitate the positioning and alignment of the substrate on the platform. These may include, e.g., detents, ridges, recesses or wells, for positioning the substrate, and alignment structures such as pins, bevel structures, tabs, or the like, that correspond to a complementary structure on the substrate, e.g., holes or notches. As noted above, securing mechanisms may also be provided for locking the substrate in place, such as biasing mechanism, like a clip or a closable cover element. In particularly preferred aspects, a closable cover is provided that closes over the substrate in the mounting stage, and serves to better shield the substrate and the reactants therein contained, from adverse environment effects, such as excess light, oxygen, etc. Additional components may be provided on the mounting stage, such as a heating or cooling element (e.g., at least one heat source, heat sink, Peltier heater, or Peltier cooling structure), additional optical components, and other interfacing elements.

As noted elsewhere herein, the system also typically provides the capability of illuminating different portions of the substrate at different times. This capability provides a number of advantages. For example, where reaction systems are sensitive to damage from illumination, i.e., photobleaching or other photodamage events, then different portions of the substrate can be illuminated for periods that do not result in such damage. Likewise, where higher throughput or multiplex is desired, one may be able to increase the effective multiplex on a single substrate by interrogating different portion of the substrate with the same system, but at different times. In order to achieve this, the system is typically configured to illuminate different portions of the substrate at such different times, and this may be provided through the selectively controlled illumination profile of the system, e.g., using masks, apertures, filters or gratings, to illuminate a subset of the area of the substrate. Alternatively or additionally, the illumination system or the mounting stage/substrate, may be moved relative to each other in order to allow the illumination pattern to impinge upon a different portion of the substrate.

For example, in one aspect, the mounting stage may optionally be coupled to a translation system for moving the stage in two or three dimensions relative to the optical system. The translation system allows scanning of the entire array of signal sources on a substrate, as well as providing an ability to move the substrate toward or away from the optical system for, e.g., focusing, removal of the substrate, addition of components to the substrate, or the like. A variety of x-y-z translation systems are readily available. Additionally, robotic systems are readily available for automating the translation functions of the mounting stage in accordance with preprogrammed instructions. The robotic system can include the capability of rotating the substrate about the x, y, and/or z axes to "level" the substrate (e.g., to align the plane of the substrate with the focal plane of one or more optical signal detectors such that optical signals from each reaction region of the substrate are substantially uniformly focused on the one or more detectors). As will be appreciated, a similar translation system could be employed in controlling movement of the optical train, or components thereof, to result in a similar movement of the illumination patter over the substrate.

In one aspect, the substrate analysis mount is an improved hexapod stage based upon the Stewart platform concept. A Stewart platform typically consists of two plates, an upper mobile plate having six degrees of freedom (three, rotational and three translational) and a lower immobile base plate. The base plate and upper plate are connected by six mobile and extendable actuators (or "legs"). Each actuator typically consists of an upper portion and lower portion, with a piston-like cylindrical degree of freedom between each portion. The actuators are connected to the base plate and upper plate by joints, e.g., universal joints, at each end of each actuator. The length of the six actuators can be independently varied via relative movement of the upper and lower portions of each actuator. Thus, the position and orientation of the upper plate/platform (e.g., comprising a substrate of the present invention) can be accurately controlled depending on the lengths to which the six actuators are separately adjusted. Similarly, hexapod stages of the present invention enable an exceptional range of motion and can be accurately and easily positioned and oriented.

It will be understood that upper and lower "plates" or "platforms" such as those found in conventional Stewart platforms are not required in hexapod stages of the present invention. For example, rather than including a standard base plate, the six actuators may be attached (e.g., via a joint) to any underlying planar support structure or attachment points suitable for supporting the hexapod stage. Moreover, the upper portion of the hexapod stage can comprise a variety of structural and/or functional elements configured to receive and support the substrate, permit illumination of the substrate from above or below the substrate, permit detection of optical signals emanating from reaction regions of the substrate from above or below the substrate, maintain a constant substrate and/or stage temperature, deliver reagents to the substrate, provide non-actuator-mediated positional control of the substrate, comprise one or more components of the optical system, dampen or cancel out any movement and/or vibration within the analysis system, and the like.

Figures 7A, 7B:
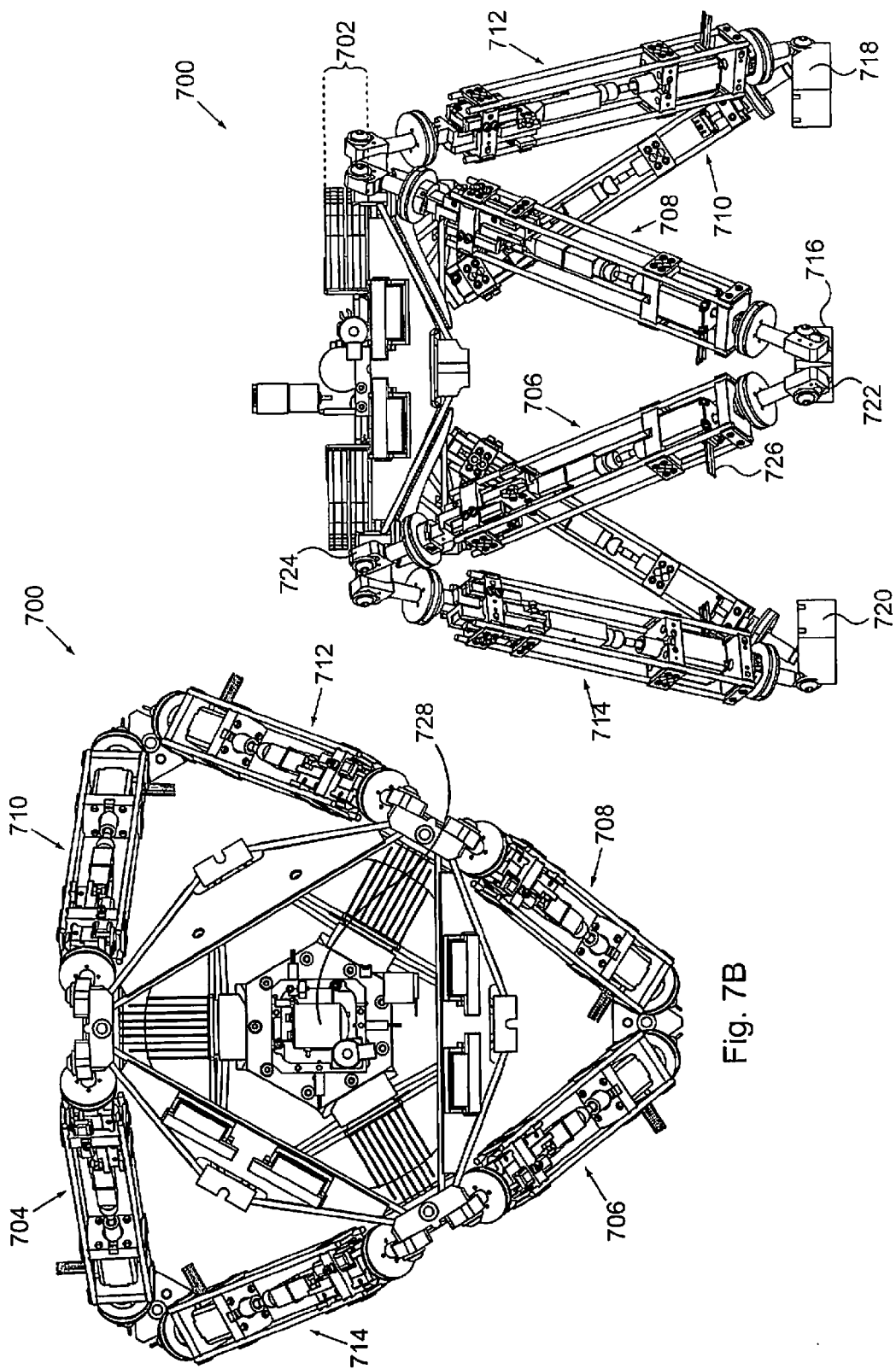
FIG. 7 is an illustration of one example of a mounting stage configured to receive and support substrates bearing signal sources for analysis in the systems of the invention.

A side view illustration of an example hexapod stage in accordance with the present invention is provided in FIG. 7A. As shown, hexapod stage 700 includes upper assembly 702 connected via six extendable actuators 704-714 to the substrate analysis system (e.g., via attachment points 716-720). Actuators 704-714 are connected to upper assembly 702 of the hexapod stage and attachment points 716-720 via joints, e.g., lower joint 722 and upper joint 724 with respect to actuator 706. In a preferred aspect, the actuators are motorized, where control electronics (in conjunction with one or more image-based algorithms and the focusing, leveling and/or alignment modules of the present invention) can send instructions to each motorized actuator, e.g., via connection 726 with respect to actuator 706, to decrease or increase in length. FIG. 7B illustrates a view of hexapod stage 700 from above. As shown, upper assembly 702 of the hexapod stage is configured to receive and immobilize substrate 728, which is optically accessible from above or below by illumination and/or optical detection components of the analysis system.

In general, the distance between the upper (mobile) and base (immobile) plates of a Stewart platform can change as the upper plate expands or contracts with changes in temperature or humidity. For example, illumination of an analysis substrate with excitation radiation can lead to undesirable thermal expansion of one or more elements in the upper portion (e.g., an upper assembly) of a hexapod stage. This change in distance between the upper and lower plates is generally undesirable, as it can affect the positioning of the substrate in applications where such changes in position are deleterious to data collection, e.g., collection of optical signals from reaction regions of the substrate.

In one aspect, hexapod stages of the present invention include athermal geometry to mitigate small changes in the distance between the upper and lower portions of the stage. In one embodiment, the athermal geometric configuration includes positioning the pivot points of each of the six actuators such that the plane containing the lines connecting the center of the upper portion (e.g., the upper assembly or plate) of the hexapod stage and the upper pivot point of the actuator is parallel to a line connecting the center of the upper plate and lower plates. In this configuration, the distance between the upper and lower portions of the of the hexapod stage will be invariant with small changes (such as those caused by thermal expansion) in the size of the upper assembly of the stage. As will be understood, the geometry of the hexapod stage (e.g., the positioning of the pivot points) can be varied to produce a desired relationship between the size of the upper portion and the distance between the upper and lower portions of the hexapod stage.

In addition to athermal geometry, or alternatively, one or more elements of the hexapod stages of the present invention are made of materials with low coefficients of thermal expansion. In one embodiment, carbon fiber composite rods (e.g., rods comprising carbon fibers and a polymer, e.g., an epoxy) are used for the length of the actuators. Such rods are inexpensive and have a very low coefficient of thermal expansion. With an appropriate combination of carbon fibers and epoxy, rods that have a zero coefficient of thermal expansion over a relatively small range of temperature can be achieved.

As noted above, hexapod stages of the invention optionally include a combination of athermal geometry and materials having low coefficients of thermal expansion to minimize sensitivity to thermal expansion. An example hexapod stage includes an upper assembly with a central portion that comprises aluminum (which has a relatively large coefficient of thermal expansion), and actuators with low coefficients of thermal expansion arranged in such a manner that any vertical shift caused by vertical thermal expansion is cancelled by a downward shift caused by a horizontal expansion of the upper assembly. The geometry inherently has a very low sensitivity to expansion and contraction of the top assembly, and expansion of the upper assembly does not cause a significant shift in the location of the center of the upper assembly.

As described herein, robotic systems also optionally include components that position substrates upon the mounting stage, apply reagents to the substrates, and the like. A wide variety of such robotic systems that may be applied to the present invention are generally commercially available from, e.g., Tecan, Inc., Caliper Life Sciences, Inc., Beckman, Inc., and the like.

VIII. Monitoring Systems

The substrate analysis systems of the invention include robotics for moving substrates, samples, reagents, applicators of samples/reagents, and the like, to and from various locations within the cabinet. It is therefore desirable to monitor and register the movement and locations of each of these system elements. Accordingly, the present invention optionally provides analysis systems that include monitoring systems, e.g., machine vision systems, disposed within the cabinet for tracking, controlling and registering information regarding the movement and position of system components.

Monitoring systems of the invention typically include one or more cameras with associated optics for acquiring images, a camera interface for providing images to a processing component (e.g., an embedded processor), machine vision software, one or more hardware modules (e.g., input/output hardware), and a communication link for reporting results to the primary control center of the analysis system.

IX. Optical Systems and Modules

A. Optical Trains

The substrate analysis systems of the invention typically include an optical train for the direction of excitation radiation to the substrate and the signal sources thereon, and/or for directing emitted signals from these sources to a detection system that quantifies and records the signal from each signal source. The optical trains used in the overall systems described herein typically include a number of different optical components for use in focusing, directing, splitting, separating, polarizing, and/or collimating the excitation radiation and/or the signals emanating from the discrete sources of signals. As used herein, optical trains can also include sources of optical energy, as well as optical energy detectors, e.g., one or more CCD or CMOS cameras, position sensitive detectors, and the like.

An example optical system of the invention is schematically illustrated in FIG. 8. FIG. 8A schematically illustrates the illumination system, objective lens and alignment system portions of the example optical system. As shown, illumination system 802 includes a first laser, e.g., red laser 804, which emits a beam of excitation radiation that is expanded by first beam expander 806. The beam from beam expander 806 is further expanded by second beam expander 808, and directed through a relay lens, e.g., adjustable effective focal length (EFL) relay lens 810, and into beam combining cube 812. A second laser, e.g., green laser 814, emits a beam of excitation radiation that is expanded by beam expander 816, and further expanded by beam expander 818 before entering beam combining cube 812. Subsequent to the expansion of the excitation radiation emitted from the red and green lasers, each expanded beam of excitation radiation can be divided into a plurality of beamlets, e.g., by one or more diffractive optical element (DOE). The red and green beamlets can be further divided by the same or different DOE. Optionally, a special chip and DOE layout are employed for separating the two colors. For example, the red beamlets can be turned off at one area of the DOE (e.g., the beamlets are not incident upon a particular portion of the DOE), and at a different portion of the DOE, the green beamlets are turned off.

Excitation radiation emitted from red laser 804 and green laser 814 exits beam combining tube 812 and, after optionally being split into a plurality of beamlets of excitation radiation (e.g., by one or more diffractive optical element(s) or other beam splitting component) enters objective 820, where the excitation radiation is reflected by dichroic 822 through a lens, e.g., calcium fluoride ($CaF_2$) lens 824, and onto substrate 826. Optical signals emanating from reaction regions disposed upon or within substrate 826 pass through $CaF_2$ lens 824 and are reflected upward or downward by dichroic 828 into an optical signal collection path (not shown in FIG. 8A for ease of illustration; see FIG. 8B). Backscattered excitation radiation emanating from substrate 826 passes through dichroic 822 and into alignment system 830. Alignment camera 832 detects the relative positions of laser spots and reaction regions (and/or micromirrors associated with reaction regions) on the substrate and facilitates the correction of misalignment between the laser spots and reaction regions. Alignment systems of the invention are described in detail below.

Figure 8A:
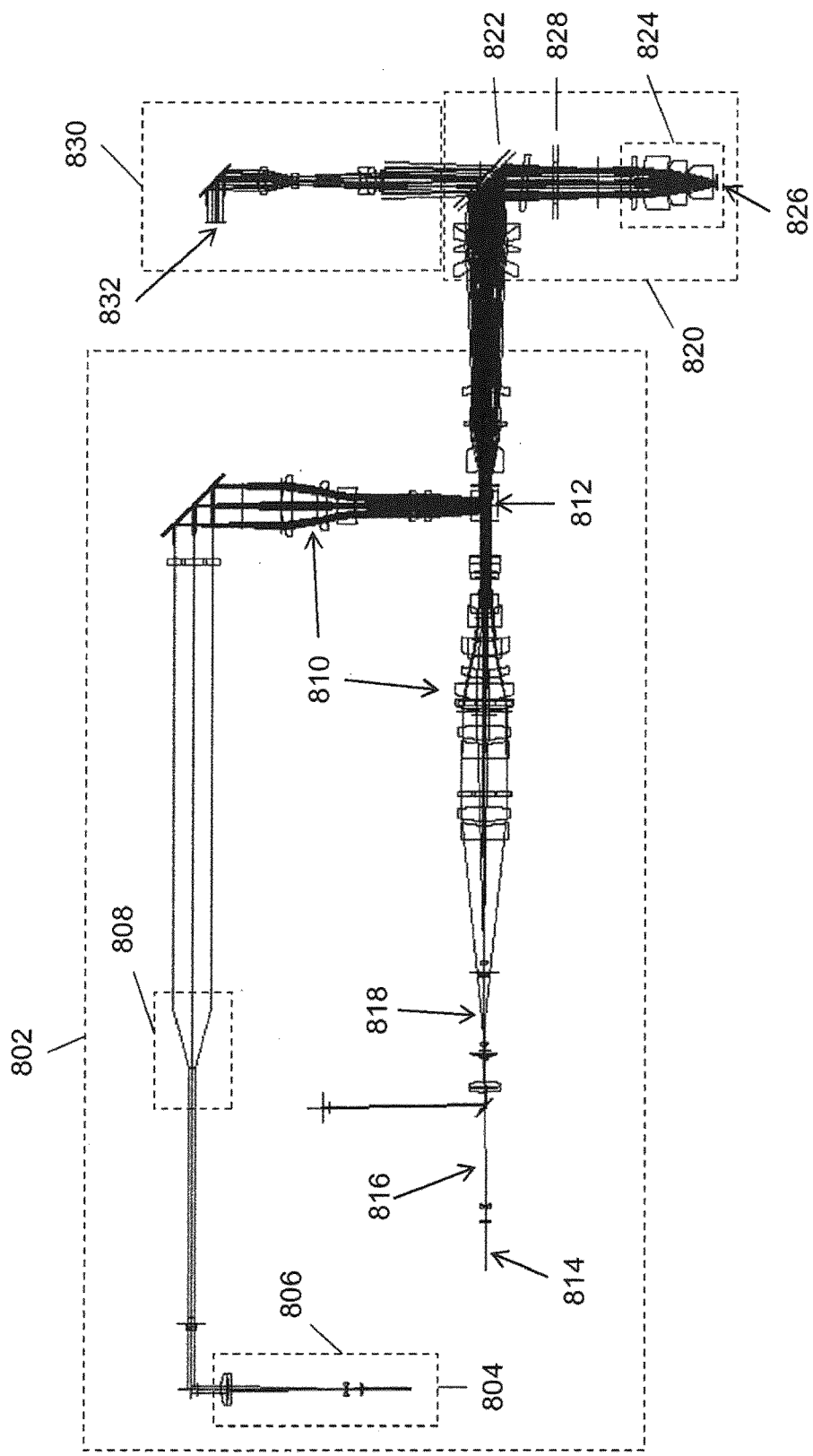
FIG. 8A schematically illustrates an example illumination system, objective lens and alignment system.
Figure 8B:
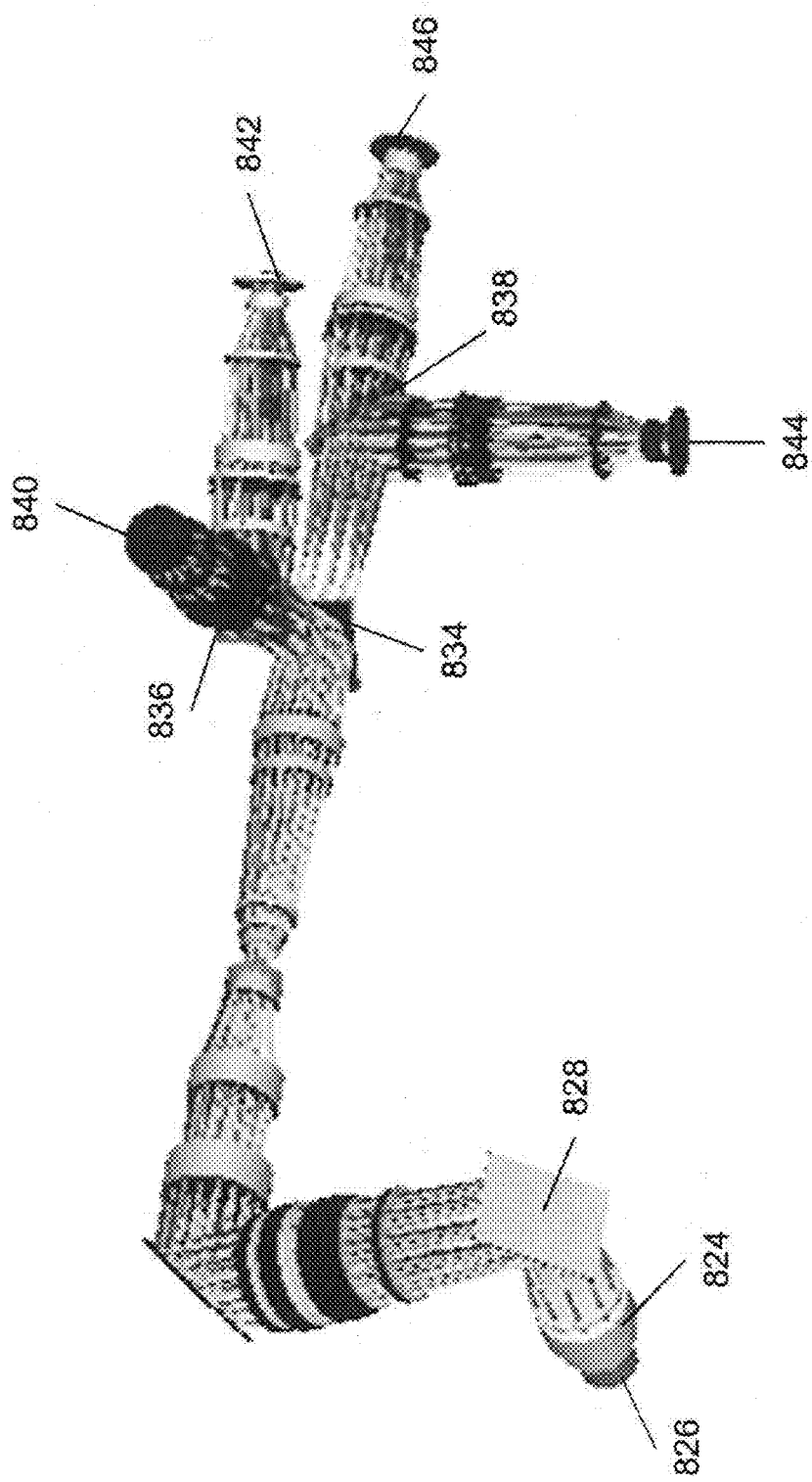
FIG. 8B schematically illustrates an example system for collecting and detecting optical signals emanating from a plurality of reaction regions on a substrate.

The collection path portion of the above example optical system is schematically illustrated in FIG. 8B. As shown, optical signals emanating from substrate 826 pass through $CaF_2$ lens 824 and are reflected upward by dichroic 828 for ultimate detection by one of four optical detectors, e.g., CMOS detectors 840-846, subsequent to color separation accomplished using a series of dichroic filters, e.g., dichroics 834-838. The dichroics and optical detectors are configured such that optical signals of a particular spectral range (e.g. a particular color) are detected substantially by one of the four optical detectors.

Figure 8C:
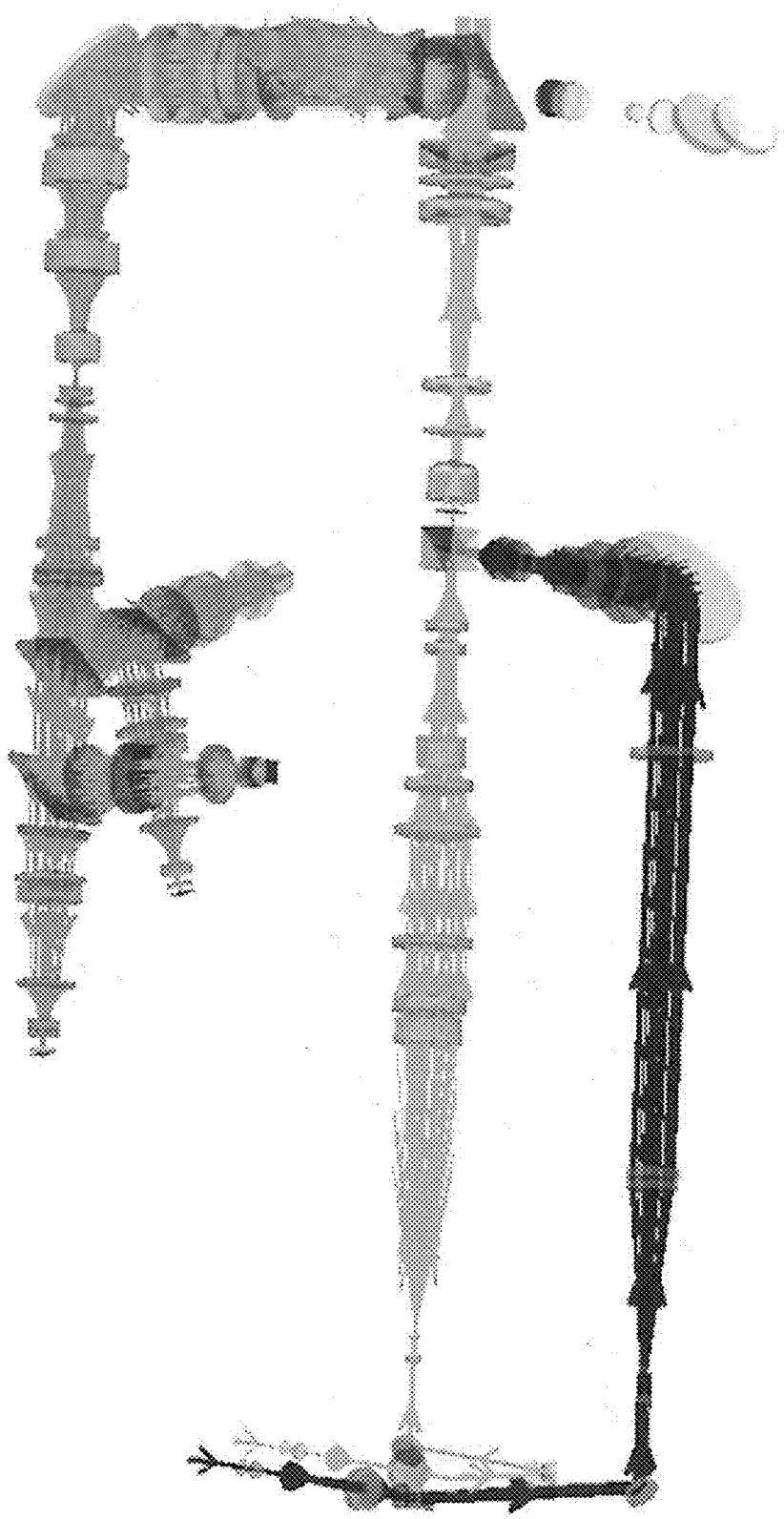
FIG. 8C illustrates the combined systems, lens and collection path of FIGS. 8A and 8B.

A combined view of the systems and collections paths shown in FIGS. 8A and 8B is provided in FIG. 8C.

Figure 8D:
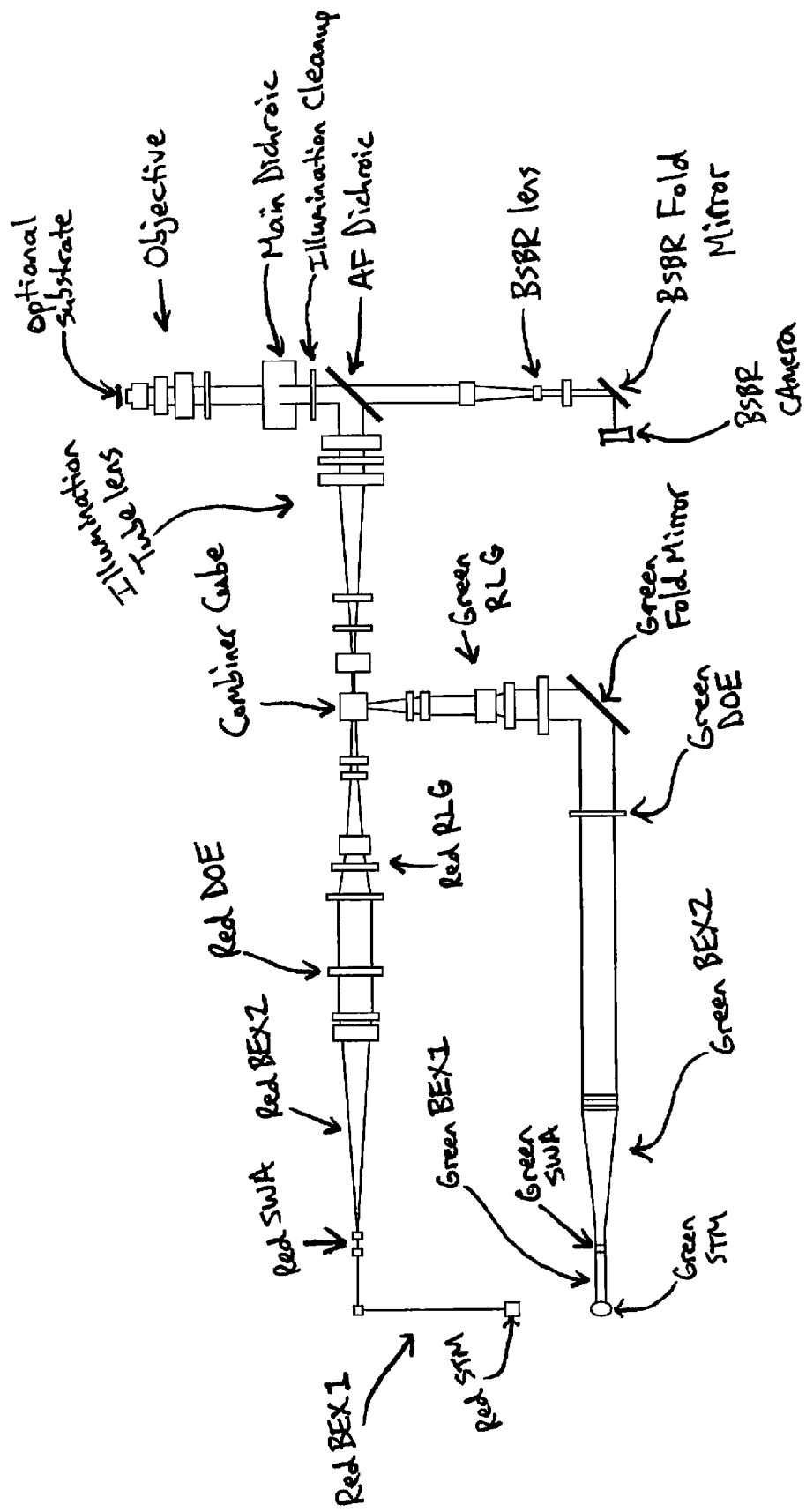
FIG. 8D illustrates an additional example optical system of the invention.

Another example illumination system, objective lens and alignment system is provided in FIG. 8D. "Red STM" and "Green STM" correspond to red and green lasers, respectively. The illumination path for each color includes a steering wedge assembly (SWA) comprising two prisms that can rotate independently to adjust the position of the laser beam. The alignment system can activate the SWAs when misalignment of the laser spots with the reaction regions on the substrate is detected by the alignment system. Diffractive optical elements (DOEs) are utilized to divide the expanded red and green laser beams into a plurality of beamlets. The plurality of beamlets pass through a relay lens group (RLG), which can be activated by the alignment system to focus the plurality of beamlets on the substrate. A tube lens is positioned between the objective and the combiner cube. As will be appreciated, any of the elements described above, e.g., SWAs, DOEs, RLG, tube lenses, and the like, can be present in other example systems described elsewhere herein, e.g., the example system shown in FIG. 8A.

Figure 9:
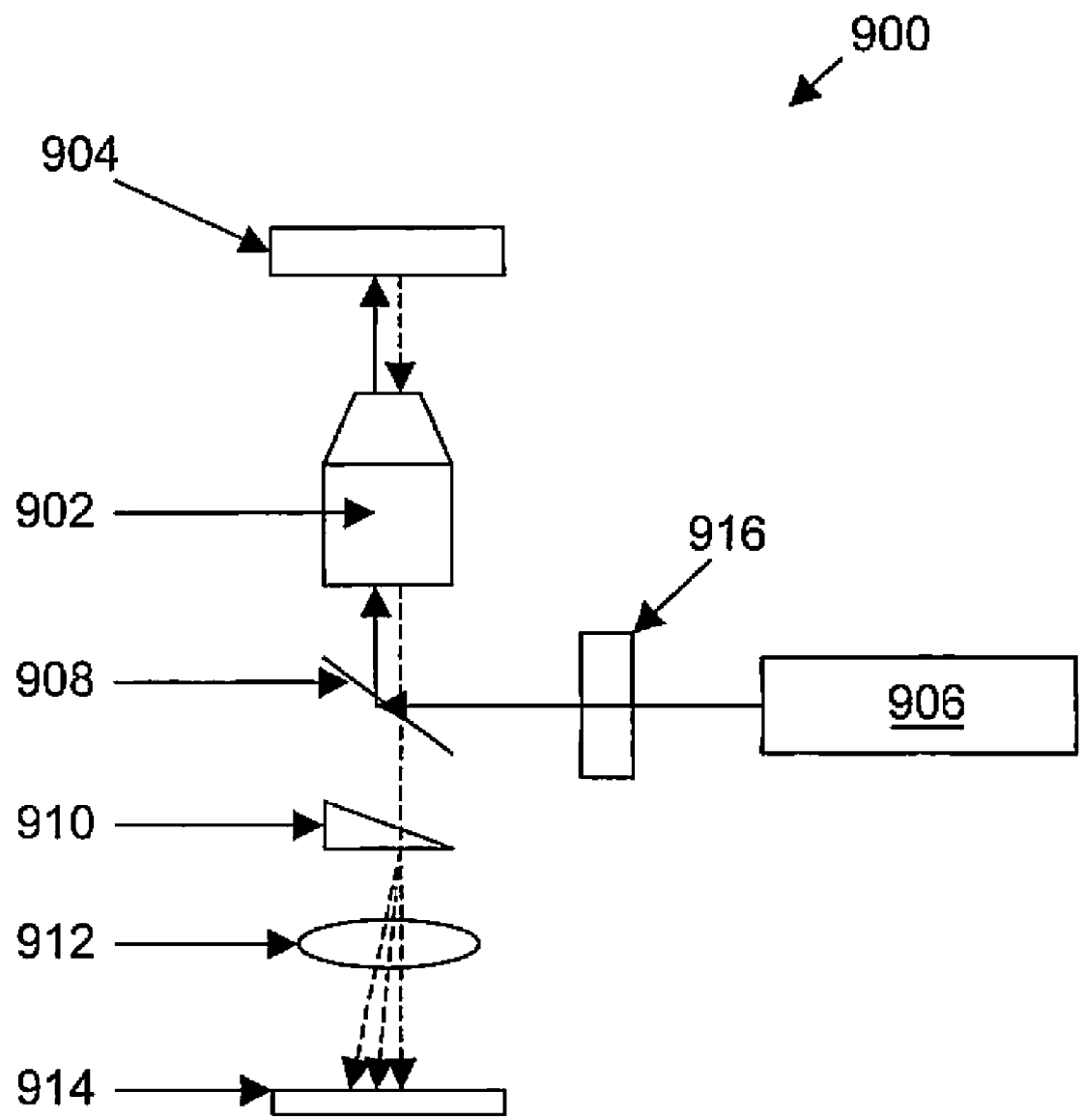
FIG. 9 schematically illustrates the substrate and optical train of the systems of the invention that includes optical componentry for the separation and detection of spectrally resolvable signal components.

A schematic illustration of an optical system is shown in FIG. 9. As shown, the optical train includes an objective lens 902 that is proximal to the substrate 904, and which focuses excitation radiation, e.g., from laser 906, upon a desired location of the substrate, and collects emitted optical signals from the substrate. The optical train will also typically include one or more dichroic mirrors/filters 908, that selectively reflect or pass excitation light and emitted optical signals, to effectively separate signal radiation from reflected or otherwise errant excitation radiation. It will be appreciated that a variety of optical configurations may be used in accordance with the systems described herein.

As noted previously, in preferred applications, the substrate analysis systems of the invention are used to monitor luminescent or fluorescent signals emanating form the plurality of discrete signal sources. As such, the systems of the invention include one or more sources of optical energy, e.g., one or more sources of excitation radiation. Excitation light sources will generally depend upon the nature of excitation radiation needed for a particular application, e.g., as dictated by the reagents and configuration of a given analysis. For example, the light source may include lamps, e.g., halogen, Mercury, Xenon, or the like, LEDs, lasers, laser diodes, or any other light source capable of directing electromagnetic radiation of a desired excitation wavelength or wavelength range, to the signal sources on the substrate. In preferred aspects, lasers are preferred as the excitation radiation source, due to the coherency and intensity of radiation that they generate in desired excitation wavelength ranges. A variety of different laser types are generally useful for these applications, and include, e.g., ion lasers, solid state direct diode lasers, diode-pumped solid state lasers (DPSS), solid state frequency converted crystal lasers, and the like. In some cases multiple sources may be employed in order to provide multiple different excitation wavelengths. By way of example, in cases where the signal sources include fluorescent compounds, e.g., compounds labeled with fluorescent dyes, multiple different excitation sources may be provided for the various different excitation spectra for such compounds. For example, in the case of compounds labeled with Alexa648 dyes, it will typically be desirable to provide at least an excitation source that provides excitation radiation range that includes light at 648 nm, the respective excitation wavelengths for these dyes, or if not provided at the nominal peak of the dye absorption curve, the lasers will include sufficient absorption efficiency for the dyes used, such as for Alexa546, where the peak absorption efficiency is closer to 561 nm. In the cases of multiple different dyes, different lasers, e.g., having different wavelength ranges may be used. To dissipate heat generated by the one or more optical energy sources, the optical train optionally includes one or more fluid cooling structures.

The optical train may also optionally include signal separation optics, e.g., to separate optical signals of different wavelengths or direct them to different locations on a detection system. For example, the optical train may include prism 910 that receives the optical signs as from the signal sources, that may include signals of several different primary wavelengths. Alternatively, sets of dichroic filters may be used in a cascading arrangement, to selectively direct each different spectral signal component to a different detector or detector region.

In the case of a prism as a separation element, upon passing through the prism 910, the different wavelength signals are diffracted to different degrees, and as a result, are directed, optionally through additional optical components, i.e., imaging lens 912, at different angles toward the detection system, e.g., detector array 914 allowing for their separate detection and quantitation.

The ability to separate such signals is of particular value in monitoring signal sources that include multiple different reagents that each have a different fluorescent emission spectrum, indicative of a different specific reagent, reaction and/or interaction. A variety of other optical components may be employed in spectrally separating the optical signals, including cutoff filter sets, dichroics, optical gratings, and the like. Such components will typically be arranged to direct different portions of each optical signal to different detectors or, preferably, different locations upon the same detector or array of detectors. In accordance with the invention, different signals may be spectrally resolved by differentially imaging such signal components onto the detector, e.g., detector array 914. Such differential imaging may be entirely spatially distinct, e.g., by being directed to different detectors or locations on the same detector, or they may conformationally distinct, e.g., providing an imaged signal that is of a different shape than an image of a different signal component, such that it can be resolved. For ease of discussion, both shall be generally referred to herein as being spatially resolved or separated or directed to different or regions of the detector, although in some cases, such different regions will be understood to overlap.

Other components that separate portions of the optical signals are also optionally included in the optical train, depending upon the application to which the system is to be put, including spatial filters, e.g., to confine the optical signals that are directed to the detector, polarizing filters, to pass signals that are in one polar optical plane, or the like. For example, in addition to separation of signals of differing wavelengths, the optical train may also include splitters, e.g., beam splitters, optical gratings, lens or microlens arrays, beam expanders (e.g., diffractive optical elements) and the like, that serve to divide up the excitation radiation and/or the emitted signals to direct it to different locations, or other optical components that change the spatial configuration of excitation radiation, e.g., optional optical grating 916. In some cases, additional filters may be added after the laser to filter the main laser line by removing or reducing any optical noise that may be inherent in the laser, as well as in front of the detectors to reduce or remove any unwanted stray light that may be generated or reflected from the system as a whole, or the ambient light.

Figure 10:
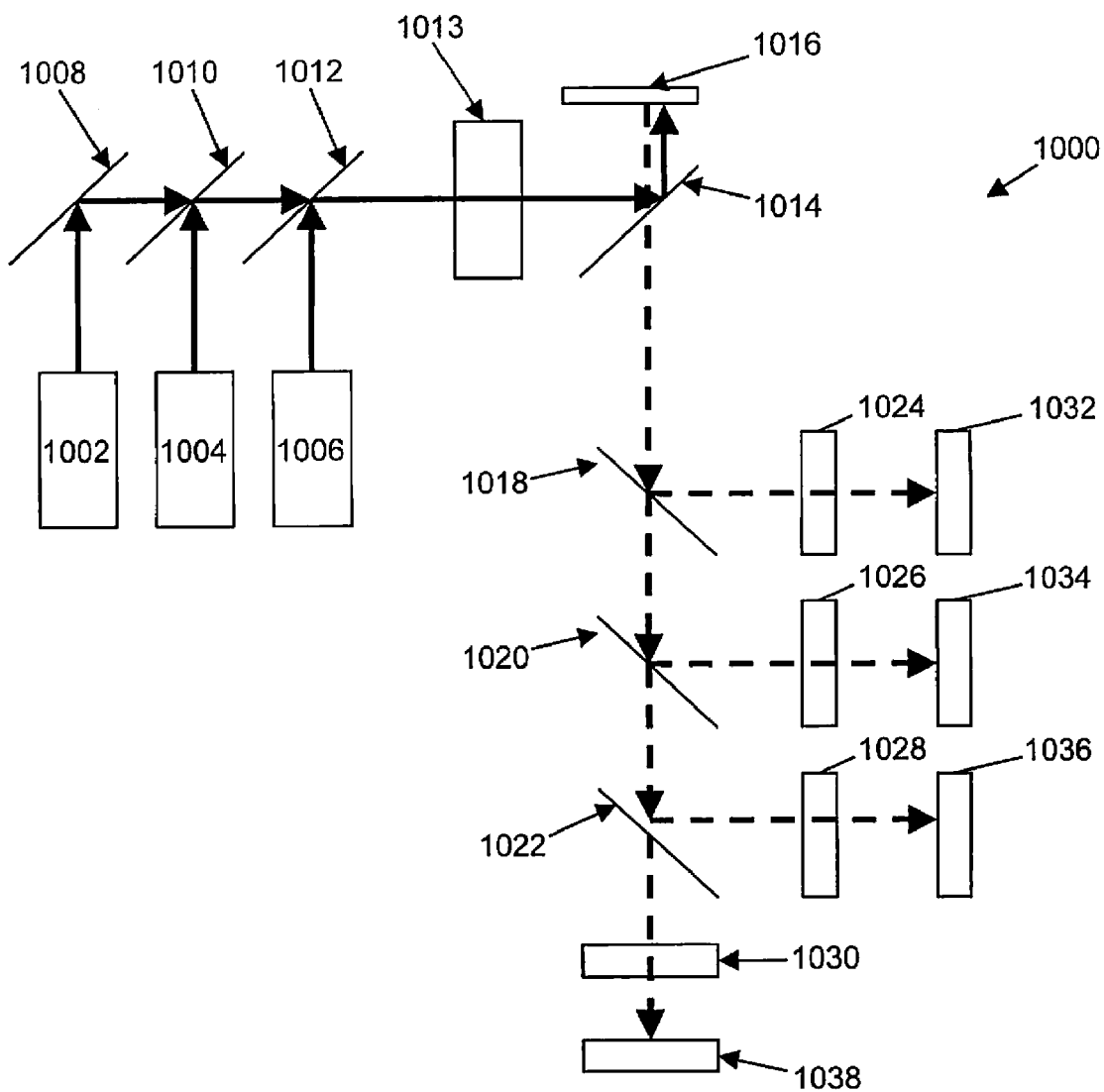
FIG. 10 provides a schematic illustration of a multiple excitation source/multiple emission wavelength system that utilizes transmissive fluorescence optics.

A schematic illustration of an example optical system in accordance with the invention is shown in FIG. 10. As shown, optical train 1000 includes at least a first excitation light source, e.g., laser 1006. For multi-band excitation, one or more additional light sources, e.g., lasers 1002 and 1004 are optionally included. Where such additional light sources are included, they are typically coupled with and directed at dichroic filters, e.g., dichroics 1008, 1010 and 1012, respectively, so that all of the excitation radiation from the various sources is co-directed, as indicated by the solid arrows. Optical system 1000 includes one or more multiplex components, such as diffractive optical element (DOE) 1013 (also optionally referred to as a holographic optical element or HOE), that converts the excitation radiation from the various sources to large number of discrete excitation beamlets (not shown for ease of illustration). As will be understood, the location and number of DOEs can vary, e.g., a DOE may be provided for each optical energy source. Having a dedicated DOE for each optical energy source can be preferable, as different spectra require slight variations in DOE design to achieve the same beamlet patterns. The beamlets of excitation light are then directed at a multiband dichroic filter 1014 that reflects substantially all of the excitation radiation at the substrate 1016 that is being subjected to analysis. Fluorescent signals emitted from the substrate or sample surface are then passed through the multiband dichroic 1014, which is transmissive to light at the wavelengths of the emitted fluorescence, along with some portion of reflected excitation radiation. As will be appreciated, optical trains that employ dichroics which are reflective to light at the wavelengths of the emitted fluorescence can also be employed. Optical trains which utilize reflective and/or transmissive dichroics in the direction of fluorescent signals have been described in, e.g., WO 2007/095119, the full disclosure of which is incorporated herein by reference in its entirety for all purposes. In the case of multiple different fluorescent emission spectra, the emitted fluorescence is then subjected to a color separation step, where the different individual emission spectra are separated from each other and separately detected. Color separation may be accomplished using a series of cascaded dichroic filters, such as filters 1018, 1020, and 1022 whereby a selected emission spectra is reflected from each of the dichroics onto adjacent detectors 1032, 1034 and 1036, respectively, with the last emission spectrum transmitting through all of the dichroics to be incident onto detector 1038. Alternatively, a prism based color separation process may be employed where different emission spectra are directed through an appropriate optical grating or prism to spatially separate the individual spectra and direct them to different detectors or different regions on an array detector. Additional filter elements, e.g., notch filters 1024-1030 may be included within the optical train to further tailor the emission radiation detected at each of the detectors, e.g., to filter out any inadvertent reflected excitation or emission light. As will be appreciated additional lasers, e.g., fourth, fifth, etc. lasers, may be included in the system with the concomitant inclusion of additional optical elements, e.g., filters, dichroics, etc. In a preferred embodiment, the optical detectors employed for data collection, e.g., detectors 1032-1038, are complementary metal oxide semiconductor (CMOS) detectors.

The various components of the optical train, e.g., lenses, gratings, filters, prisms, beam splitters, and the like, are generally obtainable commercially from optics suppliers, including, for example, Special Optics, Inc., Newport Corporation, Thorlabs, Inc., CVI Lasers, Lambda Research Optics, Lambda Physics, and Precision Optical, Inc.

B. Optical Systems for Enhanced Multiplex Illumination

In preferred embodiments of the substrate analysis systems of the invention, one or more of the optical train and/or the excitation radiation source may be configured so as to provide excitation illumination of a large number of discrete signal sources on the substrate simultaneously. In the case of arrays of zero mode waveguides, for example, the optical train and/or the excitation radiation source provide illumination to a large number of zero mode waveguides, simultaneously. As noted below, the optical trains are also typically capable of collecting and detecting signals from the same or similar large numbers of the signal sources, or in this example, zero mode waveguides. The systems typically illuminate at least 100 signal sources, simultaneously, preferably, greater than 1000 signal sources simultaneously, and more preferably, greater than 10,000 signal sources, simultaneously. In some cases, it may be desirable to use the systems described herein, for the excitation of 20,000, 50,000, 80,000, 100,000, 500,000 or more discrete signal sources. Systems that split excitation beams or apply multiple excitation sources (both with or without beam splitting) are useful for directing excitation radiation to larger numbers of signal sources.

Simultaneous illumination with excitation radiation over large numbers of signal sources can be accomplished through any of a variety of different approaches, as noted above. For example, one may focus a relatively large spot size upon a large array of signal sources. However, as will be appreciated, because laser power is limited, and indiscriminate illumination may cause certain adverse effects, e.g., heating of heat-sensitive reagents, or photo-damage of light-sensitive reagents, in some applications it is desirable to avoid illuminating non-signal generating portions of the substrate. Additionally, in many cases, the non-signal generating regions of the substrate optionally provide additional signal noise through reflection of the laser light. For example, in the case of arrays of zero mode waveguides using a thin film metal cladding layer, spaces between signal generating regions are highly reflective. Such reflected activation radiation gives rise to elevated signal noise levels for the system.

In some cases, larger excitation regions can be provided by directing multiple different excitation sources at a given substrate to provide illumination of larger numbers of signal sources. Unfortunately, use of multiple different sources may provide issues regarding differences between the individual sources, e.g., wavelength, frequency or intensity of illumination that may impact the signals resulting therefrom, e.g., rendering slightly different signal profiles. Additionally, such multiple excitation source systems may still give rise to the problems of excessive illumination of the substrate, as a whole. Similarly, excitation light beams may be divided into multiple beams, e.g., using beam splitters, optical gratings or other optical components, as alluded to above, to direct multiple discrete excitation illumination spots at different locations of the substrate, and as a result, illuminating larger numbers of signal sources thereon. In a related aspect, lenses may be provided that stretch the beam spot into an elliptical or elongated spot shape.

In certain preferred arrangements, individual or multiple excitation radiation source(s) may be manipulated to provide preferential illumination on the signal sources on a substrate, and reduce or eliminate illumination at regions of the substrate not occupied by the signal source(s). A number of methods may be used to modulate the illumination profile of the excitation light source to preferentially provide excitation illumination at the signal sources on the substrate, and, in particularly preferred aspects, less illumination at the spaces not occupied by such signal sources. In general, this is accomplished by using optical elements that provide a signal profile at the object plane of the optical train, e.g., the substrate, that peaks in intensity at positions in the object plane that correspond to the position of the signal sources on the substrate. A variety of different optical elements may be used to achieve this illumination profile. For example, where illumination at a low frequency is not an issue for analysis of the signal sources, one may simply employ reciprocating beam, e.g., through the use of a galvo-equipped laser system. In cases where low frequency illumination is or can be an issue, one may employ holographic or diffractive optical elements to achieve the desired illumination profile, e.g., in rows of lines, grids, or the like.

In certain aspects, cylindrical lenses or microlenses, or arrays of cylindrical lenses or microlenses are used to modulate the excitation light to provide illumination in a linear format so as to preferentially illuminate regions that include signal sources, and do not illuminate regions of the substrate that include no signal sources. Further, such optical elements may yield excitation illumination profiles on the substrate in multiple lines, i.e., in parallel and/or in orthogonal orientation, e.g., as a grid, or the like. For purposes of discussion, and with reference to direction at the substrate and included arrays of signal sources, the "laser spot" or "excitation radiation spot" refers to any of a variety of different beam shapes, configurations and orientations that are incident upon the substrate, including ellipses, lines, grids, and the like. As will be appreciated, when selectively directing excitation radiation at the signal sources on the substrate, the system may be equipped with certain alignment tools to facilitate alignment of the excitation radiation with the arrays of signal sources on the substrate. Such tools may include reference positions on the substrate that may be identified, either manually or automatically, by the system, to orient and/or focus the system appropriately on the array of signal sources on the substrate.

In illuminating large numbers of discrete regions on a substrate, e.g., using a diffractive optical element to provide discrete beams, ensuring adequate power is delivered to large numbers of illuminated areas typically requires increases in the power applied to the system. For ultra high multiplex systems, individual illumination sources for doing this are not commercially viable, due to cost and availability. For example, in certain exemplary applications, single illumination source beams are divided into beamlets that provide ~5 $\mu W/\mu m^2$. Achieving the same illumination power for 80,000 discrete spots would suggest a single illumination beam of ~500 mW.

In addition to laser issues, diffractive optical elements typically generate beam patterns that that have reasonable beam uniformity over relatively small fields of view. However, where one desires to expand the field of view, the non-uniformity of the illumination pattern can become excessive for certain applications. Thus, in expanding multiplex illumination, e.g., an order of magnitude or greater, one would expect substantial variation in illumination intensity across the illumination spots.

Accordingly, substrate analysis systems of the invention can employ multiple illumination sources and/or source beams that are directed through the diffractive element or diffractive elements in order to provide ultra high multiplex illumination with readily available, lower power illumination sources, and greater uniformity across the field of illumination. In one example, multiple illumination beams are directed through a single diffractive element at different angles in order to provide an output illumination pattern reflective of the multiple beams and angular variation in the originating beams. The multiple illumination beams can be directed at a diffractive optical element at different angles. The resulting pattern of illumination beamlets emanating from the DOE from each originating beam is directed upon the substrate in its own pattern, where each pattern is offset by a function of the angle difference between the two originating beams. Further details regarding multiplex illumination using multiple illumination sources with one or more diffractive elements can be found in International Application No. PCT/US2009/005319 by Zaccarin et al. entitled "ULTRA-HIGH MULTIPLEX ANALYTICAL SYSTEMS AND METHODS", filed Sep. 25, 2009, the full disclosure of which is incorporated herein by reference in its entirety for all purposes.

Alternatively or additionally, multiplexed optics and/or the substrate arrays may be configured such that at any given time, a subset of the reaction regions are illuminated. Following analysis of these regions, one or more of the substrate and/or optical system are adjusted to illuminate a different subset of regions on the array. Adjustment of the substrate or optical system may comprise actual movement of one or both of to substrate and/or optical train relative to the other, i.e., so that illumination pattern is directed at a different portion of the substrate. Alternatively, optical switches or masks may be employed to selectively redirect illumination from one portion of a substrate to another portion, e.g., through controlled direction optics, or through electronic masking approaches.

In configuring these systems, illumination can be directed at discrete blocks within an array, or at discrete rows/columns or individual regions. In one exemplary approach, arrayed reaction regions may be positioned within the array at one half the period of the array of illumination spots. Once the desired amount of data is collected from a subset of reaction regions, the array and/or illumination spots are then shifted one half period to illuminate the adjacent subset of reaction regions on the substrate.

As described previously herein, substrate analysis systems of the present invention optionally employ substrates comprising an array of micromirrors, wherein each micromirror is associated with a reaction region, e.g., a zero-mode waveguide. These substrates are particularly useful when very high multiplex analysis of reaction regions on analytical substrates is desired, and particularly for multiplexed systems for carrying out highly sensitive, low signal producing reactions, such as single molecule fluorescence analyses, e.g., as used in single molecule real time nucleic acid sequencing technologies. However, alignment of excitation radiation, e.g., laser spots, with the highly multiplexed reaction regions can be challenging.

The present invention provides substrate analysis systems for improved alignment of excitation radiation, e.g., beamlets of excitation radiation, with arrays of signal sources on the substrate. In one embodiment, systems of the invention include an alignment module which utilizes diffuse back illumination to align beamlets of excitation radiation with arrays of signal sources. Under diffuse light illumination, micromirror arrays can be detected as a microscopic-type image (as opposed to substrates employing "smooth" reflective surfaces which behave like a mirrors under diffuse illumination). In one aspect of the present invention, it has been discovered that capturing by a single optical detector a diffuse image of the micromirror array in addition to an image of laser spots (e.g., produced by beamlets of excitation radiation) enables tracking the relative movement between the laser spots and the substrate, as well as measuring the laser spot size and magnification.

Figure 11:
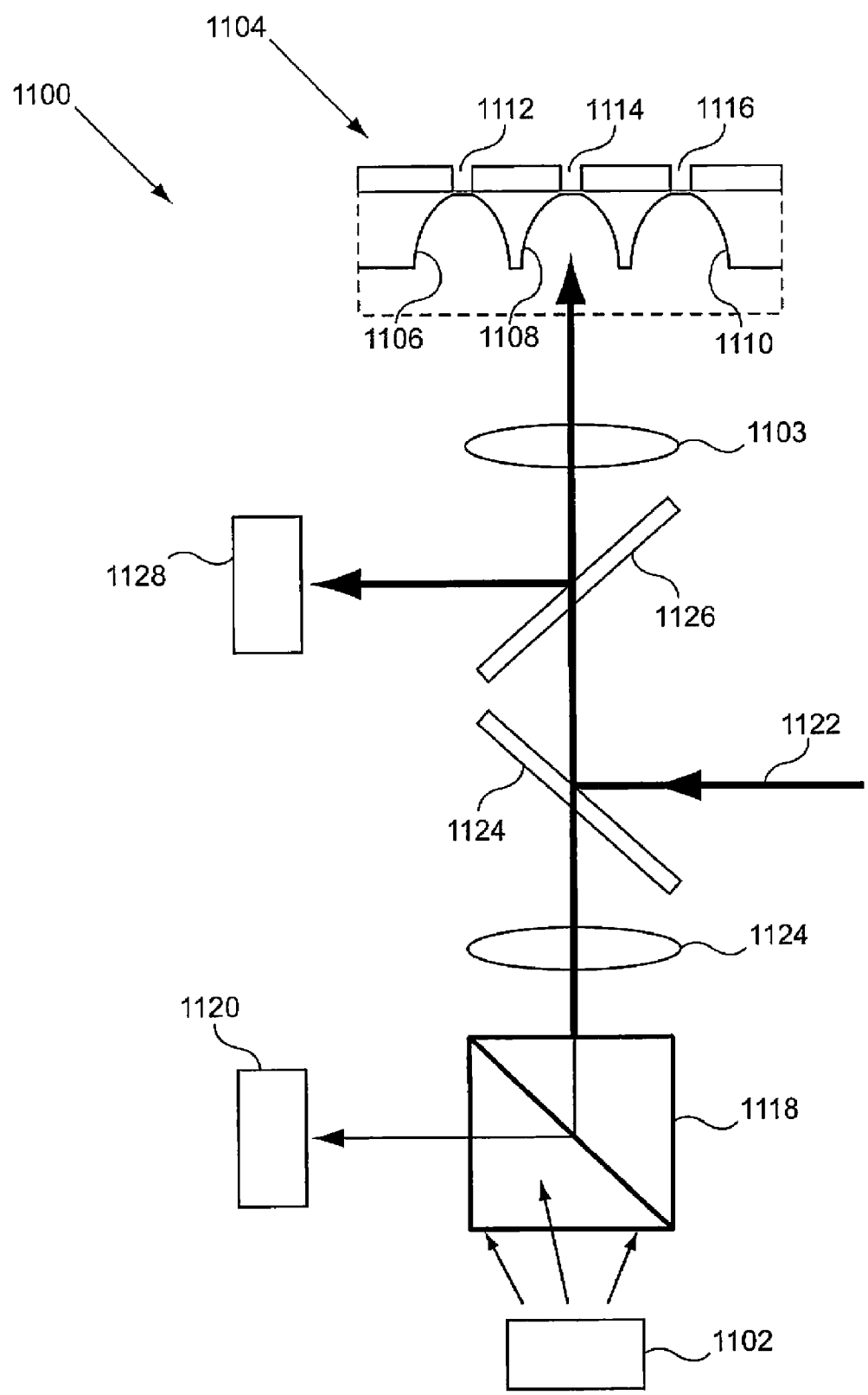
FIG. 11 schematically illustrates an alignment module of the invention which utilizes diffuse back illumination to align, and track the alignment of, beamlets of excitation radiation with arrayed signal sources.

An example system that utilizes diffuse back illumination to align, and track the alignment of, beamlets of excitation radiation with arrays of signal sources in accordance with the invention is illustrated in FIG. 11. As shown, alignment module 1100 includes diffuse light source 1102 which emits diffuse light through objective 1103 and directed toward substrate 1104. Disposed on substrate 1104 are one or more micromirrors, e.g., micromirrors 1106-1110, each micromirror disposed proximal to a reaction region, e.g., zero mode waveguides 1112-1116. Diffuse light reflected from substrate 1104 is reflected by beam splitter 1118 toward an optical detector, e.g., CCD camera 1120. To facilitate collection of diffuse back illumination and reflected excitation radiation, the alignment module optionally includes a lens, e.g., tube lens 1124 disposed between substrate 1104 and beamsplitter 1118. When excitation radiation of different colors is provided to the substrate, one or more bandpass filters can be placed between objective 1103 and tube lens 1124, e.g., to balance the signal-to-noise of the colors. For example, two bandpass filters can be placed between objective 1103 and tube lens 1124 when excitation radiation of two different colors (e.g., red and green) is provided to the substrate, e.g., as in FIG. 8.

Beamlet of excitation radiation 1122 is directed toward dichroic 1124 and reflected toward the substrate for illuminating zero mode waveguides 1112-1116. A single beamlet is shown for ease of illustration, although it will be understood that the invention can utilize two or more beamlets, e.g., thousands, tens of thousands, hundreds of thousands or more beamlets, to illuminate a corresponding number of highly multiplexed reaction regions on the substrate. Optical signals emanating from the reaction regions are reflected off of dichroic 1126 for collection by one or more optical detectors.

The diffuse back illumination and reflected excitation radiation utilized by the alignment module may, in some cases, be detected by a detection system that is distinct from that used to detect optical signals emanating from reaction regions of the substrate. In one aspect, optical signals emanating from the reaction regions are reflected by dichroic 1126 toward one or more signal detectors, e.g., signal detector 1128, while the diffuse back illumination and reflected excitation radiation utilized by the alignment module passes through dichroic 1126 toward other components of the alignment module, e.g., beam splitter 1118, for ultimate detection by camera 1120.

The alignment module is capable of performing an initial alignment (e.g., prior to detection and analysis of signals generated from the reaction regions), and also enables the monitoring of drift within the optical train that may occur while the analysis is in progress. Further, the module can measure the size of laser spots and diffractive optical element (DOE) pattern magnification. The alignment module can provide automated alignment, e.g., by including additional components (e.g., a computer processor, software, and the like) that compares the positions on the detector of optical energy from the one or more micromirror and the positions of the two or more beamlets of excitation radiation on the substrate, and in the event of suboptimal alignment or drift, instructs the relevant components of the optical train to adjust their positions and/or orientations to regain substantially optimal alignment (e.g., dynamic laser and/or optical system drift correction).

In a related aspect, the alignment system permits the tracking of laser focus drift. For example, the alignment system can monitor the reflection (e.g., backscattering) of beamlets at a surface corresponding to the upper portion of micromirrors on the substrate and at a reflective surface corresponding to the lower portion of micromirrors on the substrate. The two reflective surfaces enable the system to determine in which direction (e.g., +Z or –Z) the substrate has moved. In contrast, when only a single surface is monitored, a change in focal score does not indicate in which direction the substrate has moved. Accordingly, the alignment system that monitors two reflecting surfaces provides additional information with respect to the Z position of the substrate and provides improved laser focus drift tracking.

The alignment module provides a number of additional benefits, including obviating the need for alignment fiducials on the substrate, insensitivity to vibration in the substrate analysis system (due to the laser spots and diffuse images sharing a common optical path), the configuration of the module is relatively simple, continuous illumination is possible without causing, e.g., photodamage to reactants in the reaction regions, and the signal to noise ratio falls well within an acceptable range.

A variety of light sources to produce diffuse back illumination can be used in the invention. In one example, the light source is a near infrared light source (e.g., broadband near infrared LED) which has quasi-uniform angular emission profile. Preferably, a relatively flat area of the substrate will be used to reflect the excitation radiation and a neighboring substrate which contains the micromirror to generate diffuse back illumination reference for alignment. The relatively flat area is preferably located farthest from the center of the substrate surface allowed by the size of imaging sensor. The magnification of the alignment module and the camera resolution is selected such that the additional components (software) performance is optimized. For red-green color separation, an illumination mask configured to block certain rows or columns of each color can be used; alternatively, the DOEs for the red and green excitation layout can be configured accordingly such that at one flat area, only one of the two colors are present.

Figure 12:
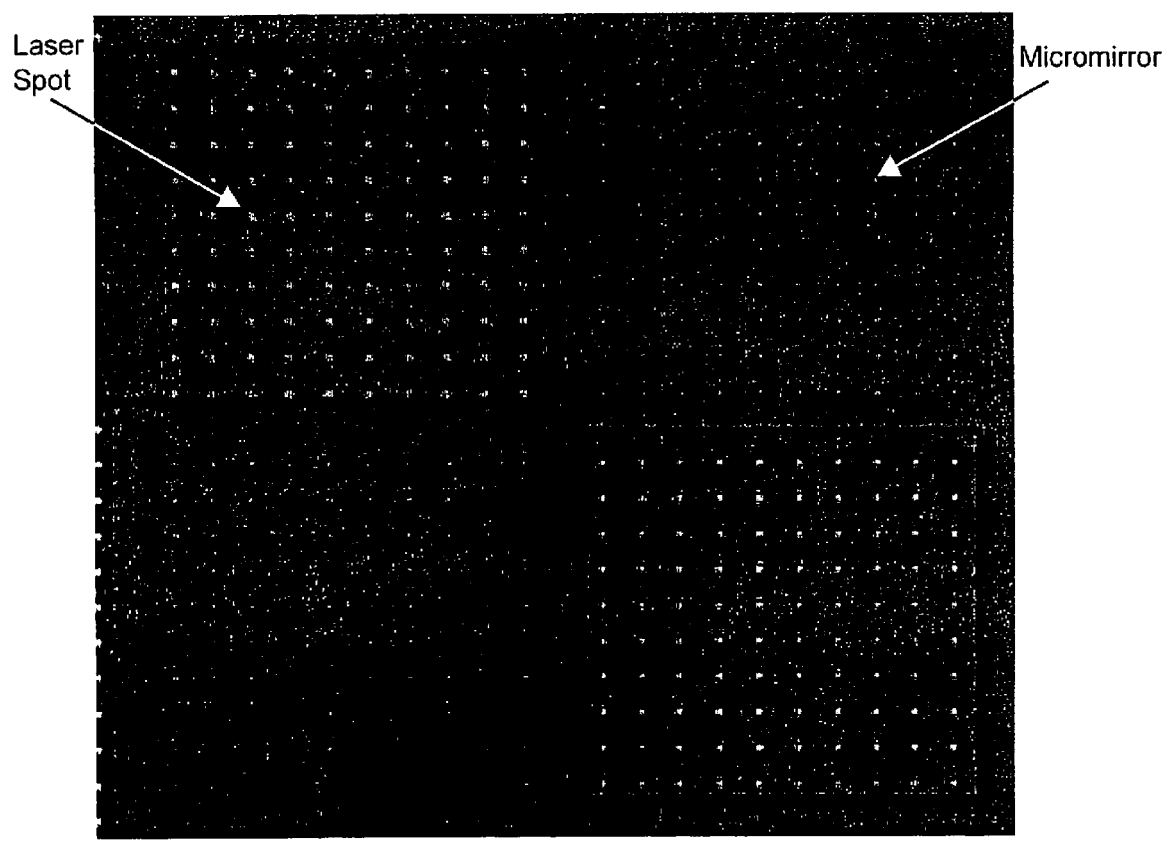
FIG. 12 is an image of laser spots and back illuminated micromirror arrays.

FIG. 12A is an image of a micromirror array under diffuse light illumination, as illuminated and detected by an alignment module of the present invention. FIG. 12B is an image of laser spots and back illumination captured by an EMCCD camera, wherein a 10× objective was employed in the optical train.

Figure 13:
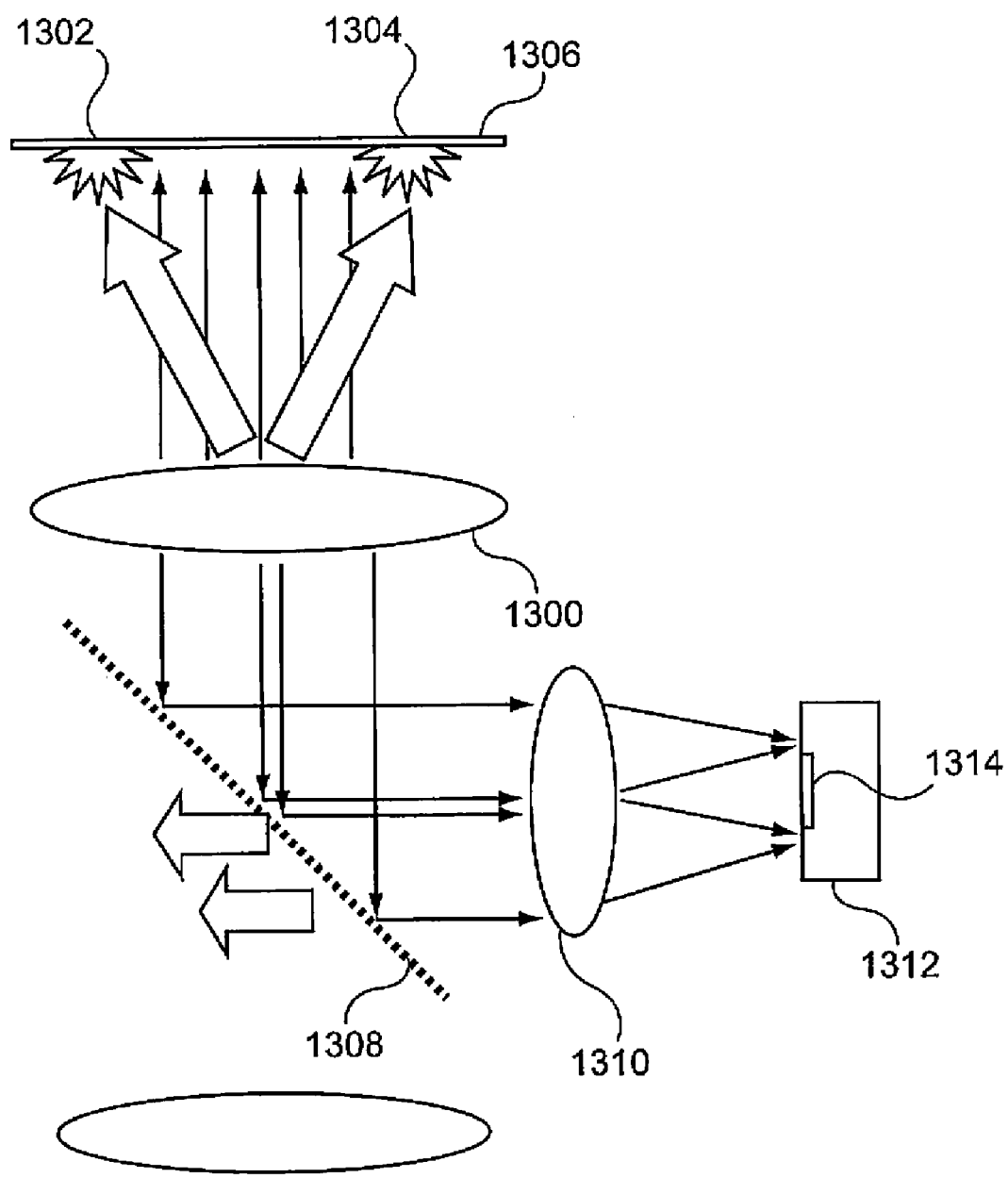
FIG. 13 provides a schematic illustration of an alignment module of the invention that images back scattered light from non-reaction region features of a substrate.

Modules for aligning arrays of laser spots to arrays of reaction regions on a substrate which utilize the same source of excitation radiation as is used for illuminating reaction regions on the substrate are also provided by the present invention. The benefit of using such alignment modules is that they obviate the need for separate illumination sources, the feedback signals are strong, and they afford high-speed detection with excellent signal to noise ratio. One such alignment module is configured to image back scattered light from non-reaction region features, e.g., fiducials, disposed within or upon a surface of the substrate, where the brightness of the image produced from the back scattered light is indicative of the alignment of the laser spots with the reaction regions. FIG. 13 schematically illustrates an example alignment module of the invention. As shown, optical energy passes through illumination objective 1300 and is targeted to non-reaction features, e.g., fiducials 1302 and 1304, located on the back of substrate 1306. Optical energy scattered back from fiducials 1302 and 1304 passes through illumination objective 1300 toward pickoff window 1308. The back scattered light is reflected off of pickoff window 1308 and directed through tube lens 1310 and onto an optical detector, e.g., CCD 1312. Aperture 1314, disposed between tube lens 1312 and CCD 1314, is configured to prevent the portion of the optical detector intended to detect optical signals emanating from reaction regions of the substrate from being exposed to the back reflected light.

Figure 14:
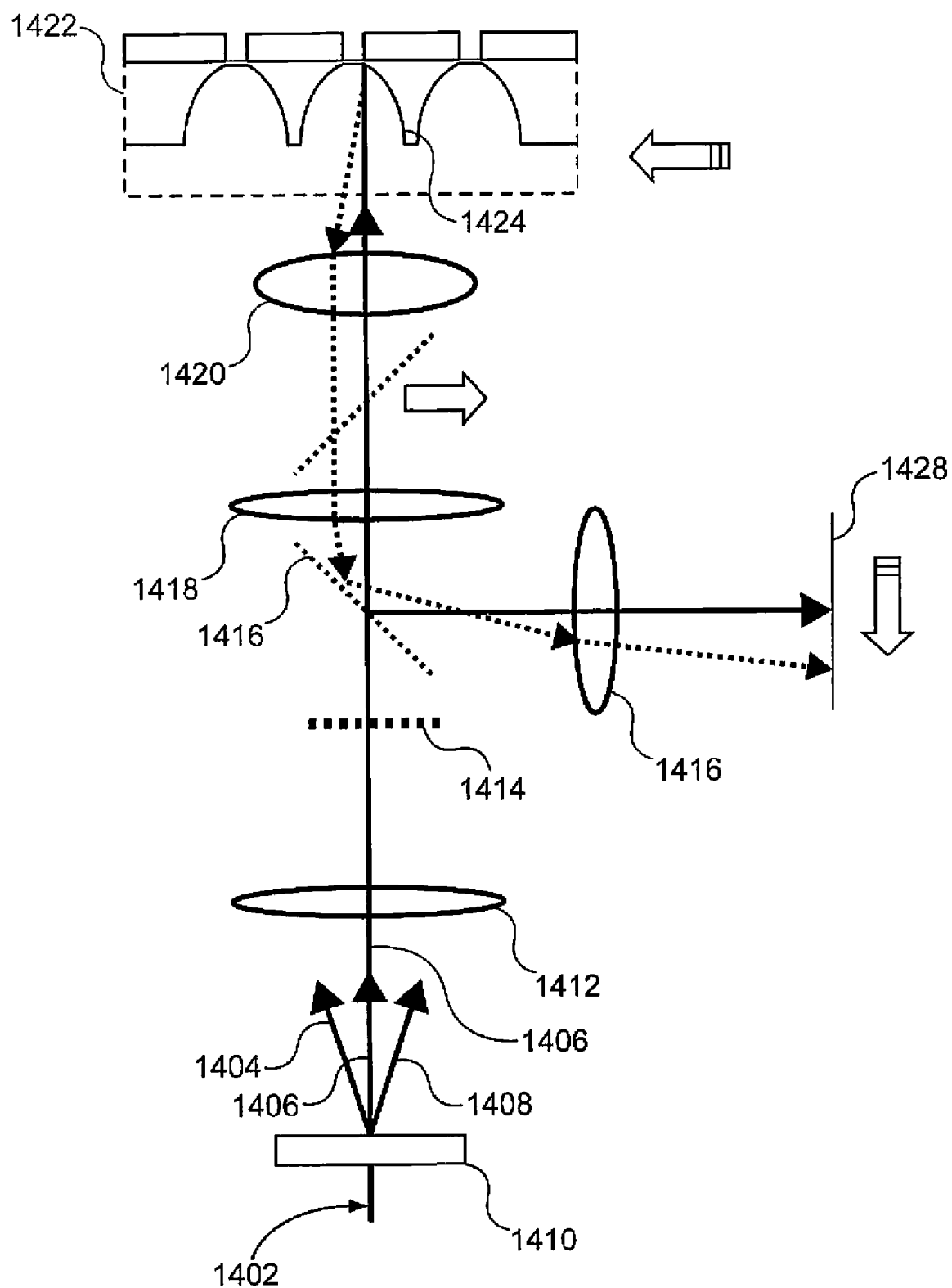
FIG. 14 schematically illustrates an alignment module of the invention that monitors the angular shift of back diffracted light from non-reaction region features of a substrate.

In a related embodiment, alignment of laser spots and reaction regions is monitored by measuring the angular shift of light diffracted back from non-reaction region features on the substrate. An example alignment module is schematically illustrated in FIG. 14. As shown, a beam (or more than one co-directed beams) of excitation radiation 1402 is divided into a plurality of beamlets, e.g., beamlets 1404, 1406 and 1408, by diffractive optical element 1410. For ease of illustration, multiple beamlets are not shown. Beamlets 1411 are directed through relay lens 1412, mask 1414, pickup window 1416, tube lens 1418 and objective 1420 toward substrate 1422. Beamlets 1411 are diffracted back from a feature on substrate 1422, e.g., micromirror 1424. The back diffracted light (clashed line) travels back through the optical train and is directed by pickup window 1416 through a lens, e.g., drift tracking lens 1426, onto an optical detector, e.g., CMOS 1428.

As shown, the angle of back diffracted light changes with the amount of misalignment between the laser spot and the diffraction feature on the substrate. By directing the back diffracted beam through a lens, e.g., drift tracking lens 1426 in front of an optical detector, e.g., CMOS 1428, the angular shift is translated into lateral motion of the image on the camera. By monitoring this lateral motion, the alignment module can track drift within the optical train and realign the beamlets of excitation radiation with the arrayed reaction regions if suboptimal alignment is detected.

In certain embodiments of the invention, an optical detector that detects back-scatter back-reflected (BSBR) optical energy from the substrate is used to align beamlets of excitation radiation with reaction regions disposed upon or within the substrate. The BSBR optical detector facilitates the precise tracking of the substrate and beamlet positions. However, distortion in the collection path of the BSBR optical detector can make it difficult to determine the correspondence of these features. Further, the correct co-registration of those features are highly sensitive to the particular configuration of the system and the search for the correct co-registration of those features is of quite high dimension (e.g., about thirteen).

The present invention provides an optional "fluorescence maximization" approach for aligning beamlets of excitation radiation with reaction regions of the substrate. When all beamlet shape and position characteristics are close to their nominal values and all beamlets are somewhat close to their optimal positions relative to the reaction regions, optimization of the excitation radiation delivered to the reaction regions is a convex problem. The fluorescence maximization approach involves the measurement of the illumination intensity at the reaction regions without using special hardware, by observing fluorescence signals returned to a data optical detector from a substrate filled with a large amount of fluorescent dye. Regions of the substrate which contain reaction regions without micromirrors can be used for this optimization to prevent complexity in interpretation of the results. As the search problem is convex, the problem of high dimensionality is mitigated; a simple iterative procedure can be used to determine the correct co-registration.

Because the above procedure can be used to set the optimal substrate and beamlet positions, correct correspondence between the features which track the substrate/beamlets and their corresponding physical motion does not need to be determined, and any errors which otherwise would be introduced by inaccuracies in such a calibration are removed. Thus, substrate to beamlet alignment can be achieved by any repeatable measure of position, rather than one which has a known exact correspondence to physical motion. Moreover, this approach provides for a very rapid alignment of the substrate and beamlets.

The present invention also provides substrates and illumination schemes for increasing the throughput of substrate analysis systems. As previously described herein, one approach for illuminating a plurality of arrayed reaction regions on a substrate is by directing a plurality of excitation radiation beamlets toward the substrate, where the beamlets are provided in a 1:1 ratio with respect to the arrayed reaction regions, e.g., each beamlet illuminates one reaction region of the array. One factor that limits the number of arrayed reaction regions that can be simultaneously illuminated is the pitch of the excitation radiation beamlet (e.g., the spacing between laser spots of excitation radiation at the plane of the reaction region array). In situations where the pitch of the reaction regions on the substrate (e.g., the distance between each reaction region within the array) can exceed the pitch of excitation radiation beamlets, approaches for increasing the throughput of substrate analysis are desirable. The present invention provides such approaches.

Figure 15:
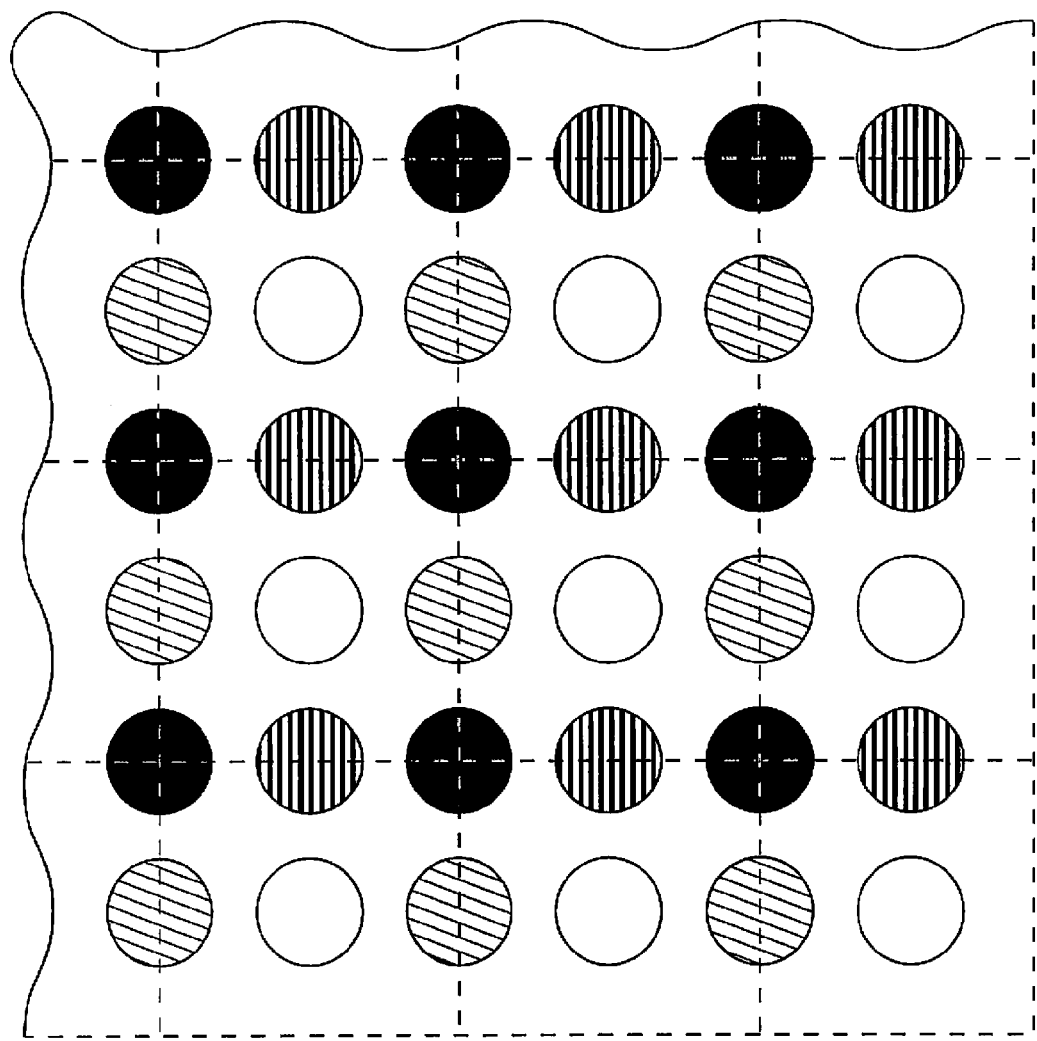
FIG. 15 provides a schematic illustration of reaction regions and illumination patterns for increasing the throughput of analysis systems of the invention.

In one embodiment of the present invention, reaction regions are disposed within the substrate at a pitch that is substantially one half the pitch of the excitation radiation beamlets incident upon the reaction region array (referred to herein as laser spots), and one out of every four reaction regions are analyzed during each analysis "run." By way of example, the pitch of the reaction regions, e.g., ZMWs, can be reduced from about 14×14 µm (the pitch in the X and Y axes of the substrate) to about 7×7 µm, whereas the pitch of the laser spots can be about 14×14 µm. The decreased pitch of the reaction regions is made possible by e.g., improvements in the design of the reaction regions and associated optical elements in the substrate. For instance, as described previously herein, providing a micromirror array in the substrate so that each reaction region (e.g., each ZMW) is associated with a micromirror results in decreased (or elimination of) cross-talk between optical signals emanating from the reaction regions and generally improved signal-to-noise ratios with respect to the collection of such optical signals This approach for increased analysis throughput is schematically illustrated in FIG. 15. The circles in FIG. 15 indicate the locations of reaction regions, e.g., ZMWs, disposed upon or within a substrate. The pitch and location of the laser spots is indicated by the portions of the grid where the dotted lines intersect. As shown, the laser spots in FIG. 15 are positioned to illuminate the reaction regions indicated by the solid circles. When the desired amount of data has been collected from the reaction regions indicated by the solid circles, the substrate and/or the laser spots can be repositioned such that the laser spots are aligned with a different set of reaction regions, e.g., the white reaction regions. The substrate and/or the laser spots can be repositioned such that the two remaining "sub-arrays" of reaction regions (e.g., those reaction regions indicated by the circles with vertical lines and the circles with horizontal lines) are analyzed, thereby completing four analysis "runs" on a single substrate. As will be understood, this approach for sequential analysis of sub-arrays of reaction regions can be varied. For example, the order in which the sub-arrays are analyzed can be varied.

In a related aspect, laser spots of substantially the same period as the reaction regions can selectively illuminate less than all of the reaction regions of an array, e.g., a cluster of about one quarter or more, about one third or more, about one half or more of the arrayed reaction regions. Once the desired amount of data is obtained from a first cluster of reaction regions, the substrate and laser spots can be repositioned relative to each other to permit illumination/analysis of a second cluster of reaction regions. This process can be repeated until the desired amount of data from all or substantially all of the reaction regions is collected. Further details regarding illumination and/or detection strategies that find use with substrate analysis systems of the invention are described in, e.g., United States Patent Publication No. US 2010/0075327 by Maxham et al. entitled "INTERMITTENT DETECTION DURING ANALYTICAL REACTIONS", the full disclosure of which is incorporated herein by reference in its entirety for all purposes.

The laser spots can also be repositioned (e.g., via movement of the substrate and/or optical train relative to one another) toward reaction regions from which data has already been collected, e.g., to collect additional or redundant data (e.g., additional and/or redundant nucleic acid sequence information), to enhance the quality of the analysis.

As will be appreciated, for any of the approaches described above (e.g., selectively illuminating reaction regions with a pitch less than that of the laser spots, selectively illuminating clusters of the reaction regions with laser spots of substantially the same pitch as compared to the reaction regions, and/or repositioning the laser spots to reaction regions that have been previously analyzed), the substrate can be removed from the analysis mount, moved to the substrate preparation and/or incubation station, and returned to the substrate analysis mount for analysis of a subsequent sub-array and/or cluster of reaction regions. Accordingly, multiple substrates can be alternately cycled between the analysis mount and preparation and/or incubation stations, with each cycle involving the analysis of the same or different populations of reaction regions on a given substrate.

C. Optical Systems with Compact Multi-Wavelength Illumination Architectures

In certain analytical systems that rely upon optical illumination and detection, it may be desirable to reduce the number of opto-mechanical assemblies required to perform the analyses. For instance, reducing the number of opto-mechanical assemblies can result in a more compact illumination architecture and, in the case of self-contained analysis systems where all of the components for carrying out the analysis are housed within a single unit, provides a more space-efficient analysis system and/or allows more space within a cabinet of the system to be occupied by other components of the system, e.g., computer hardware, substrate preparation/handling equipment, and the like. Moreover, conventional opto-mechanical architectures are susceptible to drift and misalignment from time-varying non-uniform thermal profiles over the entire architectural area.

The size and complexity of illumination architectures can be particularly relevant to analysis systems dependent upon multi-wavelength excitation radiation for generating optical signals. For example, certain applications require multiple lasers for the production of multiple beams of excitation radiation of different wavelengths. In such systems, it is often desirable to provide an illumination architecture that results in the multiple beams being combined into a co-directed multiple wavelength laser beam. One approach for generating a co-directed beam of this sort is by combining the separate single-wavelength beams using a series of dichroic mirrors. Using a series of dichroics requires multiple opto-mechanical assemblies for each laser source, which can have certain disadvantages, e.g., greater space requirement, potential increased susceptibility to drift and/or misalignment, and the like.

Figure 16:
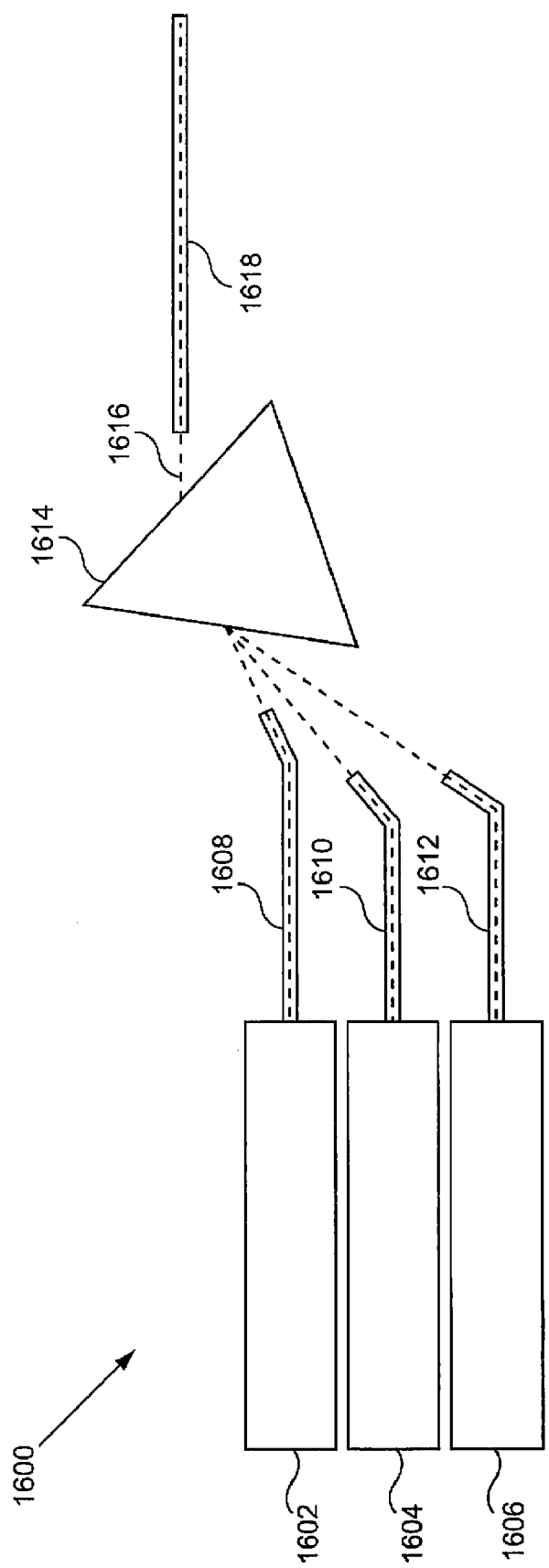
FIG. 16 is a schematic illustration of a compact multi-wavelength illumination architecture in accordance with the invention.

The present invention provides a compact multi-wavelength illumination architecture that significantly reduces the number of optical components necessary to illuminate a particular target (e.g., a substrate comprising an array of reaction regions), is more space efficient than conventional multi-wavelength illumination architectures, and can reduce the cost of manufacturing and operating optics-based analysis systems that are reliant upon multi-wavelength excitation. An example illumination architecture in accordance with the present invention is schematically illustrated in FIG. 16. As shown, two or more sources of excitation radiation, e.g., lasers 1602-1606 emit excitation radiation of different wavelengths through separate optical fibers 1608-1612, which excitation radiation is directed toward prism 1614. Prism 1614 is configured to combine the separate beams of excitation radiation exiting optical fibers 1608-1612 into a single collinear multi-wavelength beam of excitation radiation that travels through an optical fiber and is directed toward other optical components in the particular illumination path being employed.

D. Optical Systems for Enhanced Optical Signal Detection

Also provided by the invention are optical systems for enhanced detection of optical signals emanating from reaction regions of a substrate. Such optical systems can include, e.g., autofocus, alignment and/or leveling modules that monitor optical signals, or the location of the substrate relative to other optical system components, to provide optimal focus, alignment, and leveling prior to, and during, analysis of the substrate.

In one embodiment, a back scattered/back reflected (BSBR) autofocus module is provided that includes an optical energy source and a "non-data" optical energy detector (e.g. a camera that is not implemented to collect optical signals emanating from reaction regions of the substrate). In this embodiment, optical energy provided by the optical energy source is scattered/reflected at an interface between two layers of the substrate, e.g., the interface of a metal layer (e.g., an Al layer) and a transparent layer (e.g., a fused silica layer) where reaction regions are disposed proximal to, or at, the illuminated interface. The interface substantially corresponds to the location of signal sources within reaction regions (e.g., ZMWs) of the substrate. The non-data camera is configured to collect optical energy scattered/reflected back from the interface, such that information relating to the position of the interface is registered and utilized by other system components to focus the collection optics at the interface.

Substrate analysis systems designed to analyze highly multiplexed reaction regions on a substrate often employ a high numerical aperture dry microscope objective for collecting excitation radiation (e.g., arrays of beamlets generated by, e.g., a diffractive optical element) and directing the excitation radiation toward reaction regions on the substrate. High numerical aperture (N.A.) objectives are designed and optimized to work with cover glasses (e.g., substrates) of a certain thickness, and these objectives are highly sensitive to variability in substrate thickness. To accommodate for this variability, high numerical aperture objectives are typically equipped with a correction collar which can be set to compensate for aberrations introduced by thickness variations between substrates. However, changing the correction collar setting to accommodate variation in substrate thickness results in a slight change of the focal length of the objective, which introduces magnification error to the optical system. For most high N.A. microscopic applications, magnification error resulting from a change in the correction collar setting falls well within tolerable limits. However, in analysis systems that detect a plurality of signal sources from highly multiplexed reaction regions, even a small amount of magnification error can result in, e.g., beamlets generated by a diffractive optical element exhibiting a substantial position error in the illumination path towards the edge of the field-of-view, and optical signals emanating from reaction regions of the substrate not passing through an autofluorescence confocal mask in the collection path, and the like.

Certain autofocus systems of the invention utilize a laser beam that enters a high numerical aperture objective lens and reflects off of a surface (e.g., an aluminum surface of a zero-mode waveguide) near the focal plane of the lens. The reflected laser beam then travels back through the objective and lands on a detector, e.g., a position sensitive detector (PSD). The position of the laser beam on the detector correlates with the position of the reflective surface relative to the focal plane of the lens. This position signal provides a feedback to the optical system for focus tracking.

Figure 17A:
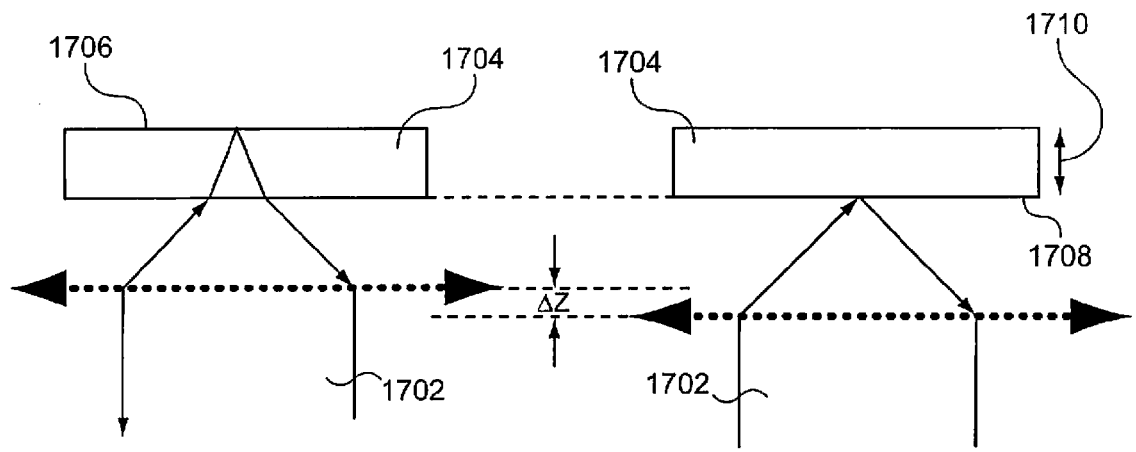
FIG. 17A schematically illustrates an autofocus module of the invention that determines the thickness of a substrate to maintain a constant system magnification and align the substrate to the focal plane of one or more signal detectors of the system.

The present invention provides autofocus modules, based on the autofocus system described above, for use in a substrate analysis system that precisely determine the thickness of the substrate and uses this thickness information to accordingly adjust optical components in the system to maintain a constant system magnification and align the substrate to the focal plane of one or more signal detectors of the system. An example autofocus system is schematically illustrated in FIG. 17A. As shown on the left, objective 1702 is first positioned within the optical axis at a distance from substrate 1704 such that optical energy reflects off of top surface 1706 of the substrate and is detected by an optical detector, e.g., a PSD, of the system. As shown on the right, objective 1702 is then positioned within the optical axis at a distance from substrate 1704 such that optical energy reflects off of bottom surface 1708 of the substrate and is detected by a PSD of the system. At each reflection surface, the autofocus system registers the Z position of the surface and measures the amount of travel between the two surfaces. The amount of travel, ΔZ, of objective 1702 is related to thickness 1710 of the substrate 1704.

Figure 17B:
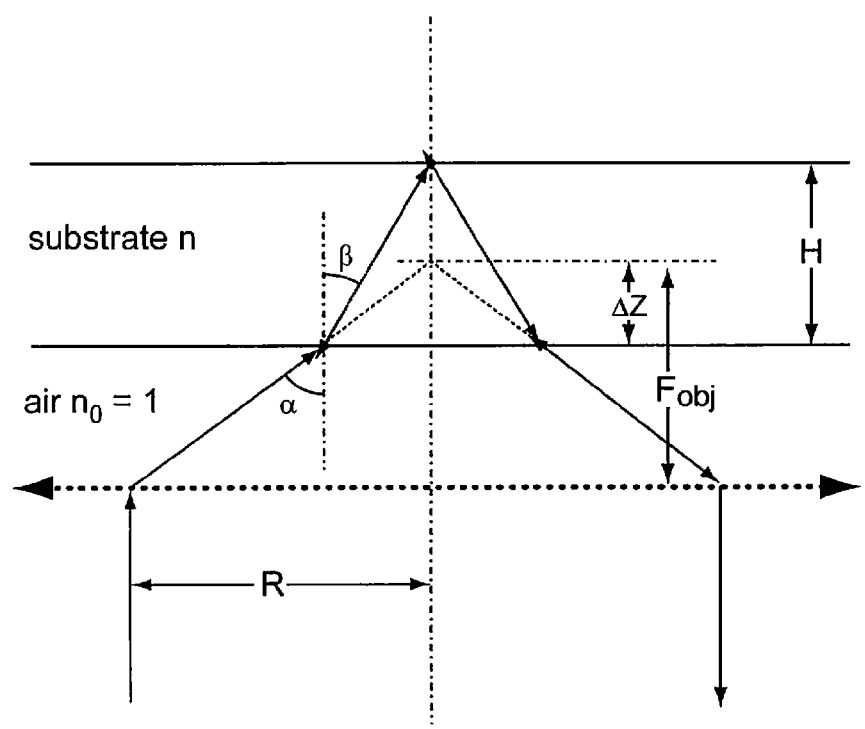
FIG. 17B illustrates the geometric considerations for determining the thickness of a substrate.

FIG. 17B illustrates the geometric considerations for determining substrate thickness. The geometric relations among the focal length of the objective ($F_{obj}$), the offset of the laser beam to the optical axis of the objective lens (R), the incident angle of the laser beam at the air-substrate interface (α), the reflective angle of the laser beam at the air-substrate interface (β), the distance the objective traveled between the two surfaces (Δz), the refractive index of the substrate (n) and the substrate thickness (H) are:

$$\mathrm{Sin}\ \alpha = n\ \mathrm{Sin}\ \beta$$

$$\mathrm{Sin}\alpha = \frac{R}{\sqrt{R^2 + F_{obj}^2}}$$

$$H \cdot \tan(\beta) = \Delta Z \cdot \tan(\alpha)$$

From the above equations, we may arrive at:

$$H = \sqrt{(n^2-1)(R/F_{obj})^2 + n^2} \cdot \Delta Z$$

When the refractive index of the substrate (n), the offset of the laser beam to the optical axis of the objective lens (R), and the focal length of the objective ($F_{obj}$) are kept constant, the distance the objective traveled between the two reflective surfaces (Δz) provides a measure of the thickness of the substrate.

In an autofocus system, laser spot movement at the PSD (L) and the reflective surface movement (Δz') follow the relation:

$$\frac{L}{\Delta z'} = 2\frac{F_{PSD} \cdot R}{F_{obj}^2} \qquad \text{Equation 2}$$

where $F_{PSD}$ is the focal length of the lens in front of the PSD in the autofocus system.

Combining equation 1 and 2 provides:

$$H = \sqrt{(n^2-1)\left(\frac{L}{\Delta z'} - \frac{F_{obj}}{2F_{PSD}}\right)^2 + n^2} \cdot \Delta Z \qquad \text{Equation 3}$$

Figure 17C:
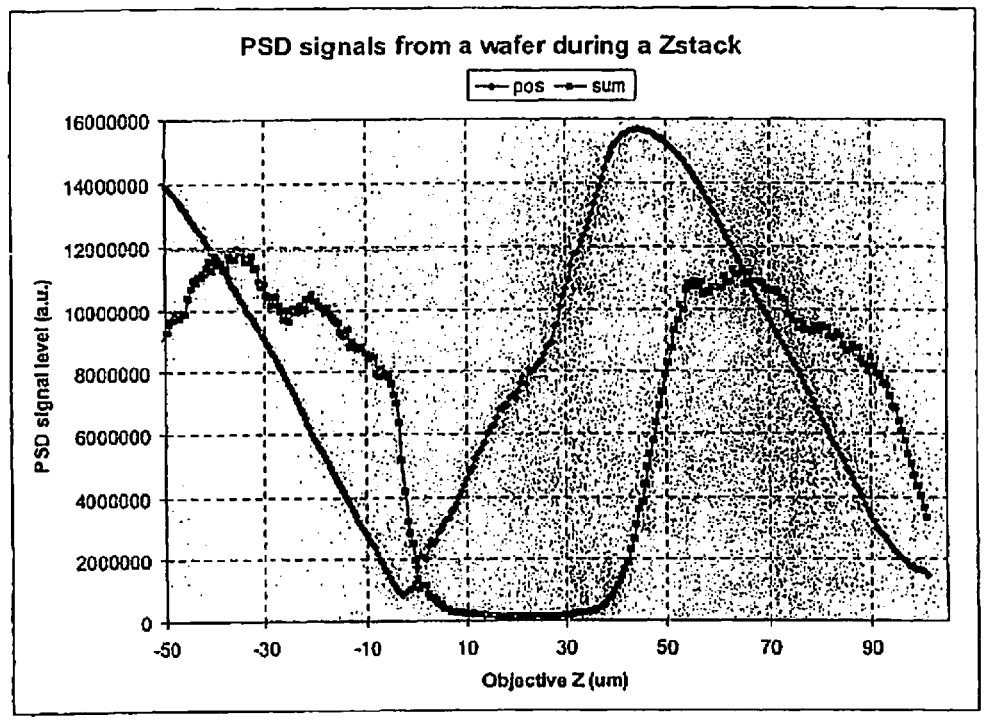
FIG. 17C shows a plot of PSD signals from a substrate during a Z stack acquired by an autofocus system of the invention.
Figure 17D:
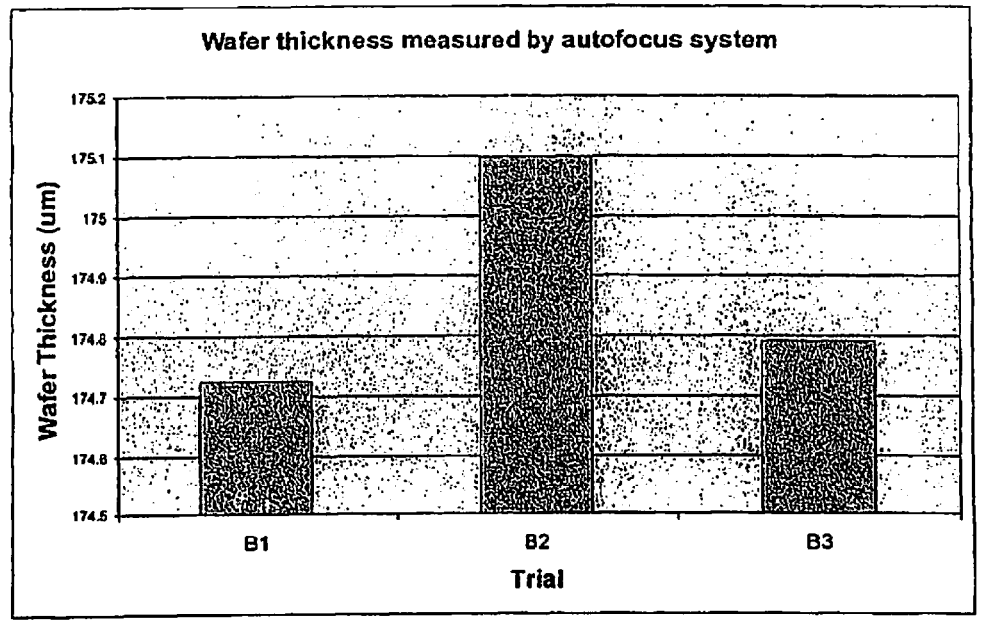
FIG. 17D shows a bar graph of substrate thicknesses calculated using an autofocus system of the invention.

PSD signals from a substrate during a z stack were acquired using the modified autofocus system of the invention and are provided in FIG. 17C. The two downhill slopes correlate to the laser sweeping across the PSD, as it reflects off of the bottom and top surfaces of the substrate. By tracking the mid-crossing points (8000000 in the y axis) of these two downhill slopes, Δz can be determined. The ratio of L to Δz' can also be determined from the slope of these two downhill slopes. Given n=1.4535, $F_{PSD}$=200 mm and $F_{obj}$=3 mm, substrate thicknesses were calculated for three repetitive measures using Equation 3, the results of which are shown in FIG. 17D.

Figure 18:
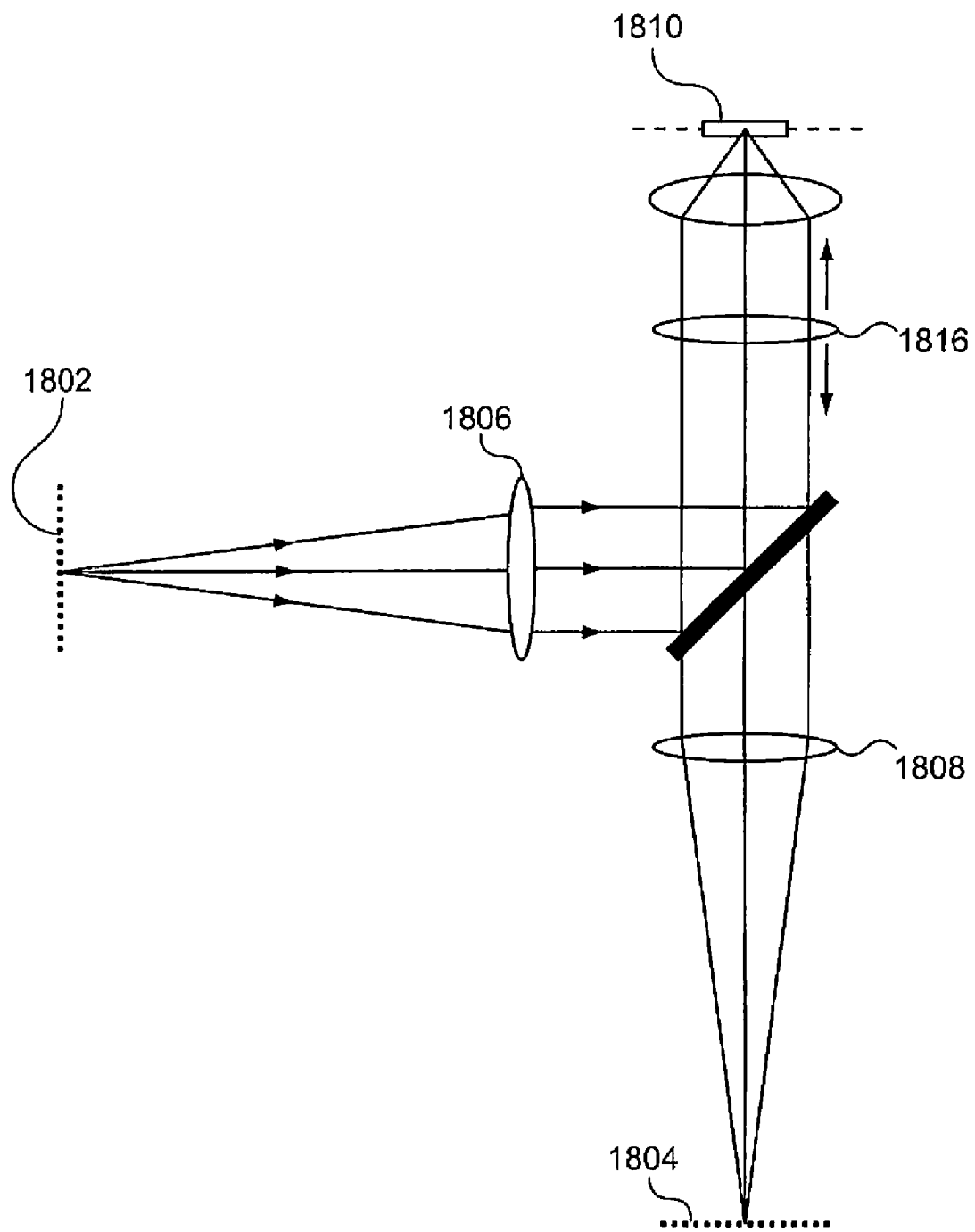
FIG. 18 provides a schematic illustration of an optical train that includes a lens for maintaining constant magnification within an optical system of the invention.

In one aspect, the present invention provides additional optical train configurations for preventing magnification error that can result from adjusting a high N.A. objective correction collar setting to accommodate for variability in substrate thickness. An optical train in which these configurations are particularly useful is illustrated in FIG. 18. The basic principle is that when the system is well aligned and the substrate thickness is equal to the specified thickness of the objective, both illumination pattern 1802 and mask 1804 will be on the back focal plane of their respective tube lenses (e.g., tube lenses 1806 and 1808, respectively), and substrate plane (e.g., a surface of the substrate where reaction regions are disposed) 1810 is on front focal plane 1812 of objective lens 1814. In this condition, the magnification will be equal to the focal length ratio of the tube lens to the objective. However, for cover glass thickness other than specified, the substrate plane will be out of the focal plane, constituting one source of magnification variation. When the substrate thickness changes, the correction collar setting of the objective is used to compensate for aberrations introduced by the cover glass thickness variation. However, the variation of the correction collar setting will alter the focal length of the objective, constituting a second source of magnification variation.

In one embodiment, the invention provides optical trains where inserting and/or moving a weak lens between the objective and a tube lens enables maintenance of constant system magnification. When the substrate thickness changes, the correction collar setting is adjusted. The focal length variation of the objective is compensated for by inserting weak lens 1816 between objective 1810 and tube lenses 1806 and 1808 in both the illumination and collection paths. Because the focal length variation is small, the inserted lens is weak. To compensate for the focal length variation caused by different substrate thicknesses, the inserted lens can be moved axially. In an alternative embodiment, a lookup table of the inserted lenses and the corresponding cover glass thickness can be built, and the corresponding lens for a given substrate thickness can be inserted.

Figure 19A:
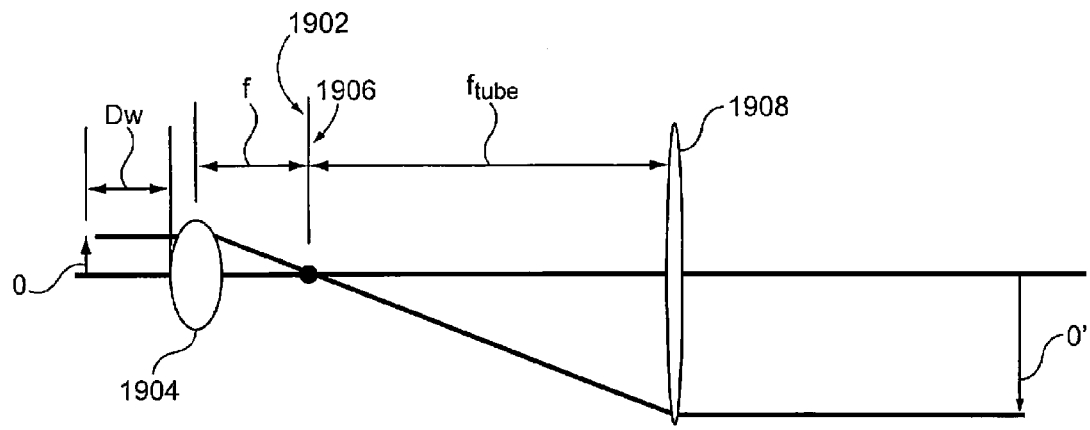
FIG. 19A is a schematic illustration of an optical system that is aligned to meet the afocal condition for maintaining constant magnification within an optical system of the invention.

In a related embodiment, the optical system is aligned to meet the afocal condition. Most high NA infinity corrected microscopes are relatively insensitive to the separation between the objective and the tube lens. However, if this separation meets the afocal system condition (e.g., the back focal plane of the objective coincides with the front focal plane of the tube lens), the system magnification remains constant even when the working distance ($D_w$) changes, and the magnification is always equal to the ratio of the focal lengths of the tube lens and the objective. Therefore, if there is no correction collar setting for the objective, even if the cover glass thickness varies (e.g., a change in working distance), the system magnification remains constant. A condition of this method is that the substrate thickness variation is small enough that the aberration resulting from the variation is within the tolerance. An optical system aligned to meet the afocal condition is schematically illustrated in FIG. 19A. As shown, back focal plane 1902 of objective 1904 coincides with front focal plane 1906 of tube lens 1908, and system magnification will not change in the presence of substrate thickness variation.

Figure 19B:
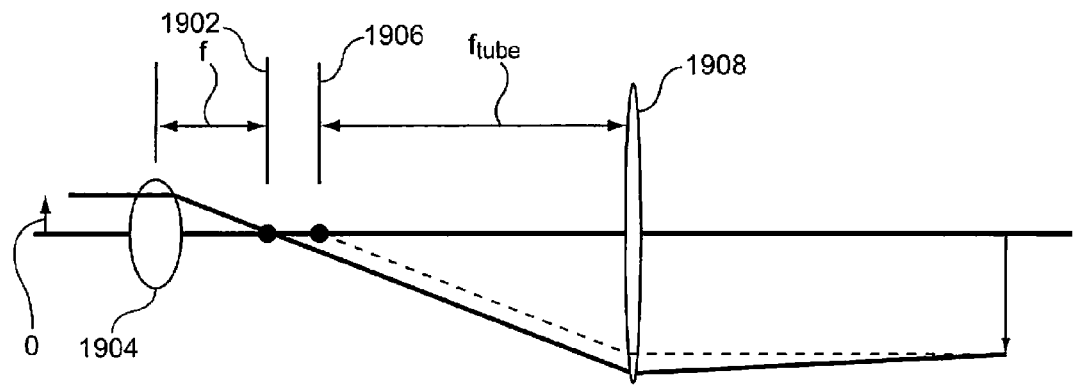
FIGS. 19B and 19C schematically illustrate an optical train that utilizes a parallel glass plate to maintain constant magnification within an optical system of the invention.
Figure 19C:
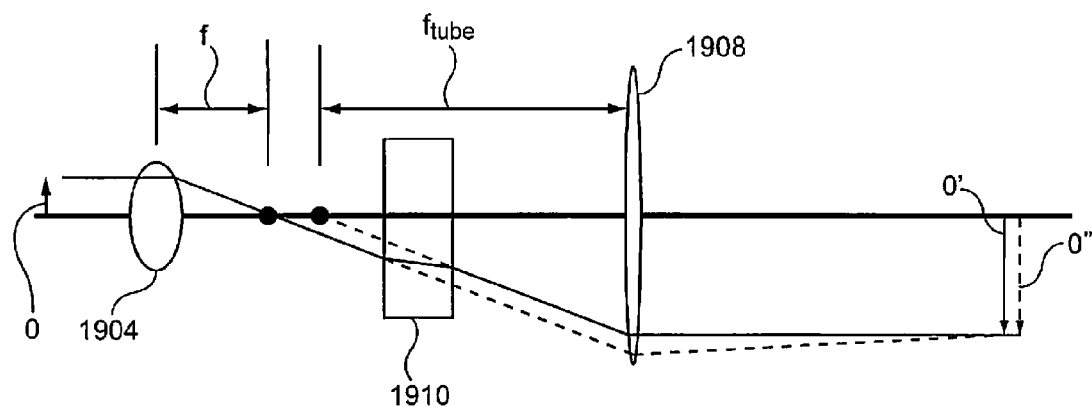

Aligning the system to meet the afocal condition can pose challenges, e.g., due to alignment errors in other portions of the optical system, or because the objective of the system is not designed for reversed usage (e.g., there is no back focal plane due to aberration). FIG. 19B illustrates the situation where the separation between the objective and tube lens does not exactly meet the afocal condition. The image height on the image plane is shown by the dashed arrow and the magnification is not equal to the focal length ratio of the tube lens and the objective, as illustrated in FIG. 19C. Object o is imaged onto o". However, when parallel glass plate 1910 is inserted between the objective and the tube lens and the glass plate's thickness is equal to that which exactly makes the chief ray of object o look like it is emanating from the front focal plane of the tube lens, then, after the tube lens, the chief ray of object o will be parallel to the optical axis and hits the image plane at o'. As a result, the magnification will be equal to the focal length ratio of the tube lens and the objective, independent of the substrate thickness. Thus, the glass plate can be positioned in such a way for the system to meet the afocal condition.

Figure 19D:
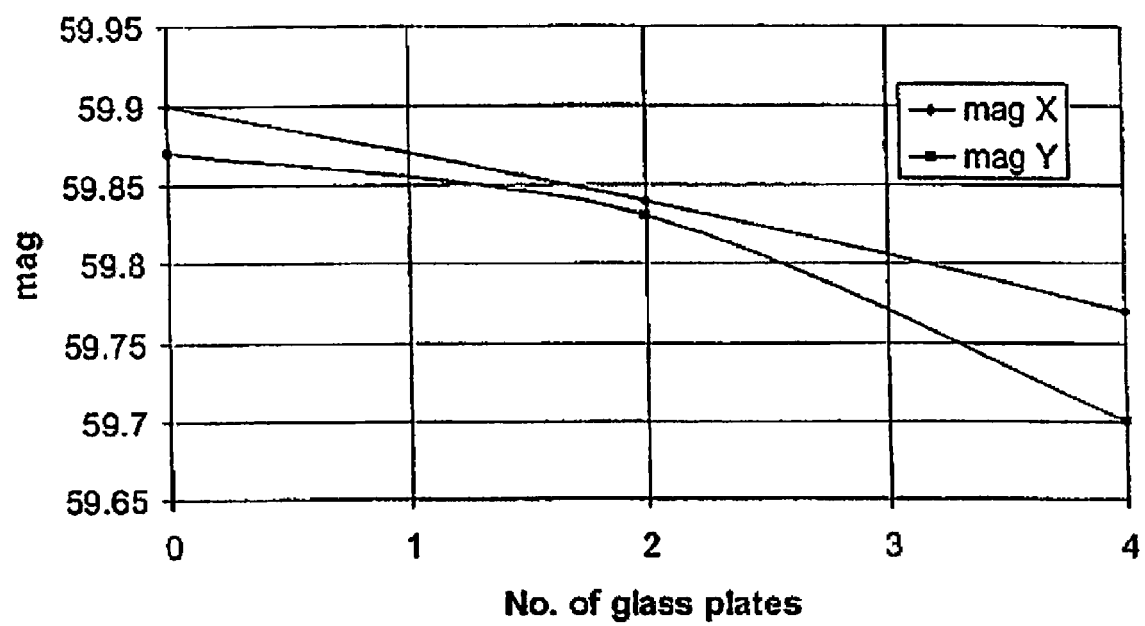
FIG. 19D shows the resulting magnification as a function of number of inserted glass plates within an optical system of the invention.

The parallel glass plate can also be employed to alter the system magnification by a desired amount. One of the functions of the parallel glass plate is to shift the chief ray height on the tube lens. By inserting a glass plate of appropriate thickness, one can obtain magnifications other than the focal length ratio of the tube lens and the objective by deviation from the afocal condition. Since the objective-tube lens system is designed and used for wide-band wavelength, the inserted parallel glass plate are preferably a low dispersion material. FIG. 19D shows the resulting magnification (as a function of number of inserted glass plates) in the x and y directions, respectively, achieved using approximately 1.5 mm thick glass plates.

Also provided by the present invention are substrate analysis systems that include alignment modules capable of automatically aligning the optical axis of a microscope objective with an optical path of optical energy passing through the objective. For substrate analysis systems designed for targeted illumination of (and collection of optical signals from) highly multiplexed reaction regions on a substrate, alignment of the objective optical axis is important, because it is the optical axis of the objective that serves as the fundamental reference for aligning both the collection path and illumination path; and misalignment of the optical axis of the objective can lead to asymmetric performance across the field of view, potentially degrading illumination performance.

When a collimated coherent beam, such as that from a laser, hits an axially symmetric optical surface, a portion of the incident light is reflected back to the incident media. The vertex of the surface and the center of the surface curvature forms the optical axis of that optical surface. When the incident beam precisely coincides with the optical axis of the optical surface (e.g., the optical surface of an objective), the reflected wavefront will be axially symmetric about the incident beam. The alignment module of the present invention utilizes this principle to align the objective optical axis, e.g., detect and correct decentering and tilt. Both in-line alignment, where the alignment is performed while the objective is in place, and off-line alignment, where the objective is not present during a portion of the alignment procedure.

The reflected wavefront can be, e.g., spherical, aspherical or planar depending upon the optical surface shape. If the optical system has many surfaces, there will be reflected wavefronts from each surface. These wavefronts interfere and form fringes. When observed on a plane perpendicular to the incident beam, the fringes are circular and symmetric to the incident beam center only when the incident beam coincides with the optical axis of the optical system. If there is either decentering, or tilt, or both, between the incident beam and the optical system, the fringes lose their axial symmetry. Since multiple beam interferences are employed, the fringe shapes are sensitive to decentering and tilts.

Figure 20:
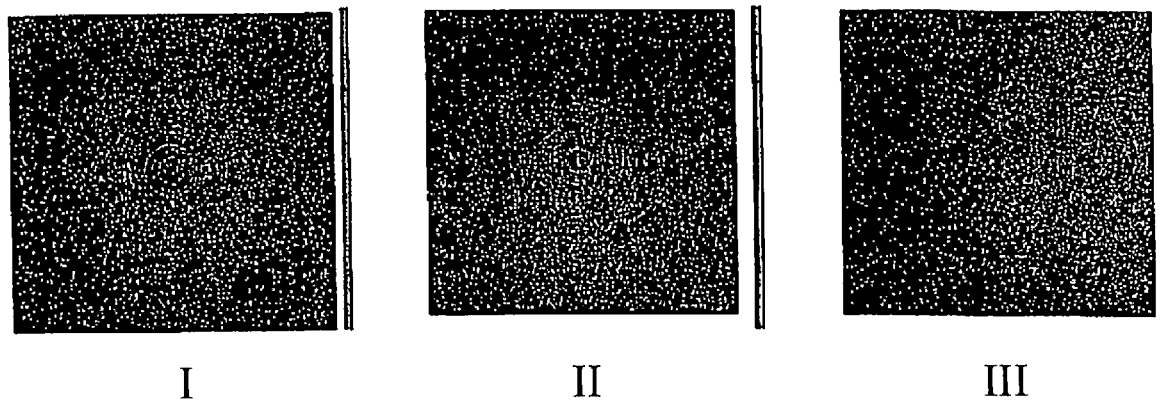
FIG. 20 shows simulated fringes formed by back reflected wavefronts from an objective during an in-line alignment procedure.

FIG. 20 shows simulated fringes, detected by an interference detector, formed by back reflected wavefronts from an objective during an in-line alignment procedure. Panel I shows the wavefront pattern when the objective optical axis is aligned. In this condition, the fringes are axially symmetric about the center. The wavefront patterns in Panels II and III indicate pure decentering (0.1 mm) and pure tilt (0.1 degree), respectively.

Figure 21A:
FIGS. 21A-C schematically illustrate an off-line alignment procedure for aligning an objective optical axis with an optical path passing through the objective.
Figure 21B:
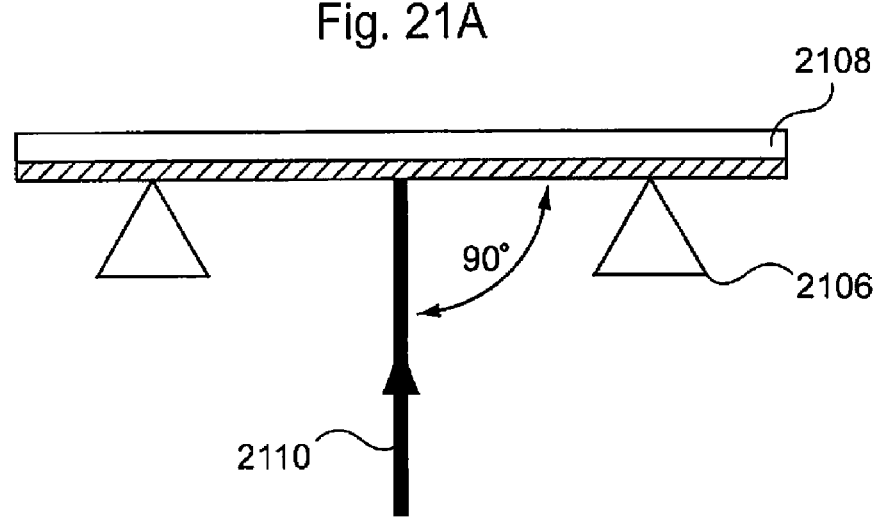
Figure 21C:
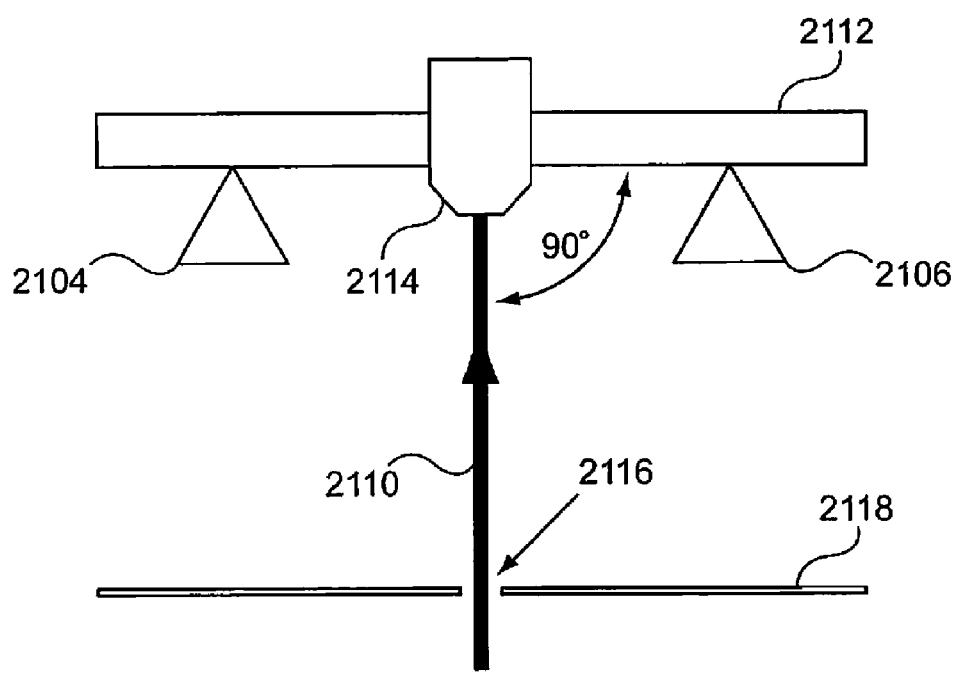

The present invention also provides an off-line alignment procedure, based upon the principle that when the optical axis of an objective is aligned perpendicular to a reference plane which is attached to the mounting of the objective, then as long as the laser beam is aligned to be perpendicular to that reference plane, the laser beam will be parallel to the objective optical axis. An example off-line alignment procedure in accordance with the present invention is illustrated in FIGS. 21A-C. As shown in FIG. 21A, the first step is to establish reference plane 2102 using two or more points on the objective mount, e.g., points 2104 and 2106. Next, as shown in FIG. 21B, flat mirror 2108 is placed on two or more points 2104 and 2106. A source of optical energy provides optical energy, e.g., laser beam 2110, which is aligned to be perpendicular to the mirror. FIG. 21C illustrates the final step, where the flat mirror is replaced by objective mount 2112 with associated objective 2114. As effected by the alignment module, objective 2114 is tilted and laser beam 2110 is translated laterally until fringes (obtained using the same method as described for in-line alignment above) are axially symmetric about hole 2116 on screen 2118.

For automated alignment, the fringes on the screen can be imaged onto an appropriate optical detector, e.g., a CCD or CMOS camera. The center hole is considered as the center of the fringes, and the fringe image can be divided into four quarters. The total energy in each quarter can be assigned a value. When the total energy values for each quarter are equivalent, alignment has been achieved.

Additional autofocus and/or alignment modules for determining the optimal focus and correction collar settings of an imaging system are provided by the present invention. In high N.A. fluorescence confocal microscopy systems, such as those that can be used for, e.g., single molecule fluorescence detection from an array of reaction regions, finding the focus and tuning the correction collar of an objective lens can be one of the most challenging aspects of overall system alignment. Modest amounts of out-of-focus error or correction collar setting error can degrade optical signal collection efficiency or throughput, encircled energy (power from a point source within a certain area on the detector), image position accuracy (reaction region image position on the detector), and the like. The present invention provides a numerical approach to determine the optimal focus and correction collar settings, providing a quick and quantitative measure of the image quality of an optical system, and can be used as a live feedback during the alignment process. In addition to performing focus and correction collar alignment, the autofocus and/or alignment modules described herein are also useful for providing a general measure of image quality in the optical system.

Figure 22A:
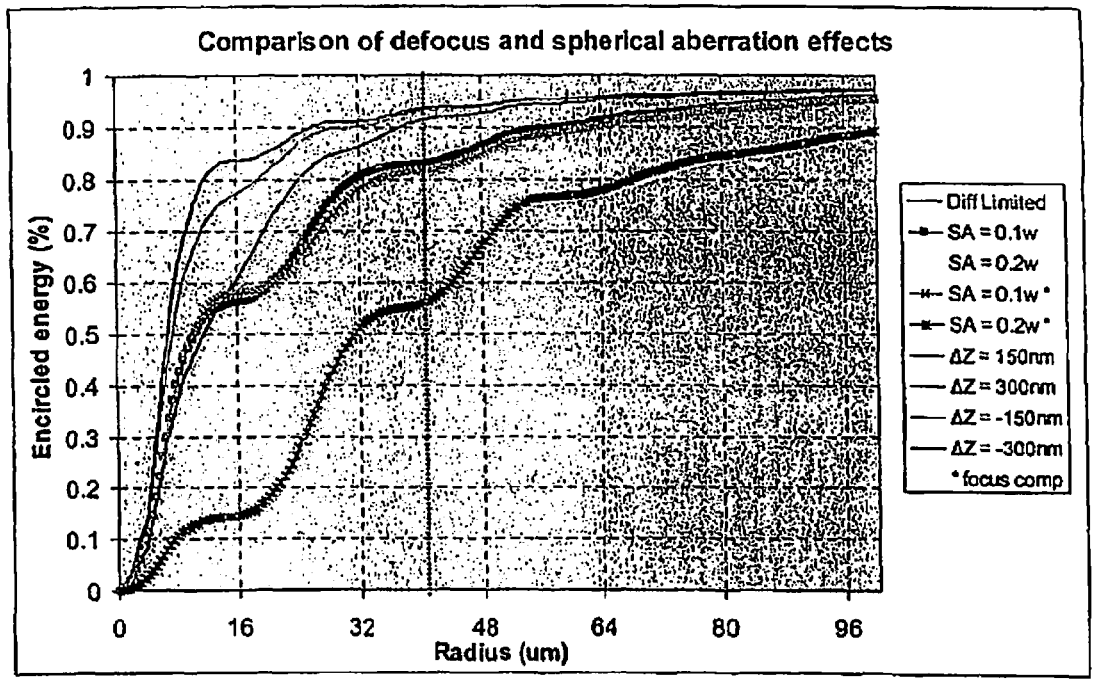
FIG. 22A shows encircled energy curves for various amounts of focusing error and correction collar setting error.

Z focus error and correction collar setting error are the two principal alignment errors in a high N.A. microscopy system. The impact of these two types of errors can be measured as the decrease in encircled energy, which is defined as the percentage of the total energy from a point source in the detector plane within a circle of certain radius. The encircled energy curves for various amounts of focusing error ($\Delta z$) and correction collar setting error, e.g., spherical aberration (SA), have been simulated and are shown in FIG. 22A. From these curves, one can infer the throughput decreases for the image from a reaction region, e.g., a zero-mode waveguide (ZMW). Assuming a circle with radius of 24 μm (approx. 3×3 EMCCD pixel box) is used to capture the fluorescence signal from a ZMW, the maximum achievable encircled energy within this circle is 89% (Diff Limited curve in FIG. 22A). A defocus error of 150 nm or 300 nm reduces the encircled energy down to 87% or 80%, respectively. A spherical aberration of 0.1 or 0.2 wave reduces the encircled energy down to 66% or 28%, even with focus compensation. The drop of encircled energy would result in a loss of throughput of the fluorescence signal as well as increased crosstalk (e.g., fluorescent signals from one ZMW landing on the detection region of another ZMW). Thus, optical system alignment can be improved by reducing these two errors.

A numerical method, which measures the average change in intensity between pairs of pixels, can be used by an autofocus and/or alignment module of the invention to find the best focus as well as the optimum correction collar setting. The function (fscore) that has been implemented is given by:

$$fscore(IM, n, m) = \sqrt{\sum_i \sum_j [(I_{i,j} - I_{i+n,j+m})^2 + (I_{i,j} - I_{i-n,j-m})^2]}$$

Equation 4

Power values other than 2, e.g., 4, 6, 8, etc., can also be used by the autofocus and/or alignment modules of the invention.

IM is the matrix containing the pixel intensity of an image; $I_{i,j}$ is the intensity of a pixel at location (i,j) within the image; i and j are the location index of the image pixels; n and m are the location offset of the second pixel. Location i and j range over all pixels within the image, where the pair of pixels are both within the index boundary.

Figure 22B:
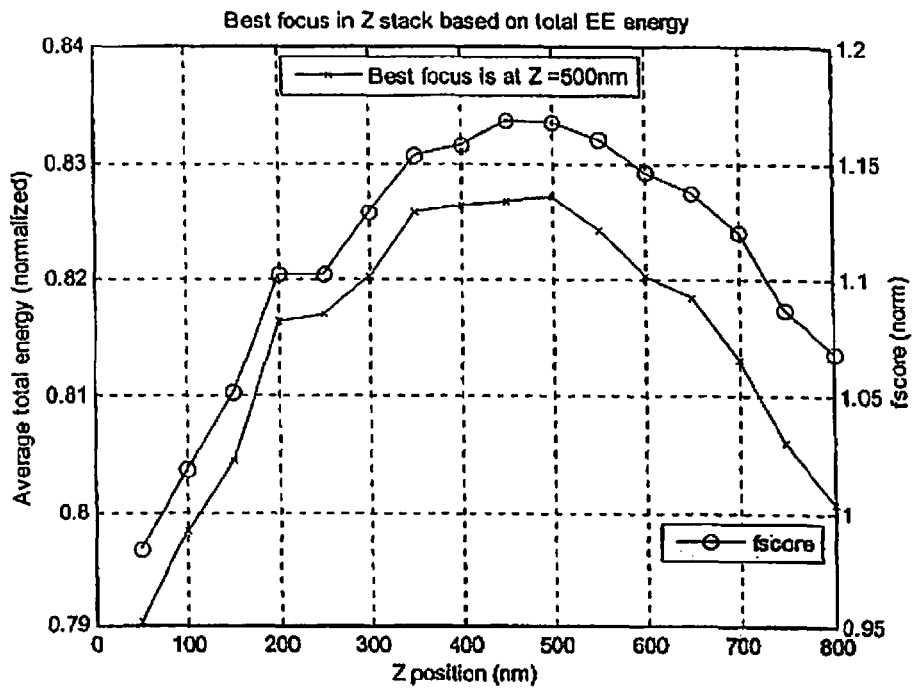
FIG. 22B shows f-score values and field-averaged encircled energies for images acquired at different Z positions of a substrate.

FIG. 22B shows fscore values and field-averaged (all reaction regions, e.g., ZMWs, in an image) encircled energies for various images acquired at different z positions, where the correction collar setting is kept constant. The offset of n and m, optical system-specific parameters which depend on resolution of the optics and detector pixel size, can be fine-tuned through calibration, e.g., n=1, m=1. Once the offset values are optimized, the fscore values of ZMW images acquired in a through focus scan peak at the same Z location, where the maximum field-averaged encircled energy (within a 24 μm circle) is found.

Figure 22C:
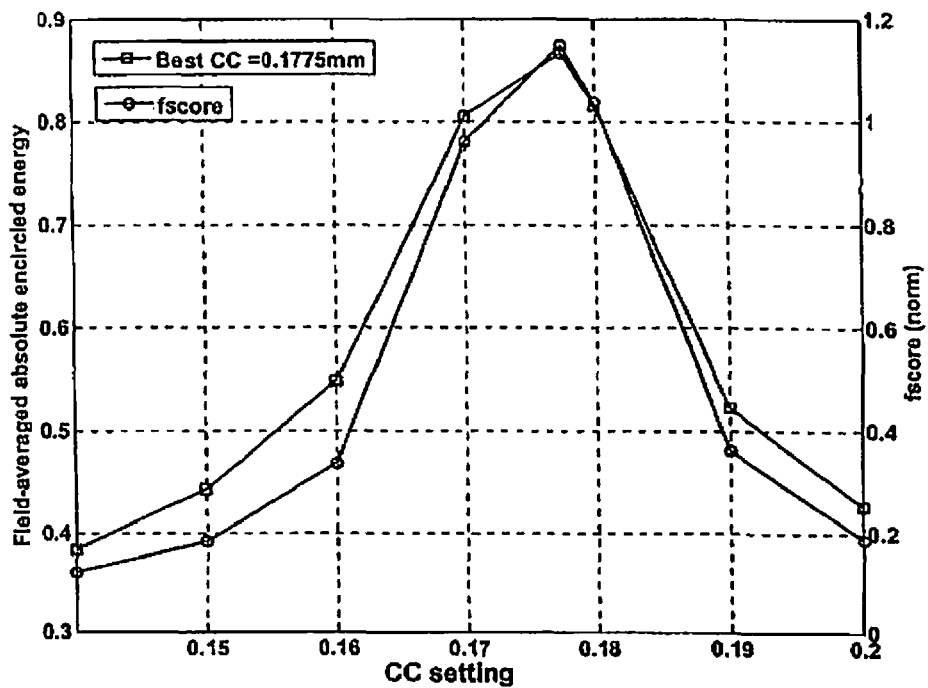
FIG. 22C shows f-score values and field-averaged absolute encircled energies for images acquired at different correction collar settings.

Using the same parameters, the fscore values and field-averaged encircled energies also peak at the same correction collar setting for various correction collar settings, at which the Z focus is optimized by the autofocus and/or alignment modules of the invention to find the highest encircled energy. FIG. 22C shows fscore values and field-averaged absolute encircled energy for various images acquired at different correction collar settings. The Z focus is optimized at each correction collar setting to obtain the highest encircled energy. These results indicate that autofocus and/or alignment modules that implement the fscore method can be used to find the best focus in Z, as well as the optimum correction collar setting, to minimize aberrations in the optical system.

Figure 22D:
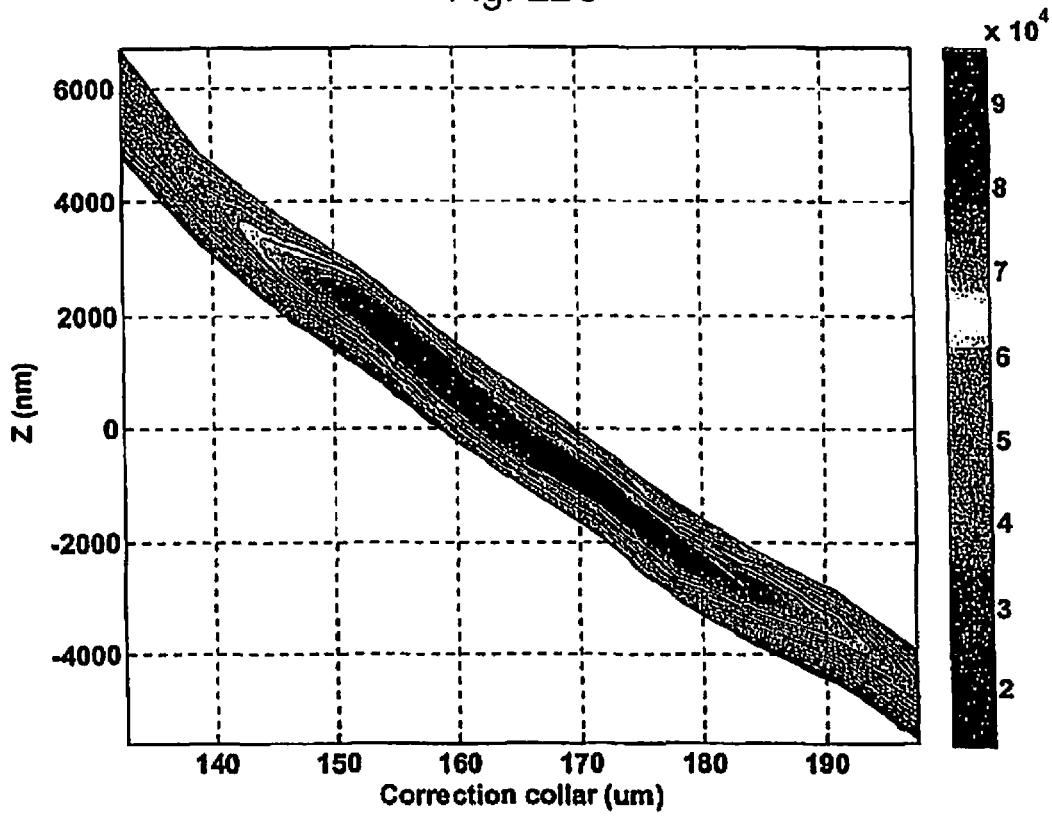
FIG. 22D shows a two dimensional f-score contour map for various Z positions of a substrate and correction collar settings.

To ensure the fscore can be used to determine the best focus in Z and optimum correction collar setting, the fscore values of images from an array of reaction regions, e.g., ZMWs, are captured. FIG. 22D shows a two dimensional fscore contour map for various Z positions and correction collar settings. As shown, the two dimensional fscore map has a single global maximum, with no local maximums. Therefore, a two dimensional search in the Z and correction collar space can be performed by the autofocus and/or alignment modules of the invention to determine the optimal image quality.

Substrate analysis systems optionally include an optical train that implements an autofluorescence mask positioned between the substrate and one or more optical detectors, which autofluorescence mask is configured to reject out-of-focus optical energy and prevents the out-of-focus optical energy from being detected by the one or more optical detectors. While such autofluorescence masks are useful for enhancing the detection of optical signals emanating from reaction regions of the substrate, the presence of the mask, in certain optical train configurations, can make it difficult to perform a number of functions to be carried out prior to analysis of the substrate. For example, locating, focusing, leveling, and adjusting the rotation of the substrate can be challenging when an autofluorescence mask is positioned within the optical train. The present invention provides optical system components in which the above functions (e.g., focusing, leveling, and the like) can be performed with an autofluorescence mask positioned within the optical system. Optical components that enable this functionality include new autofluorescence mask designs, optical detector layouts and alignment features on the substrate.

In one embodiment, an outer (non-analytic) portion of the substrate remains unblocked by the autofluorescence mask (e.g., a mask comprising chrome) and within the field-of-view of one or more optical detectors of the system. This configuration does not result in increased autofluorescence in the optical system because signals emanating from reaction regions of the substrate are not detected in this image region. Features, e.g., fiducial marks, on the substrate are arranged on all 4 sides of each pane. The features are located at precise positions relative to arrayed analytic reaction regions (e.g., analysis ZMWs) of the substrate, such that the fiducial marks facilitate alignment of the optical system to the reaction regions of the substrate while the mask is in place. When such features are similar to the reaction regions themselves, the features can be designed to reflect illumination light with maximal brightness, e.g., the features can be non-analytic ZMWs with maximum diameter.

Figure 23:
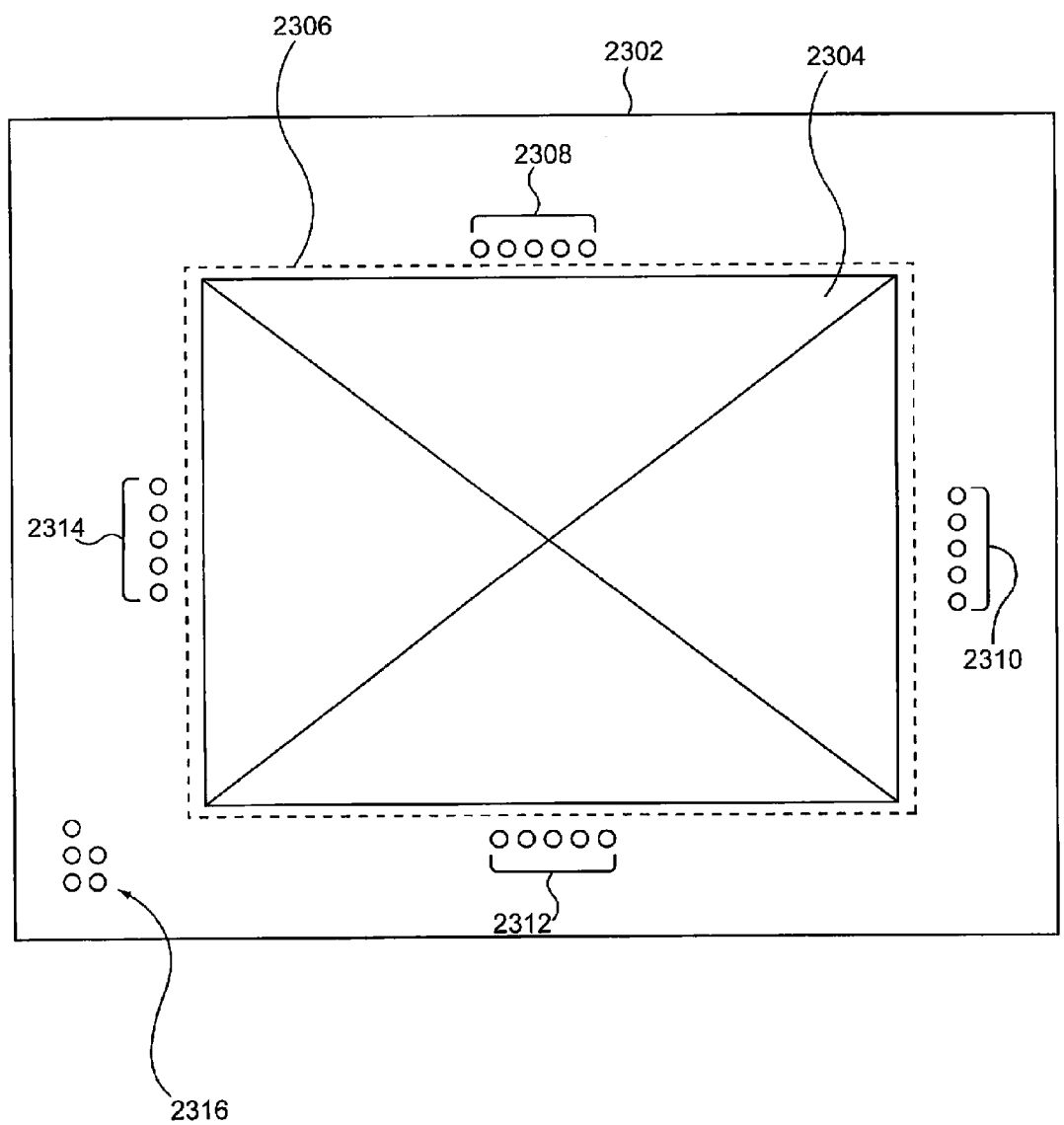
FIG. 23 is a schematic illustration of an image captured by one or more optical detectors of an optical system of the invention, which optical system utilizes an autofluorescence mask design and substrate fiducials to permit alignment of the system while the autofluorescence mask is operably positioned within the optical system.

An image captured by one or more optical detectors of an example system in accordance with the present invention is schematically illustrated in FIG. 23. Outer edge 2302 of the region surrounding autofluorescence mask 2304 (positioned between the substrate and the one or more optical detectors) delineates the field of view of the one or more optical detectors in the system. Beyond outermost mask boundary 2306 are one or more fiducials, e.g., non-analytic ZMW clusters 2308-2314, etched into each of the four panes of the non-analytic region of the substrate. Optionally, two dimensional bar code 2316 comprising, e.g., ZMWs or other optically detectable features, are disposed upon the substrate to facilitate identification of the substrate.

In this example, the four alignment fiducials are unique and recognizable via visual inspection by the operator of the system. In one embodiment, the fiducials are located by the system's image processing software when the fiducials appear within the open rim of the field of view. Once one or more of the fiducials is in view, a pane can be quickly aligned and the optional bar code identification will be visible. Moreover, the substrate can be focused by drawing ROIs that cover the four fiducial regions and monitoring the fscore. Leveling and rotating the chip is also facilitated by detecting and comparing optical energy reflected from the four fiducial regions.

In a related embodiment, optically detectable features, e.g., fiducials, are present on both the substrate and the autofluorescence mask, and the relative positions and orientation of the detectable features on the substrate and mask indicate alignment (or misalignment) of the substrate and the mask. An alignment module is provided that aligns the substrate and mask by comparing the relative position and/or orientation of images derived from the optically detectable features of the substrate and mask, which images are captured by the one or more optical detectors. Detection of the features is facilitated by transilluminated optical energy, where a source of transmission illumination optical energy (a "transilluminator") is positioned on a side of the substrate opposite the mask and one or more optical detectors. To prevent photodamage to reagents in reaction regions of the substrate, a transilluminator mask (TI mask) can be positioned between the transilluminator and the substrate, such that the mask prevents transillumination optical energy from illuminating analytic reaction regions of the substrate, while permitting the transillumination optical energy to illuminate the detectable features of the substrate and autofluorescence mask.

Figure 24:
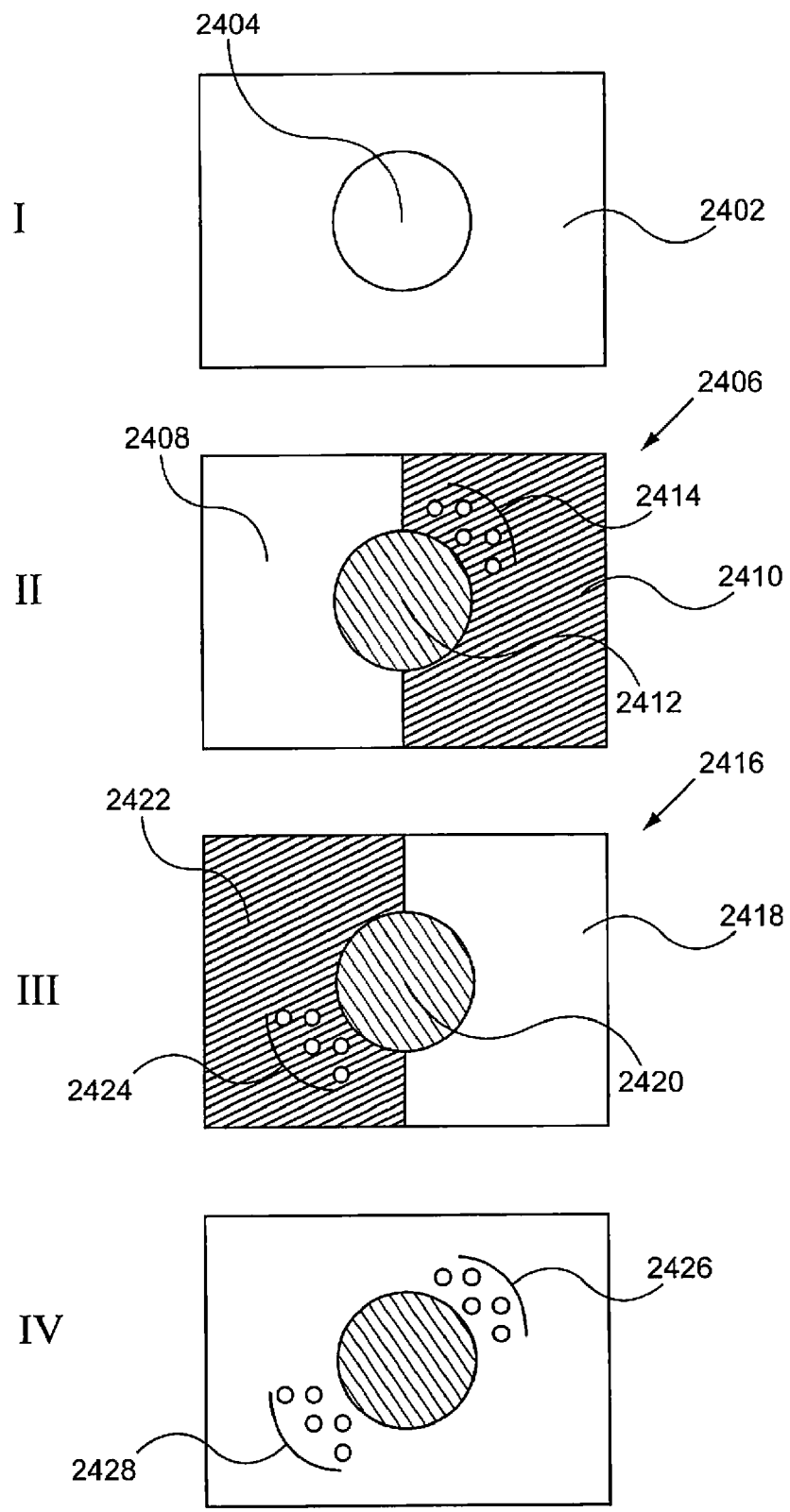
FIG. 24 provides schematic illustrations of transillumination masks, substrate designs and autofluorescence mask designs for aligning a substrate with an autofluorescence mask in accordance with the present invention.

FIG. 24 schematically illustrates example TI masks, substrates, autofluorescence masks, and the resulting images captured by one or more optical detectors of the systems of the invention. Panel I shows an example TI mask that includes transparent portion 2402 surrounding opaque portion 2404, where the shape and size of opaque portion 2404 corresponds to a region of the substrate where analytic reaction regions are provided. An example substrate design is shown in Panel II. As shown, substrate 2406 includes transparent portion 2408, opaque portion 2410 and a portion wherein analytic reaction regions are disposed upon or within the substrate, e.g., ZMW region 2412. Opaque portion 2410 includes optically detectable features, e.g., substrate fiducials 2414, which are transmissive to the transillumination optical energy. The transparent and opaque portions of the substrate can be provided in a number of ways. For example, the substrate can be made with an opaque layer (e.g., a metal layer, e.g., an aluminum layer) disposed over the entire surface area of the substrate, and the transparent layer is then provided by removing (e.g., etching) the opaque layer from the substrate where it is desirable for the substrate to be transparent, e.g., portions of the substrate other than ZMW region 2412 and opaque portion 2410. The fiducials in the opaque portion of the substrate can be any features that are optically detectable using the transilluminators and optical detectors of the invention. By way of example, the fiducials can be non-analytic ZMWs or other optically detectable features etched or otherwise disposed through an opaque layer of the substrate.

An example autofluorescence mask design is shown in Panel III. As shown, autofluorescence mask 2416 includes transparent portion 2418 to permit detection of substrate fiducials 2414 by one or more optical detectors in the system. Portion 2420 of the mask substantially corresponds to ZMW region 2412 of the substrate and permits optical signals emanating from reaction regions of the substrate to be detected by one or more optical detectors of the system. Autofluorescence mask 2416 also includes portion 2422 that is opaque to the transillumination optical energy. Disposed through portion 2422 of the mask are optically detectable features, e.g., mask fiducials 2424, which are transmissive to the transillumination optical energy.

An example image captured by one or more optical detectors of a system employing the optical elements described in Panels I-III is schematically illustrated in Panel IV. As shown, optical energy patterns 2426 and 2428 are detected by the one or more optical detectors and correspond to substrate fiducials 2412 and mask fiducials 2428, respectively. The relative positions and orientation between optical energy patterns 2426 and 2428 are indicative of the alignment (or misalignment) of the substrate and mask, and are also useful for tracking drift within the optical system as data from reaction regions of the substrate is collected.

Figure 25A:
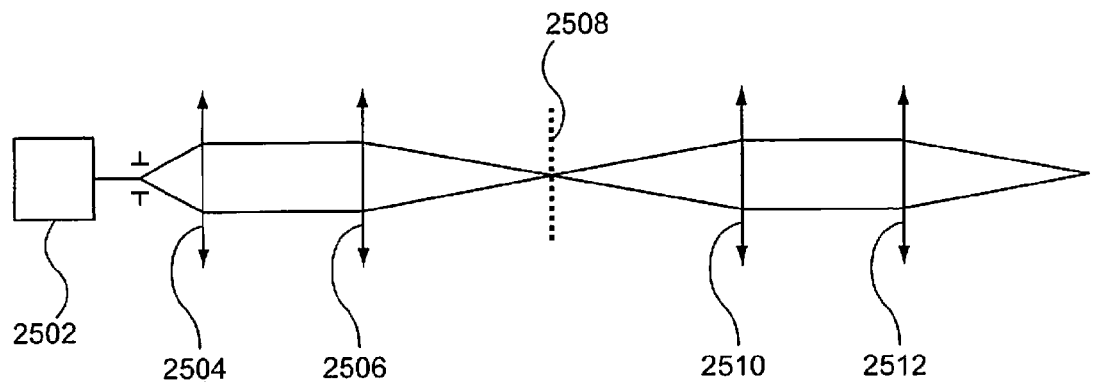
FIG. 25 schematically illustrates optical paths for imaging substrate and mask fiducials for aligning a substrate with an autofluorescence mask in accordance with the present invention.
Figure 25B:
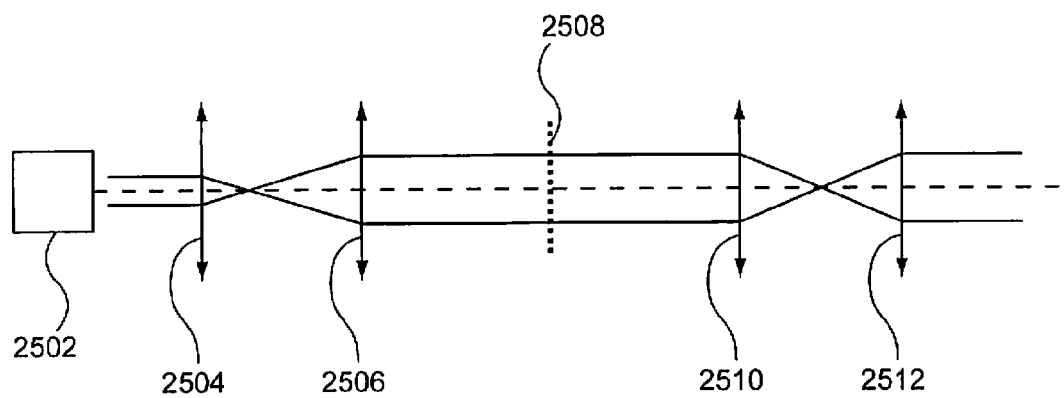

In a preferred aspect, the substrate fiducials and mask fiducials are imaged onto the one or more optical detectors through distinct optical paths, and the two images are combined for purposes of alignment and drift tracking. FIGS. 25A-B schematically illustrate example optical paths for imaging the substrate fiducials and mask fiducials, respectively. As shown, each path begins at source of transillumination optical energy, 2502. The transillumination optical energy (with a wave front that can be Gaussian or plane wave) passes through objective 2504, first tube lens 2506, mask 2508, second tube lens 2510, and image lens 2512 prior to being detected by one or more optical detectors.

The alignment systems of the invention are automatable and capable of carrying out an alignment procedure that can include registering the mask position relative to the one or more optical detector and aligning the substrate to the mask by aligning the images from the substrate fiducials and mask fiducials. For drift correction, the system can continuously or periodically monitor the relative position and orientations of the substrate and mask fiducials and employ an image based algorithm to correct any drift detected in the system. This alignment approach provides numerous advantages. For example, it permits simultaneous alignment of the substrate and optical detector to the mask. Imaging substrate and mask fiducials permits dynamic tracking and a short alignment times. Further, the transilluminator is stable, its intensity and illumination period are adjustable, and the system is not sensitive to laser drift.

The present invention provides optical train configurations for focusing and leveling a substrate with an autofluorescence mask positioned between the substrate and one or more optical detectors. In one embodiment, a module for determining positional information of the substrate about one or more axis is provided, the module including a dichroic filter placed in the collection path before the mask, where the dichroic is configured to direct light from the objective to an alignment camera or one or more position sensitive detectors (PSDs) placed at the mask plane. One or more autofocus lasers and a transmission illumination laser can be used to provide optical energy reflected from the substrate and/or transmitted through the substrate, which optical energy is ultimately directed by the dichroic in the collection path toward the alignment camera or one or more position sensitive detectors.

Figure 26:
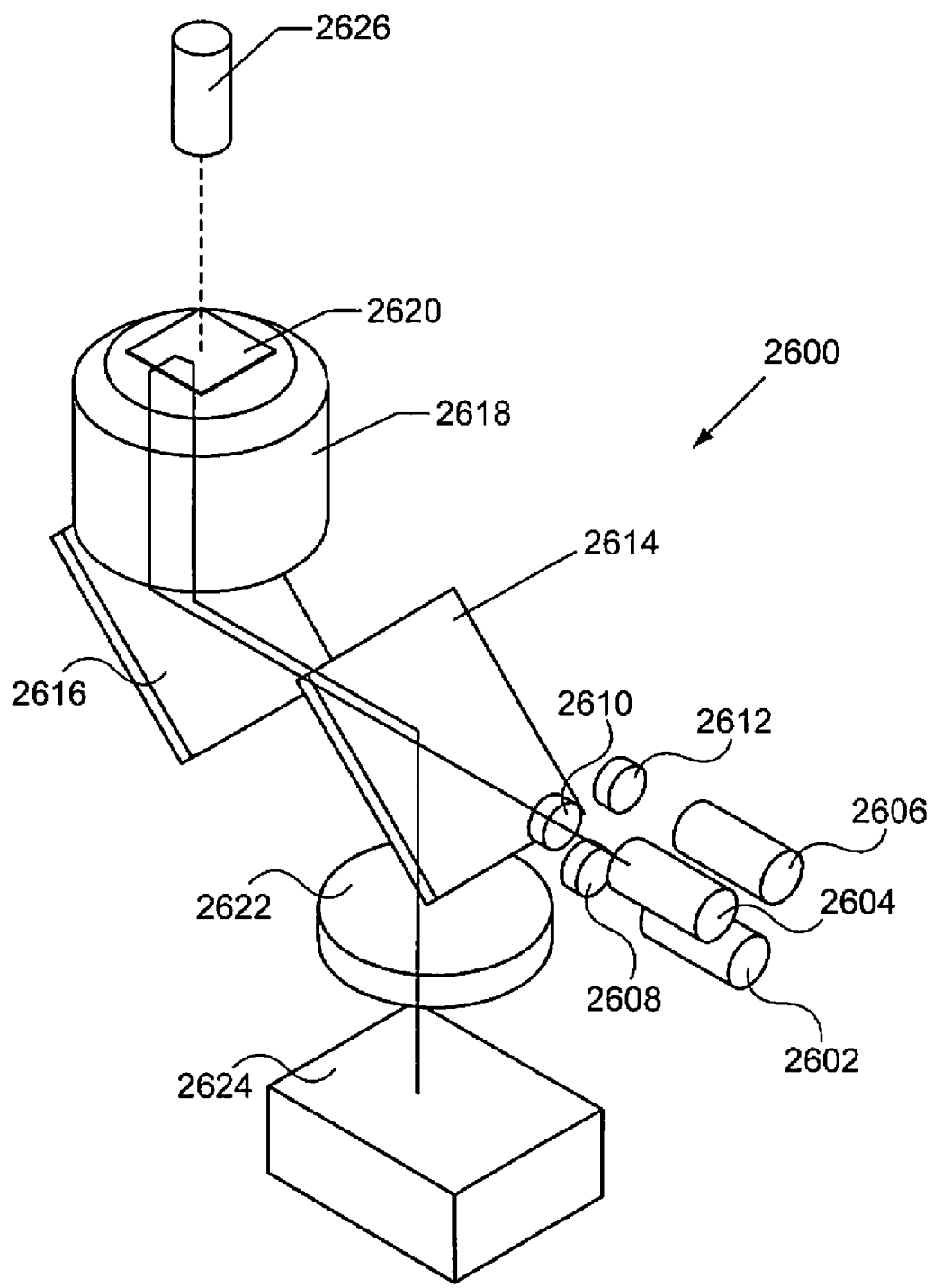
FIG. 26 is a schematic illustration of an optical train configuration of the present invention for focusing and leveling a substrate with an autofluorescence mask positioned between a substrate and one or more optical detectors.

An example module for determining positional information of the substrate about more than one axis in accordance with the present invention is shown in FIG. 26. As shown, module 2600 includes focus lasers 2602-2606 from which focus laser beams optionally pass through focal plane shifting lenses 2608-2612, then through 50% reflector 2614 and reflected from dichroic 2616 through objective 2618 before reaching substrate 2620. A single focus laser beam is shown for ease of illustration. The focus laser beams reflect back from substrate 2620 through objective 2618 to be reflected off dichroic 2016 and 50% reflector 2614, optionally passing through tuning lens 2622 before becoming incident upon camera or one or more PSDs 2624.

The position on the alignment camera or one or more PSDs of the reflected spots from the three autofocus lasers can be used to determine Z position, rotation about X and rotation about Y. The transmission illumination, e.g., emitted from transmitted light source 2626, is used to generate an image on the alignment camera which provides X,Y positional information and rotation about Z. The three autofocus lasers and the transmission illumination laser can be configured to provide optical energy in an alternating fashion to avoid interference between these two laser systems.

Also provided by the present invention are modules capable of independently tracking, with self-correction capability, Z-focus and substrate leveling. Leveling tracking and initialization is performed by tracking the image shift on the back focal plane of the objective. The back focal plane image is formed by back-illuminating a microlens/micromirror array on the substrate with a plane wave. For Z-focus tracking, two autofocus beams are employed, where a reciprocal beam compensates for any error exhibited by the counterpart beam.

The modules of the invention provides a number of benefits. The separation of leveling and Z-focus results in relatively simple algorithms and fast convergence. The modules are highly sensitive to errors in leveling, Z-focus, and substrate rotation, and accordingly are capable of correcting small errors in these parameters for optimal signal collection. Moreover, alignment of optical systems that employ the autofocus and leveling modules of the invention are not sensitive to substrate thickness, and back-illumination with infrared light does not damage photolabile reagents under conditions of long-term illumination.

Figure 27:
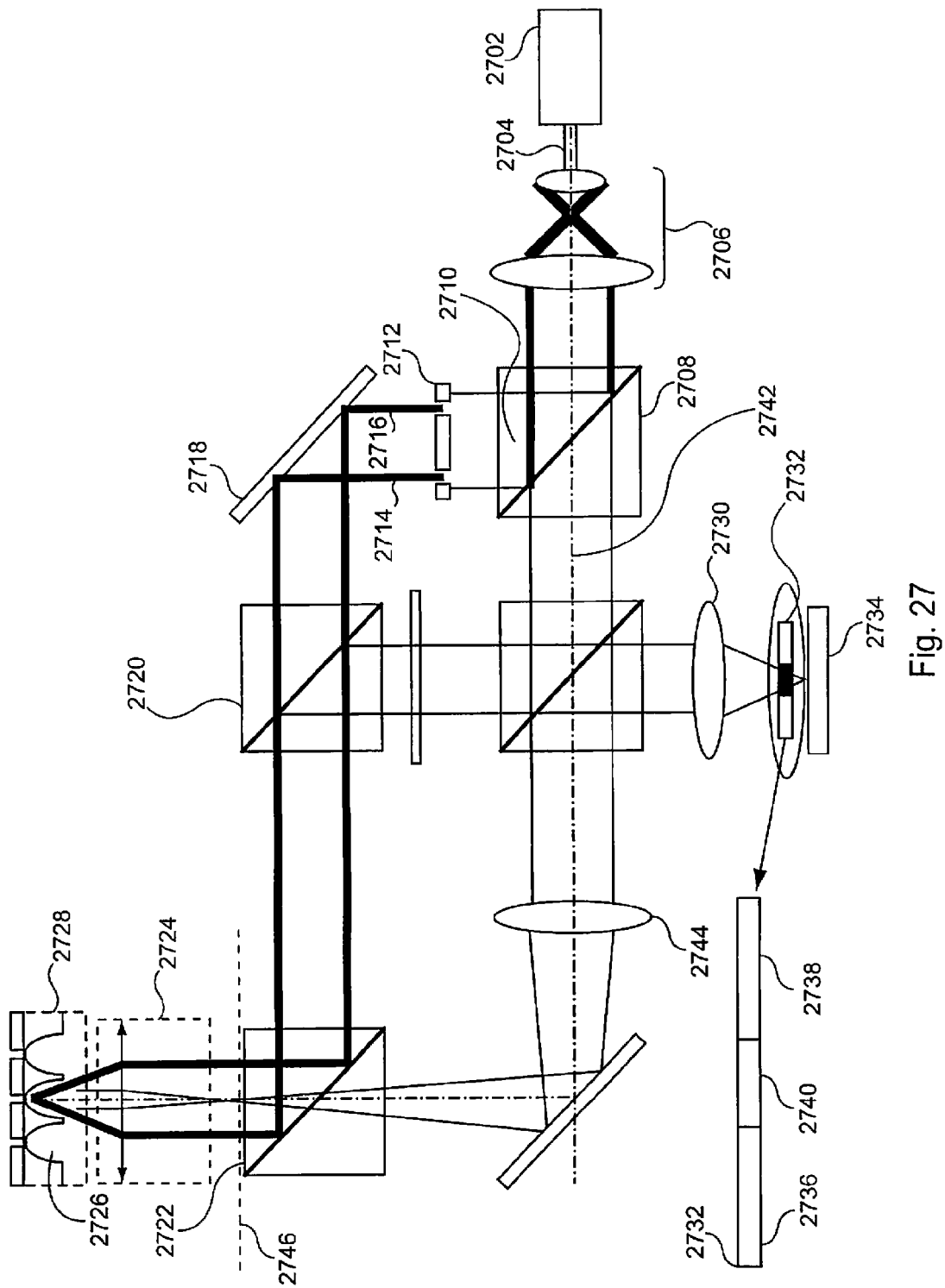
FIG. 27 provides a schematic illustration of an autofocus and leveling module of the invention.

An example autofocus and leveling module is schematically illustrated in FIG. 27. As shown, optical energy is provided to the module by an optical energy source, e.g., non-polarizing collimated diode laser 2702. Laser beam 2704 is expanded by beam expander 2706 and split into two beams by polarized beam splitter 2708. Beam 2710 passes through grating 2712 to generate two Z-focus beams 2714 and 2716, which are parallel to each other and equidistant to the center optical axis. Both Z-focus beams are reflected by mirror 2718, propagate through beam splitter 2720, are reflected by polarized beam splitter 2722 into objective 2724, and then reflect off of one or more features, e.g., microlens/micromirror 2726 disposed within substrate 2728. The reflected beams are reflected by beam splitter 2720 and focused by tube lens 2730 through polarizer 2732 onto an optical detector, e.g., CCD 2734. Polarizer 2732 consists of transparent lateral portions 2736 and 2738 and polarizing central portion 2740. Z-focus tracking is carried out by monitoring any shift in the image of the two Z-focus beams and providing instructions to the optical train using an image-based algorithm to compensate for the particular shift observed, e.g., moving the substrate axially until optimal focus is achieved, and the like.

Leveling beam 2742 is focused by conjugate lens 2744 onto back focal plane 2746 of objective 2724. Mirror 2748 is configured to reflect leveling beam 2742 passing through conjugate lens 2744 onto back focal plane 2746. Objective 2724 converts the focused beam to a plane wave, where the microlens array (a reflective grating) disposed upon the substrate generates diffraction orders under plane wave illumination. Each diffraction order forms a spot on the back focal plane of the objective. The back focal plane image, which conveys information relating to the leveling of the substrate, is magnified by conjugate lens 2744 and tube lens 2730 and captured by CCD 2734. Similar to Z-focus tacking above, image-based algorithms may be used to recalibrate the optical train in the event that leveling misalignment is detected.

Figure 28:
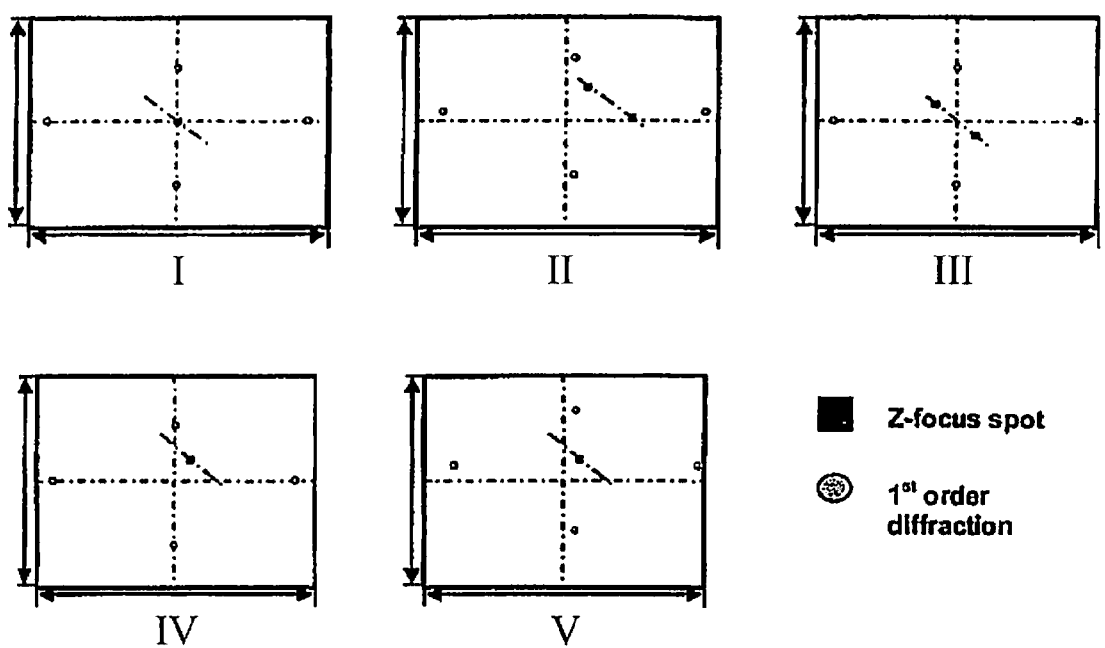
FIG. 28 shows the types of images that can be obtained via implementation of an autofocus and leveling module of the invention.

FIG. 28 shows the types of images that can be captured using the autofocus and leveling modules of the invention, depending on whether or not the substrate is tilted (e.g., not level), Z-focus error exists, and/or the two optical paths are misaligned. Z-focus spots are indicated by solid squares, while diffraction order spots indicative of leveling are indicated by circles. Panel I shows the condition where the optical train is aligned in each of the three respects (leveling, Z-focus, and optical paths). The image pattern of Panel II indicates that the substrate is tilted and Z is out of focus. In Panel III, leveling is aligned but Z is out of focus. Panel IV indicates that leveling is aligned and Z is in focus, but the two optical paths are misaligned. In Panel V, leveling is misaligned, Z is in focus, and the two optical paths are misaligned. Data from the images can be processed using image-based algorithms to effect a recalibration of the system such that all three parameters are optimized for monitoring signals, e.g., optical signals from fluorescently-labeled reagents, emanating from arrayed reaction regions across substantially the entire surface of the substrate.

The module enables day-to-day calibration of the optical train based on microlens images. If necessary, certain optical elements within the optical train can be moved relative to one another to align the two optical paths. Regarding tracking from substrate to substrate, leveling can be performed by bringing the mid-point of the 1st order pattern to the registered position by stage legs, and focus can be accomplished by moving all three legs together. Drift (referring to the optical system, which is properly aligned when substrate analysis commences, becoming misaligned due to, e.g., thermal expansion of components within the optical train due to heating caused by excitation radiation, computer components, and the like) can be monitored according to the alignment of the two optical paths, and when misalignment between the paths is detected, recalibration of the system can be accomplished by employing an image-based algorithm.

The present invention provides additional modules for monitoring and correcting for drift that can occur during operation of substrate analysis systems. In one embodiment, the substrate analysis systems comprise a drift tracking module that provides transilluminated optical energy, e.g., from a laser or LED light source positioned on a side of the substrate opposite the optical detector(s) of the system, intermittently through the substrate such that images of the transilluminated substrate can be periodically captured to determine the amount of drift, if any, that is occurring in the system. Because the transillumination occurs rarely (e.g., once every 100, or once every 1000 frames captured by the optical detector(s)), bleaching of photolabile reagents within reaction regions of the substrate is minimized. Pulses of transillumination can be synchronized with frames captured by the optical detectors of the system to minimize any corruption of frames intended to capture optical signals emanating from the reaction regions. Further, information regarding which frames were captured when a transillumination pulse occurred can be communicated to the data analysis modules of the system so that analysis of those frames can be adjusted accordingly. The drift tracking module can also be configured to synchronize transillumination pulses to the camera shutter to prevent potential corruption of frames.

Figure 29:
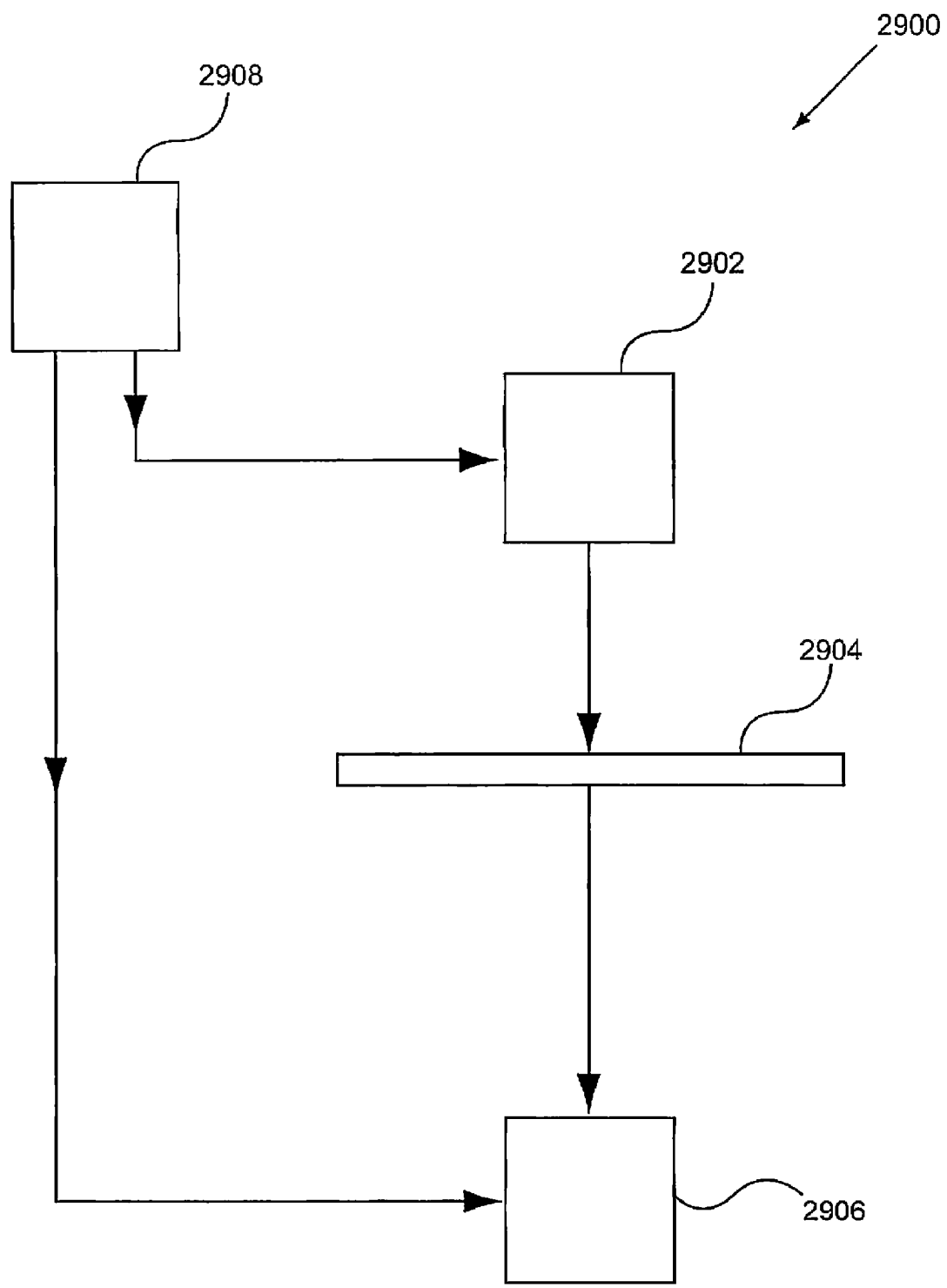
FIG. 29 schematically illustrates a drift tracking module of the invention.

An example drift tracking module is schematically illustrated in FIG. 29. As shown, module 2900 includes a transillumination optical energy source, e.g., LED light source 2902 which emits optical energy toward (and through transparent regions of) substrate 2904. The transillumination optical energy passing through the transparent regions (e.g., regions through which a reflective surface of the substrate has been etched away, e.g., zero-mode waveguides) is detected by an optical energy detector, e.g., camera 2906 disposed opposite LED light source 2902 relative to substrate 2904. Control electronics 2908 send enable signals to LED light source 2902 and external synchronization signals to camera 2906, such that pulses of transillumination optical energy can be synchronized with frames captured by camera 2906 and marked as a frame taken during a transillumination pulse. The marking of such frames is useful during processing of optical signal data (derived from optical signals emanating from reaction regions of the substrate) by a signal analysis module. For instance, it may be desirable to discard a frame captured concurrently with a pulse of transillumination optical energy. Module 2900 can employ an image-based algorithm that utilizes data from camera 2906 to determine whether the position of the substrate has drifted. The module can be configured to align the optical train and/or substrate when the module determines that the position of the substrate has drifted.

Figure 30A:
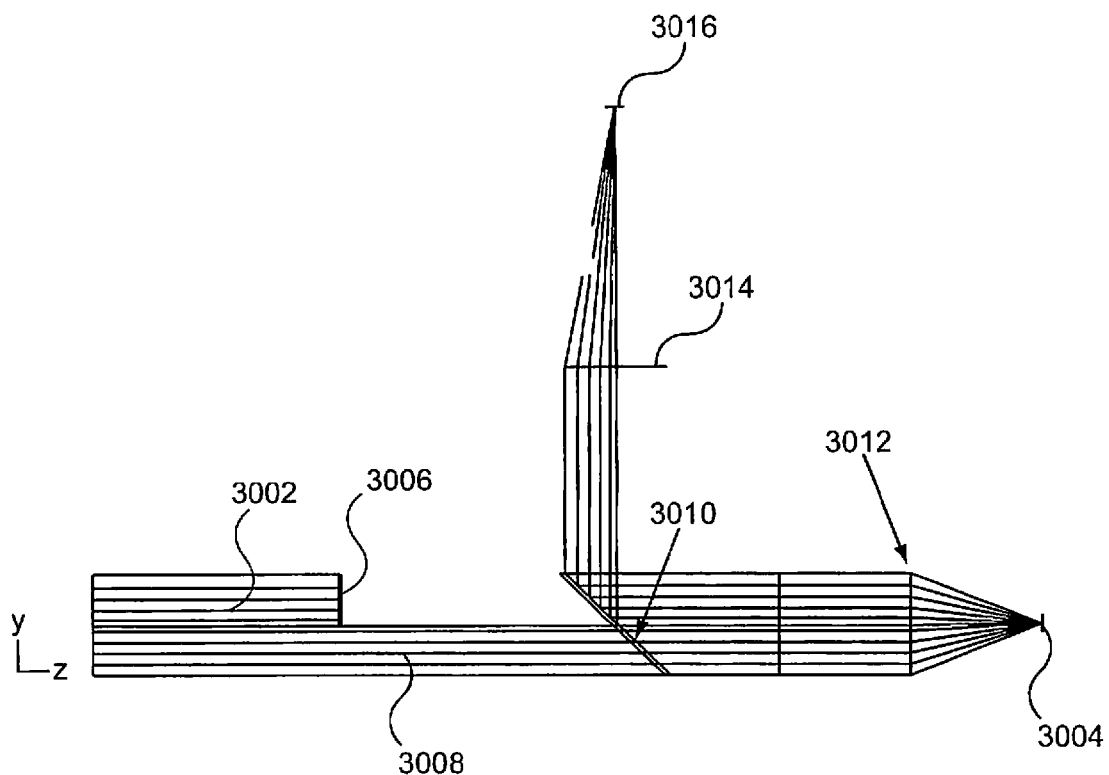
FIG. 30 is a schematic illustration of a half-beam illumination autofocus module of the invention.

The present invention provides additional improved autofocus modules that find use in substrate analysis systems. An example autofocus module is schematically illustrated in FIG. 30A. As shown, a full size beam of optical energy, e.g., laser beam 3002, directed toward substrate 3004 is blocked by half beam blocker 3006. The resulting half beam 3008 passes through dichroic 3010 and is focused by objective 3012 onto a surface (e.g., a metal surface) of substrate 3004. Half beam 3008 is reflected back from the surface of substrate 3004 and recollimated by the other half of the aperture of objective lens 3012. The recollimated beam is reflected by dichroic 3010 and imaged by tube lens 3014 onto an optical detector, e.g., CCD 3016.

Figure 30B:
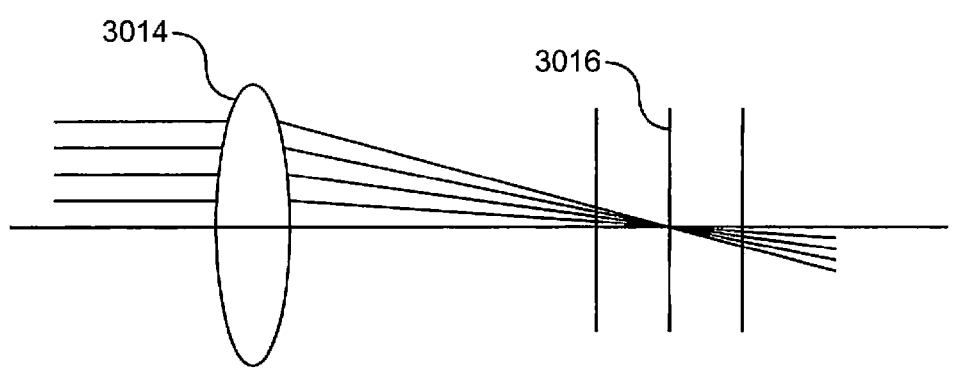
Figure 31:
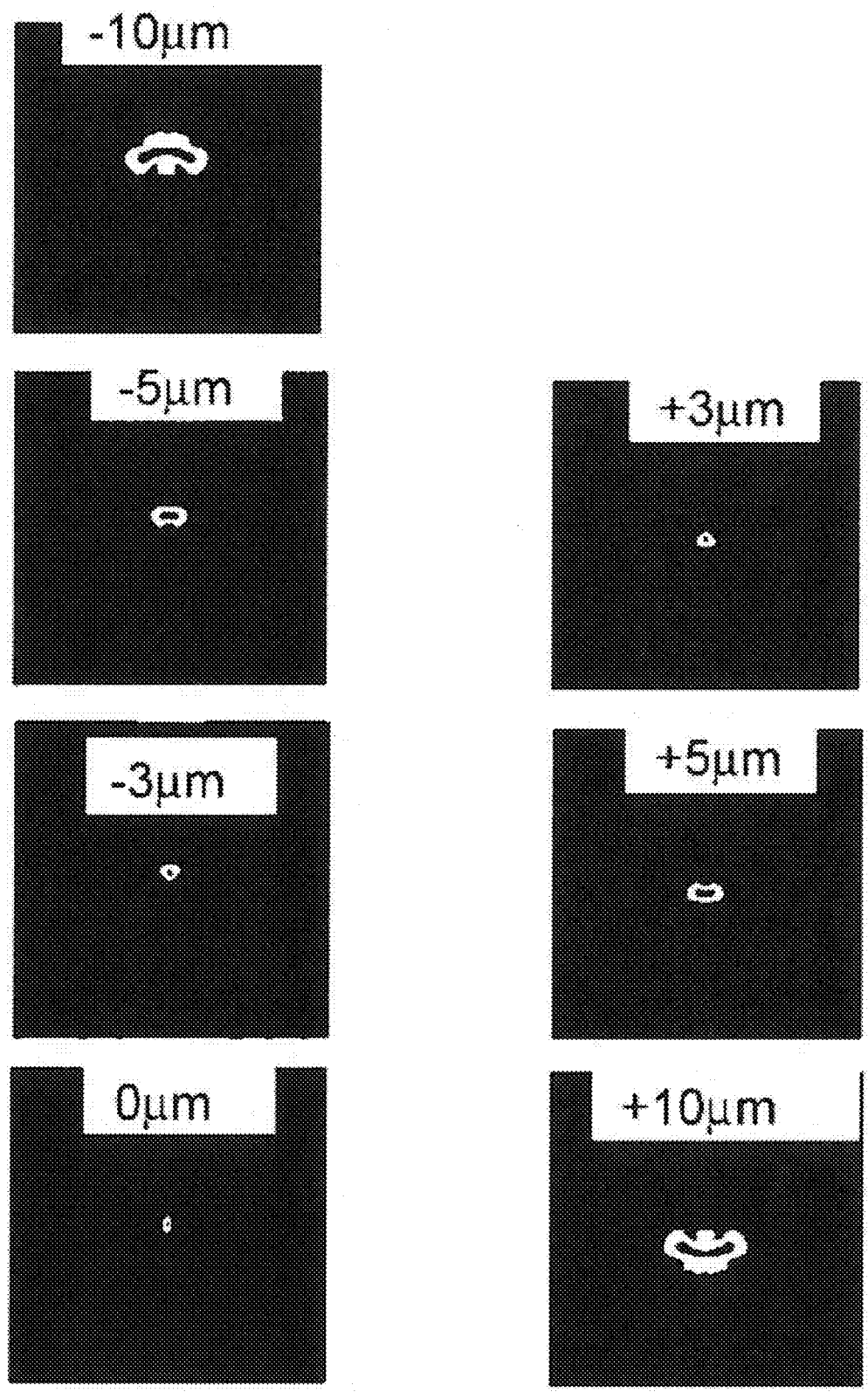
FIG. 31 shows simulated spot patterns obtained using a half-beam illumination autofocus module of the invention.

As schematically illustrated in FIG. 30B, the half beam size illumination will generate different pattern orientations on the optical detector, which pattern orientations contain information about whether the plane of the substrate is beneath, in front of, or in the focal plane 3016. FIG. 31 shows simulated spot patterns when the amount of de-focus is from −10 µm to +10 µm. An image-based algorithm can be implemented to correct any de-focus by adjusting the position of elements in the optimal system, depending on the spot pattern captured by the optical detector.

For many substrate analysis applications, e.g., high-throughput substrate analysis, it is desirable to minimize the time required to perform an initial alignment of the substrate with the focal plane of the optical detector. The present invention provides substrate leveling modules for rapid focal plane determination. The modules is based upon the principles that the substrate to be focused is approximately planar, the focal metric function follows an approximately Gaussian (or perhaps an Airy) shape, the peak of the focal metric function should appear quadratic, and the repetitious planar structure of the substrate should provide approximately identical behavior of the focal metric function as one moves along Z, regardless of which sufficiently large patch is analyzed in X and Y.

Based upon these principles, substrate leveling modules of the invention divide the substrate into a large number of vertical columns and actuate to a relatively low number of Z locations to infer the peak Z on a per-column basis. A planar fit to these per-column peaks yields the required information about the chip-to-focal plane relative orientation. An advantageous feature of the substrate leveling modules is that a passive alignment method is implemented, obviating the need for additional elements, e.g., position sensitive detectors or special cameras, in the optical system.

The following outlines the routine carried out by the leveling modules of the invention. First, the substrate is moved to several locations, e.g., between 3 and 7, with distinct Z locations, and acquire a small number of images, e.g., between 1 and 10, are acquired at each location, which might be averaged to reduce camera noise. For each image (or averaged image), a focal score for a number of different blocks within the image are calculated. The focal score describes the quality of focus of a given image captured by an optical detector, where a larger focal score indicates a higher quality of focus. A number of methods for assigning a focal score are possible, e.g., determining the square of the gradient of an image captured by the optical detector. For each block, a curve is fit to focal scores as a function of Z location. If the Z locations occur over a relatively large range, a Gaussian fit is applied. When the Z locations occur over a relatively small range, a quadratic fit is applied. The maximum value of the fitted curve reflects where the peak focal score sits in Z for a particular block. Each block resides at a distinct X-Y location, and this peak focal score is treated as the peak focal score along a line in Z through the center of the block.

The previous step provides a collection of X, Y, and Z values which reflect where the optimal focal scores reside. These points reside in a plane, so a plane is fitted to these points. The fitting procedure may employ a standard least-squares approach, or if outliers disrupt the fit, an iteratively reweighted least-squares approach may be implemented. The optimal focus plane is used to determine a stage translation and rotation that moves the substrate mount into a position for optimal focus. Once the mount is moved to this position, a second iteration of the alignment procedure is performed using a lesser number (e.g., a predetermined fraction, e.g., 50%) of Z locations. The alignment procedure is iteratively performed until convergence is achieved, or a fixed number of iterations can be performed. Alternatively, convergence can be achieved by determining the magnitude of the translation and/or rotation. By way of example, if there are four moves per iteration, with each move carried out in 500 ms, 20 µm alignment uncertainty, and 50% convergence achieved per iteration, eight moves would be required to converge within 100 nm. Accordingly, the module could perform the alignment procedure in approximately 16 seconds or less. The short duration of the alignment procedure meets the requirements of high-throughput substrate analysis applications.

Leveling modules of the invention can calculate focal scores based on the Tenengrad function, which produces smooth, Gaussian-like curves. The Tenengrad function also provides a defined peak value, is invariant under rotation, and is simple to use on variably-sized image regions. The Tenengrad function is as follows:

$$F_s = \sum_g \left( \begin{bmatrix} -1 & 0 & 1 \\ -2 & 0 & 2 \\ -1 & 0 & 1 \end{bmatrix} + Si, j \right)^2 + \sum_g \left( \begin{bmatrix} 1 & 2 & 1 \\ 0 & 0 & 0 \\ -1 & -2 & -1 \end{bmatrix} + Si, j \right)^2 \quad \text{Equation 5}$$

Figure 32A:
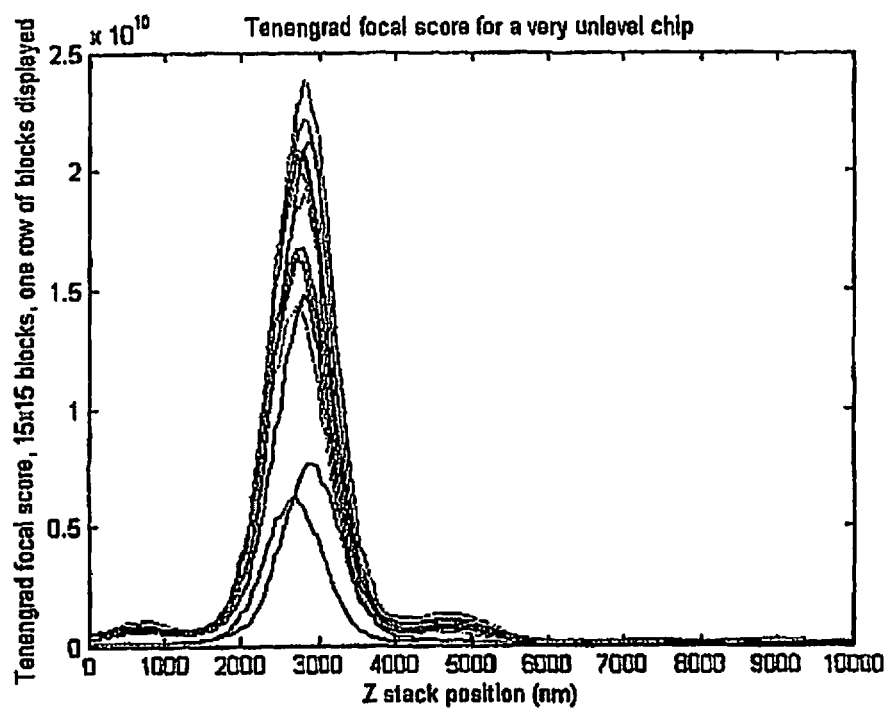
FIGS. 32A and 32B show unlevel substrate focal score plots obtained by an autofocus module of the invention.
Figure 32B:
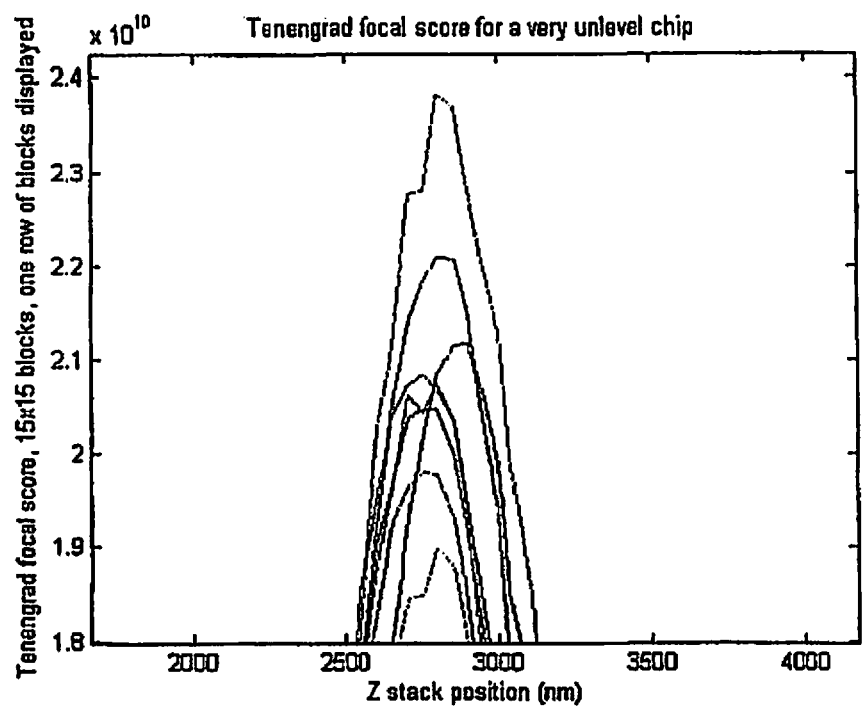
Figure 32C:
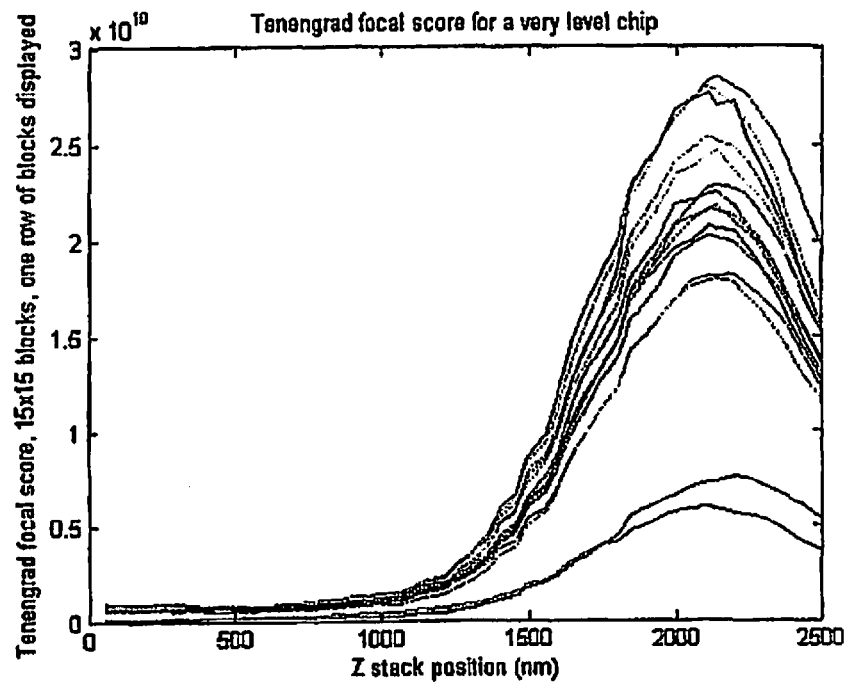
FIGS. 32C and 32D show level substrate focal score plots obtained by an autofocus module of the invention.
Figure 32D:
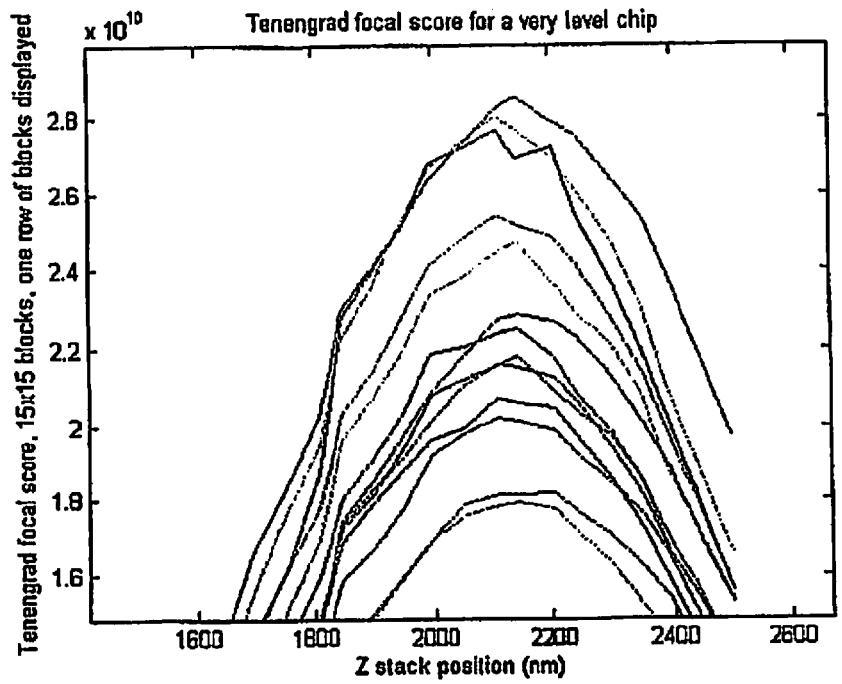

FIG. 32A shows the Tenengrad focal scores for an unlevel substrate. FIG. 32B shows the image near the peak of the curves from FIG. 32A, where each curve has a single, well-distinguished maximum value, and is mostly symmetric. FIG. 32C shows the Tenengrad focal scores for a substantially level substrate, where the peaks of the focal scores are tightly aligned. FIG. 32D shows the image near the peak of the curves from FIG. 32C, where the maximum values are relatively close to one another, indicating a substantially level substrate.

For curve fitting, the leveling modules of the invention fit the focal score as a function of Z location for each block in the image for which a focal score is assigned. The course alignment function to be fit (Gaussian) is as follows:

$$f(z) = C^* \text{Exp}(-(z-A)^2/2B^2) \quad \text{Equation 6}$$

The fine alignment to be fit is as follows:

$$F(z) = -C^*(z-A)^2 + B \quad \text{Equation 7}$$

Figure 33A:
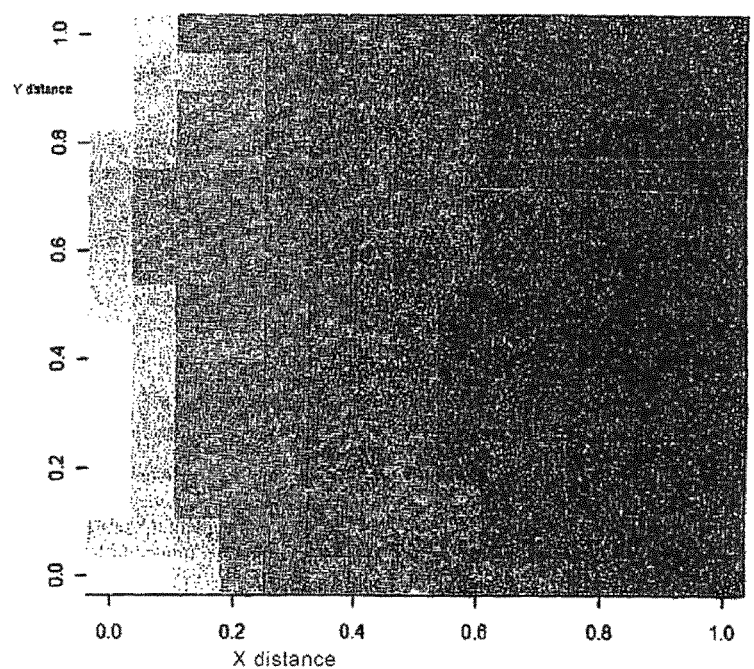
FIGS. 33A-33C show the output after fitting a Gaussian to focal scores obtained by an autofocus module of the invention.

For the above equations, z is the Z height in the image, and A, B, and C are parameters of the curve to be fit. Parameter A is the expected location of optimal Z. The fit is performed using a least-squares nonlinear fitting routine. In a preferred aspect, the Levenberg-Marquardt method is implemented because it performs well for stage forward kinematics. FIG. 33A shows example output after fitting a Gaussian to each focal score (using 15×15 focal scores with each block being summed). Units for X and Y distance is fraction of image. Lighter colored regions indicate a larger mean focal score. In this example, a somewhat linear trend in mean focal scores is observed increasing from right to left.

Figure 33B:
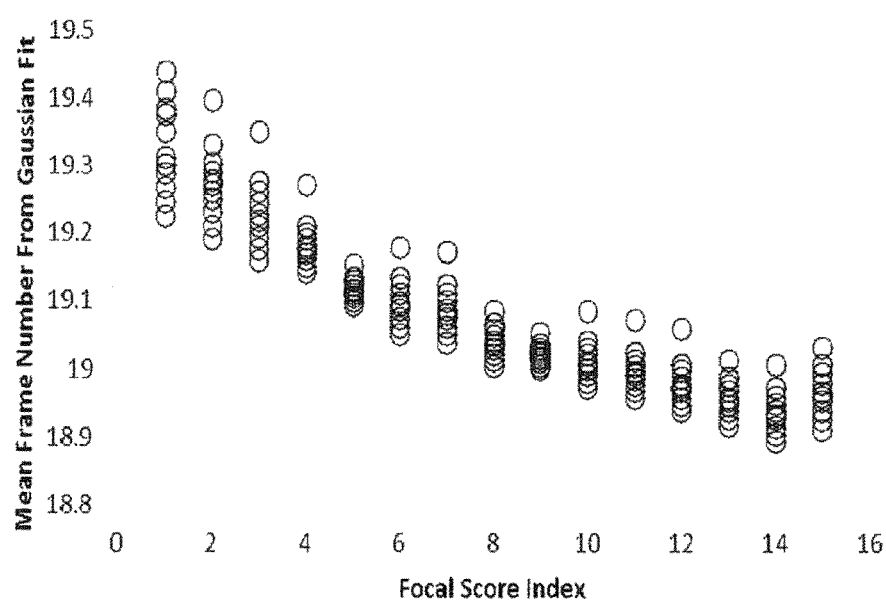
Figure 33C:
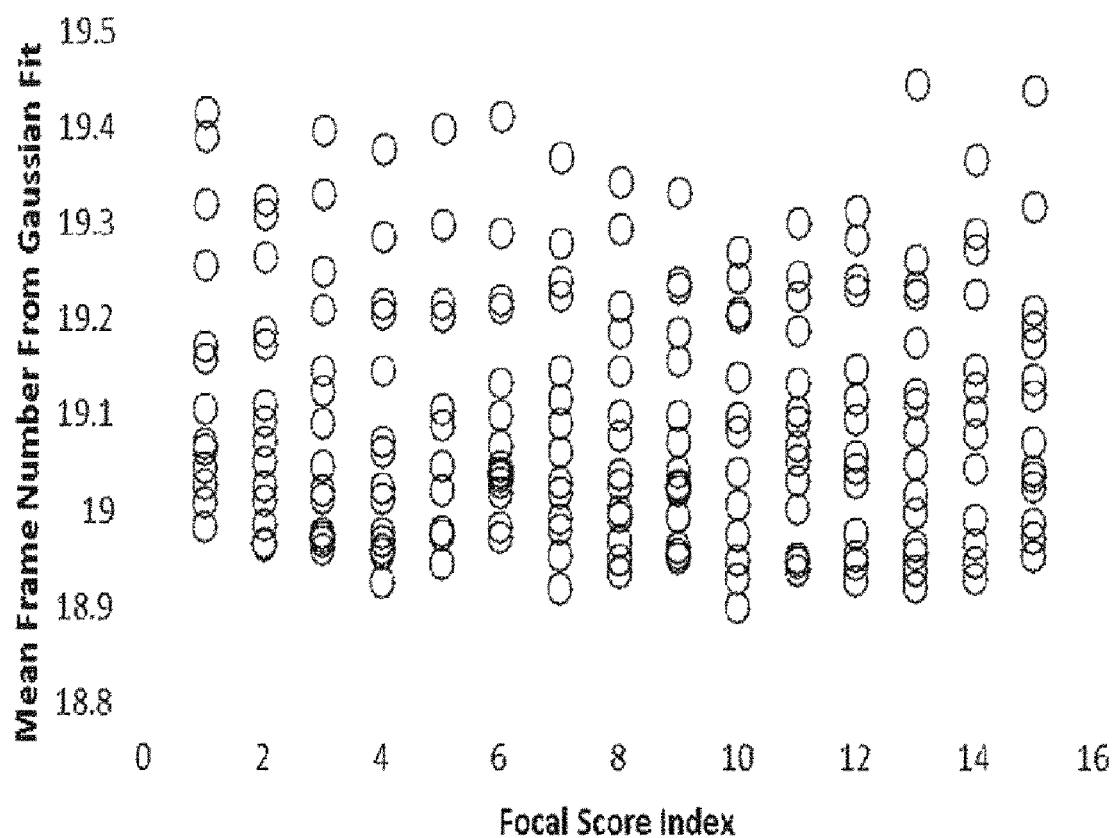

FIG. 33B shows a side view of the same example output as FIG. 33A. Numbers indicate the location in the perpendicular direction. Here, the focal score index is out of the 15 blocks within which the focal scores are calculated in the image. Frame numbers are indicated on the vertical axis, with each frame being separated by 1 µm. FIG. 33C shows the same example output as FIG. 33A, but viewed from the side opposite of that for FIG. 33B.

Figure 34A:
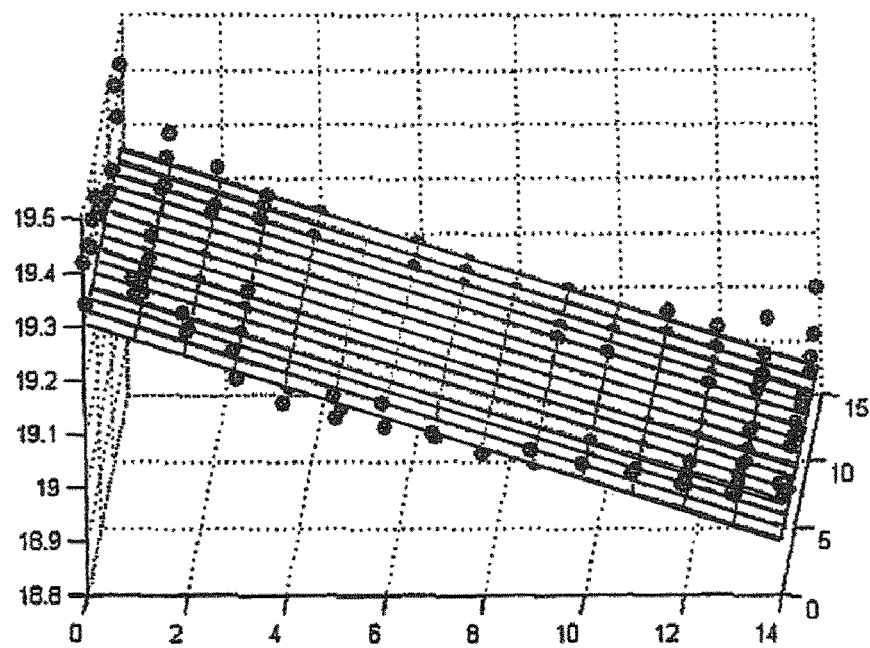
FIGS. 34A-34D show plane fitting data acquired from focal scores obtained by an autofocus module of the invention.
Figure 34B:
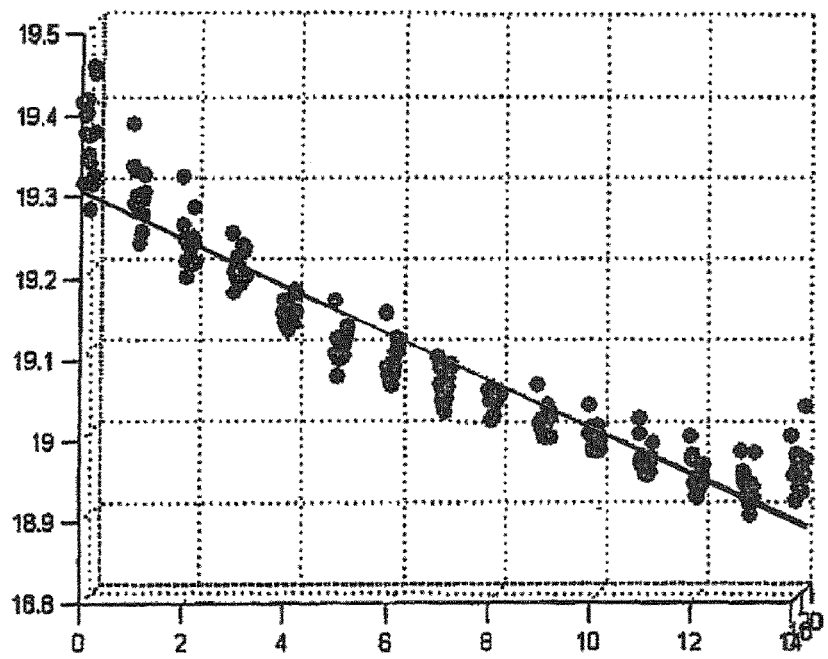
Figure 34C:
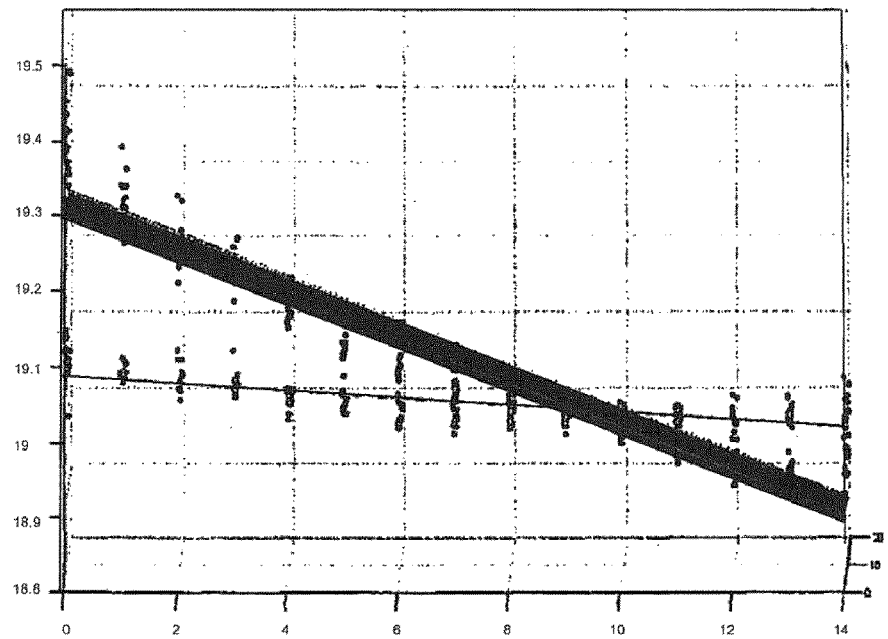
Figure 34D:
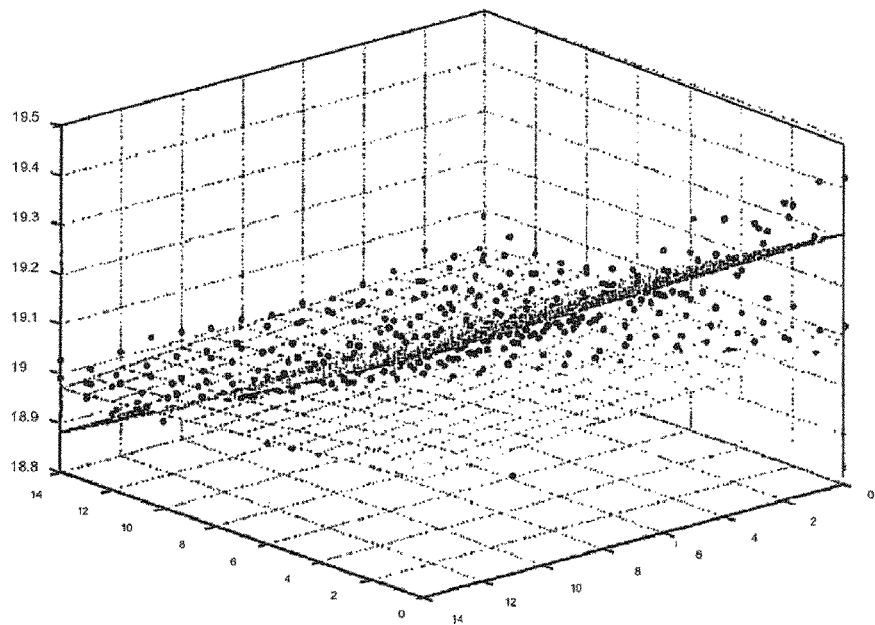

For plane fitting, linear regression can be applied to the data set used for FIGS. 33A-C above. FIG. 34A shows the best planar fit (mesh) to the data (circles). In this case, the substrate was not level. FIG. 34B shows the data of FIG. 34A viewed from the side. Fitted optimal focal score values for a leveled substrate (indicated by the flatter line) are added to the earlier plots, as shown in FIG. 34C. Horizontal axis labels are block number, which are 1/15th of the full image. As for the non-leveled substrate, the leveled substrate data was acquired from 40 Z locations separated by 1 µm. FIG. 34D shows a different view of the same data.

Figure 35A:
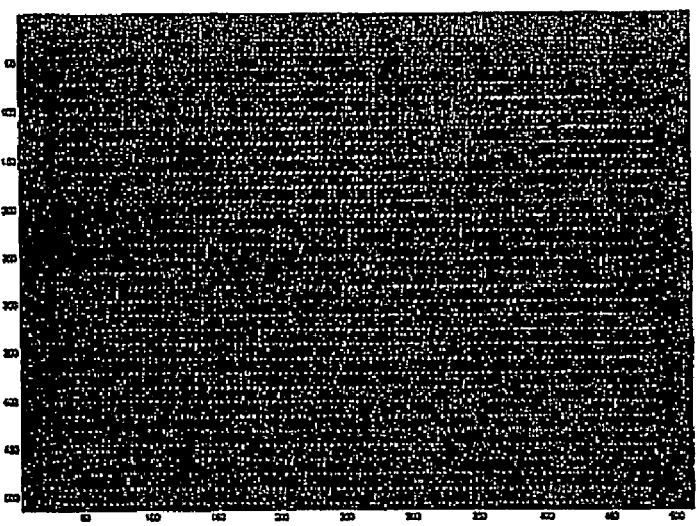
FIG. 35 shows images, captured using an autofocus module of the invention, of a plurality of optical signals emanating from a substrate.
Figure 35B:
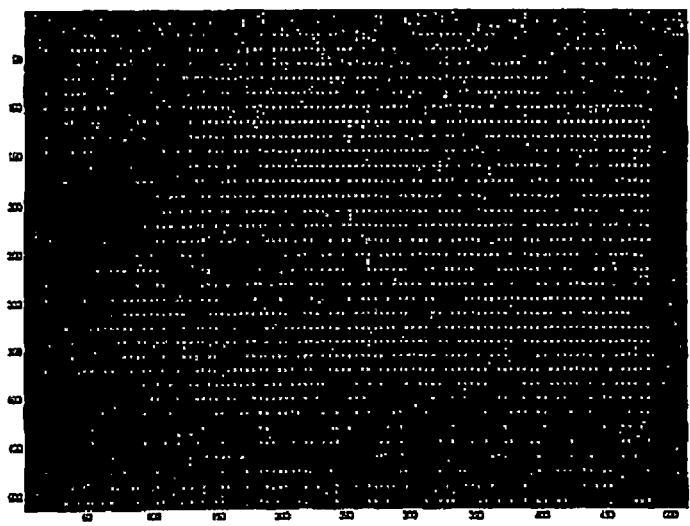
Figure 35C:
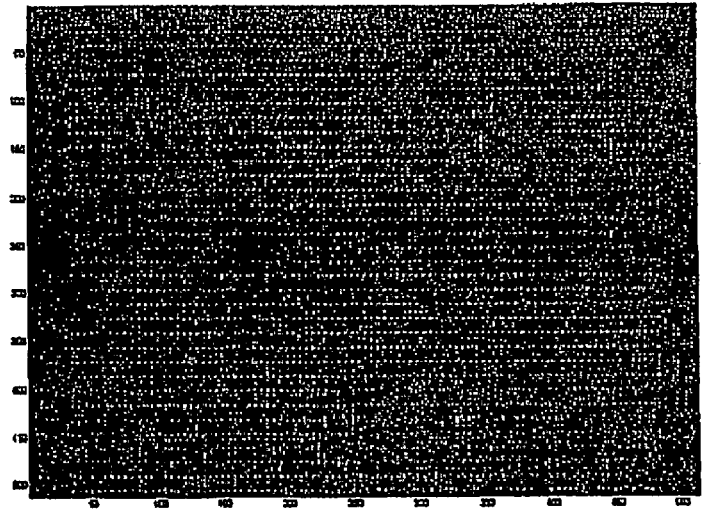

Images of a substrate captured by an optical detector are shown in FIG. 35. Panel I shows the Z stack frame prior to the frame closest to the optimal Z value for the leveled substrate. The stack frame closest to the optimal Z value for the leveled substrate is shown in Panel II. Panel III shows the Z stack frame after the frame closest to the optimal Z value for the leveled substrate. For the leveled data set, the optimal Z value did not change significantly between using 40 Z stack images versus using 6 images around the optimal focus plane.

E. Optical Systems for Reduced Autofluorescence Background Noise

Sources of background signals in fluorescent systems include signal noise that derives from the use of relatively high-intensity excitation radiation in conjunction with sensitive light detection. Such noise sources include those that derive from errant light entering the detection system that may come from inappropriately filtered or blocked excitation radiation, and/or contaminating ambient light sources that may impact the overall system. Other sources of signal noise resulting from the application of high intensity excitation illumination derives from the auto-fluorescence of the various components of the system when subjected to such illumination, as well as Raman scattering of the excitation illumination. The contribution of this systemic fluorescence is generally referred to herein as autofluorescence background noise (ABN).

It is desirable to provide substrate analysis systems in which background signal, such as autofluorescence background noise, was minimized. This is particularly the case in relatively low signal level reactions, such as single molecule fluorescence detection methods and systems. The present invention provides optical systems that have improved abilities to monitor fluorescent signals from analytical reactions by virtue of having reduced levels of background signal noise that derives from autofluorescence created within one or more components of the overall system.

In one embodiment, the invention provides optical systems with catadioptric microscope objective configurations for reduced autofluorescence. The objective is composed of three lens groups: a reflective mirror group; a dichroic mirror; and a refractive lens group. The reflective mirror group is composed of two asphere mirrors. These two mirrors are used to determine the first order system parameters, e.g., focal length and working distance, and also correct for third order aberrations within the specified field of view (FOV), such as 3rd order spherical aberration, 3rd coma, 3rd astigmatism, Petzval field curvature and distortion. Since they are mirrors, no chromatic aberration is introduced, e.g., if a point source is placed on the focal plane of the two-mirror system at any point within the FOV, the two mirrors generate a roughly collimated beam with a certain beam diameter.

The illumination light is introduced into the objective through reflection of the dichroic mirror. The illumination light then travels through the two mirrors and is focused onto the image plane, i.e., ZMW plane. Because the two mirror system is a low quality infinity corrected objective, any illumination patterns, such as a two dimensional dot array, line array, or flood illumination can be formed with the help of other optical elements (e.g., a diffractive optical element, diffraction grating, and the like) in the illumination path. The two mirrors generate very little autofluorescence, and in this regard, the catadioptric objectives of the invention are equivalent to pure reflective objectives The dichroic mirror is reflective to the illumination light but transmissive to the fluorescence light. Moreover, the substrate of the dichroic mirror can be made from highly pure fused silica, which generates little autofluorescence.

The refractive lens group consists of refractive elements and corrects for high order aberrations, e.g., 5th order aberrations. Therefore, the optical power of this lens group is very low. That is, the focal length of this lens group is very long. Optical elements and materials can be chosen to make the refractive lens group achromatic. Compared to a two mirror-based reflective objective, this refractive lens group provides additional freedom for the design. These additional freedoms make it possible to design high quality, large numerical aperture, and large field of view objectives.

The reflective mirror group and the refractive lens group should be positioned at a distance from each other such that the back focal plane of the reflective mirror group is located between the two lens groups. The aperture stop should be placed in close proximity to the front focal plane of the reflective mirror group. Because the refractive lens group has a very long focal length, the exit pupil (the image of the aperture stop by the refractive lens group) will be located close to the refractive lens group. In this configuration, telecentricity operation for both the fluorescence detection and illumination paths can be achieved.

Figure 36:
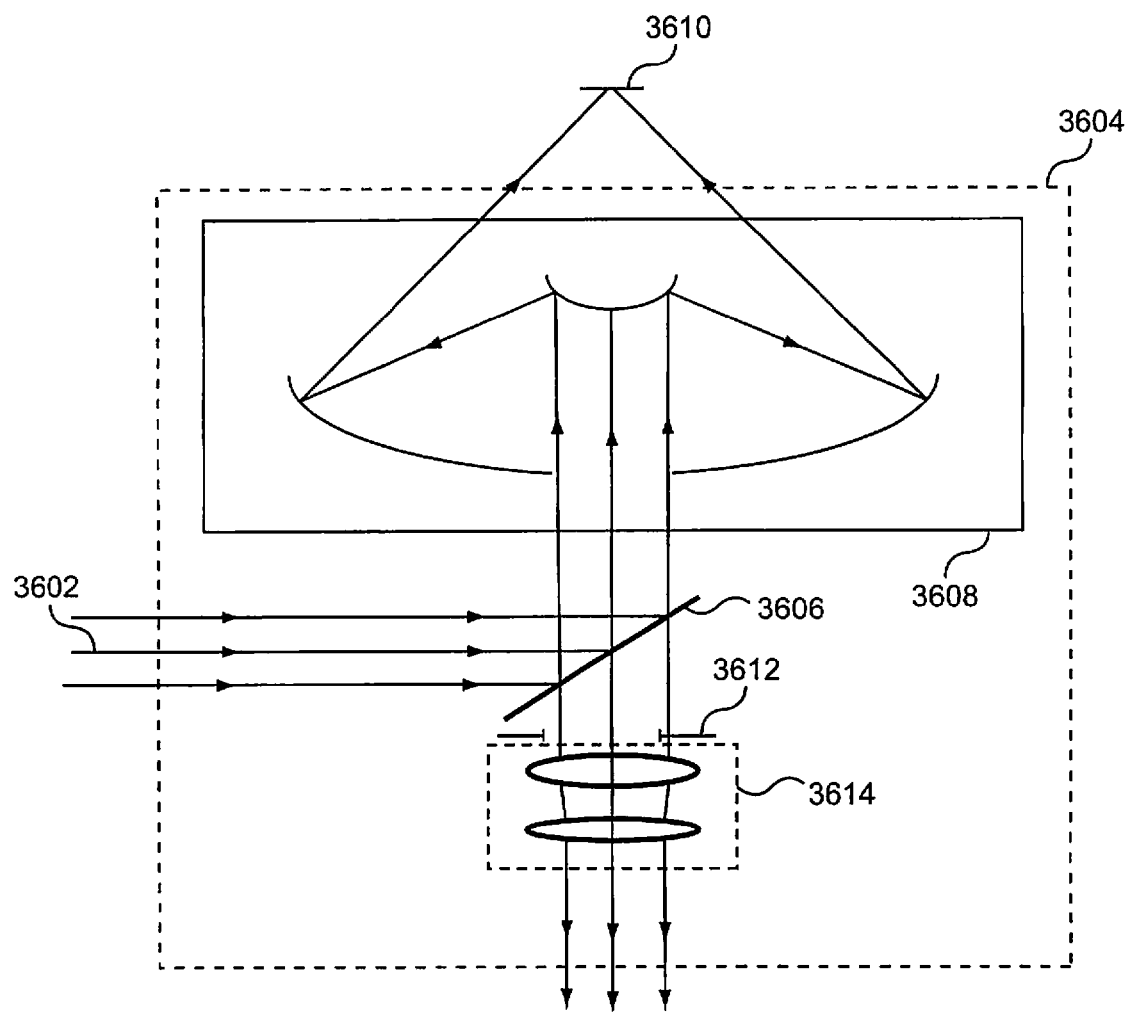
FIG. 36 is a schematic illustration of a catadioptric microscope objective configuration of the invention.

FIG. 36 schematically illustrates an example catadioptric microscope objective configuration in accordance with the present invention. As shown, beam of excitation radiation 3602 enters objective 3604, reflects off of dichroic 3606 and is directed into reflective mirror group 3608. The asphere mirrors of the reflective mirror group focus the excitation radiation onto reaction region plane 3610 of the substrate. Optical signals emanating from reactions regions of the substrate pass through reflective mirror group 3608 which is transmissive to the fluorescence, fluorescence transmissive dichroic 3606, aperture stop 3612, and refractive lens group 3614 for detection by one or more optical detectors. As a result, within the objective lens, there exists two discrete optical paths for the fluorescence radiation and the excitation radiation. By separating, at least partially, the excitation and emission paths, one can provide a path that has reduced autofluorescence that is directed back onto the detection system.

Other similar systems may be employed to achieve a similar goal of providing dual paths within the objective lens for the excitation and emission radiation, e.g., where the excitation light travels through a different portion or region of one or more lenses in an objective lens than the portion or region of such lens or lenses through which the emission light travels. For example, one may include a localized dichroic region within one or more of the lenses in the overall objective, such that excitation radiation is relegated to the periphery of the objective's optical path, while permitting collected emission radiation to travel through the central portion of the objective's optical path. By separating excitation and emission radiation, one could relegate autofluorescence associated with the excitation radiation to the excitation path, e.g., the periphery of the lens, which could be spatially filtered before impinging upon a detector, e.g., using a confocal pinhole or the like.

In another embodiment of the invention, the optical train is configured to transilluminate reaction regions of the substrate, whereby the illumination and detection paths reside on opposite sides of the substrate. As such, the illumination path does not share any optical components with the signal collection path, greatly reducing autofluorescence levels as compared to optical systems that provide excitation radiation and collect optical signals using shared components. Moreover, the system can take advantage of substrates that employ reflective layers for providing optically confined reaction regions disposed upon or within the substrate, e.g., a metal layer (e.g., an aluminum layer) of the substrate from which zero mode waveguides can be provided. Other than small (e.g., nanoscale) apertures in the metal layer, this layer prevents substantially all of the excitation radiation in the illumination path from entering the signal collection path, facilitating the collection of optical signals emanating from reaction regions of the substrate by optical detectors of the system. For optimal illumination efficiency, reaction regions (e.g., ZMWs) can optionally be made with two layers, a metal layer and a dielectric layer, the thicknesses of which can be chosen for optimal evanescent wave intensity, minimizing photodamage to certain analytic reagents, and optimal confinement of such reagents within the reaction regions.

Figure 37A:
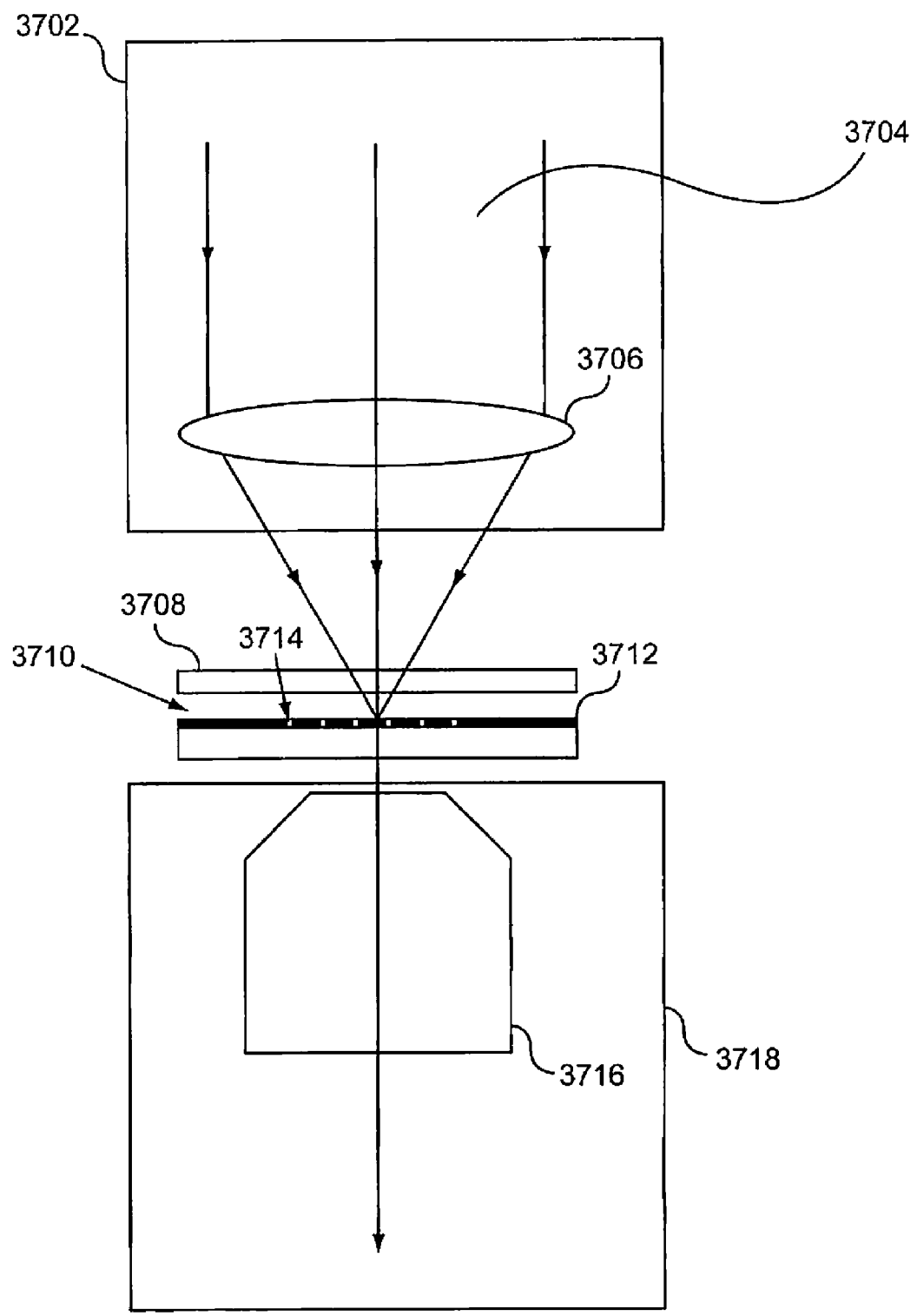
FIG. 37 schematically illustrates a transillumination optical train configuration of the invention.

An example transillumination and detection system is schematically illustrated in FIG. 37A. In illumination path 3702, one or more sources of transmission excitation radiation excitation radiation directs excitation radiation, e.g., laser beam 3704, which is focused by condenser lens 3706 through sealing glass 3708 and solution layer 3710 onto a plane coinciding with a layer of a substrate where analytic reactions occur, e.g., ZMW layer 3712. One or more ZMW, e.g., ZMW 3714, is disposed within ZMW layer 3712, which can be made of a metal, e.g., aluminum, or can comprise two layers, e.g., a metal layer and a dielectric layer (e.g., $SiO_2$). In a preferred aspect, a highly multiplexed array of reaction regions are provided in the layer of the substrate where analytic reactions occur, e.g., thousands, tens of thousands, hundreds of thousands, or even millions of reaction regions. Optical signals emanating from reagents within the reaction regions are collected by objective 3716 in collection path 3718 on a side opposite illumination path 3702, relative to the substrate. The optical signals exiting objective 3716 can be collected by one or more signal detectors of the system.

Figure 37B:
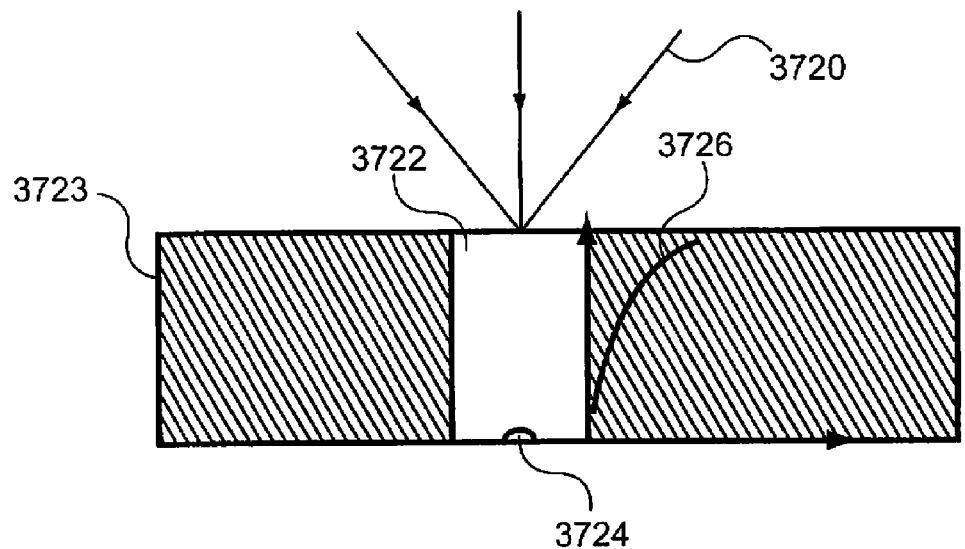

In addition to substantially eliminating autofluorescence background noise, the transillumination configurations of the invention provide other benefits as well. For example, transillumination can reduce photodamage to light-sensitive reagents within reaction regions of the substrate. This principle is schematically illustrated in FIG. 37B. As shown, illumination light 3720 illuminates a reaction region, e.g., ZMW 3722 disposed through metal layer of substrate 3723 from a side opposite where certain light-sensitive reagents, e.g., polymerase 3724 are disposed. Plot 3726 of the intensity of an evanescent wave entering ZMW 3722 indicates that the amplitude of the evanescent wave becomes weaker as it reaches the portion of the ZMW where polymerase 3724 resides. The horizontal axis (right-pointing arrow) represents electromagnetic (EM) field intensity, while the vertical axis (upward-pointing arrow) indicates depth of the ZMW. As such, the activity can be significantly prolonged for reagents situated in a portion of the reaction region opposite the side through which the evanescent wave enters.

Figure 37C:
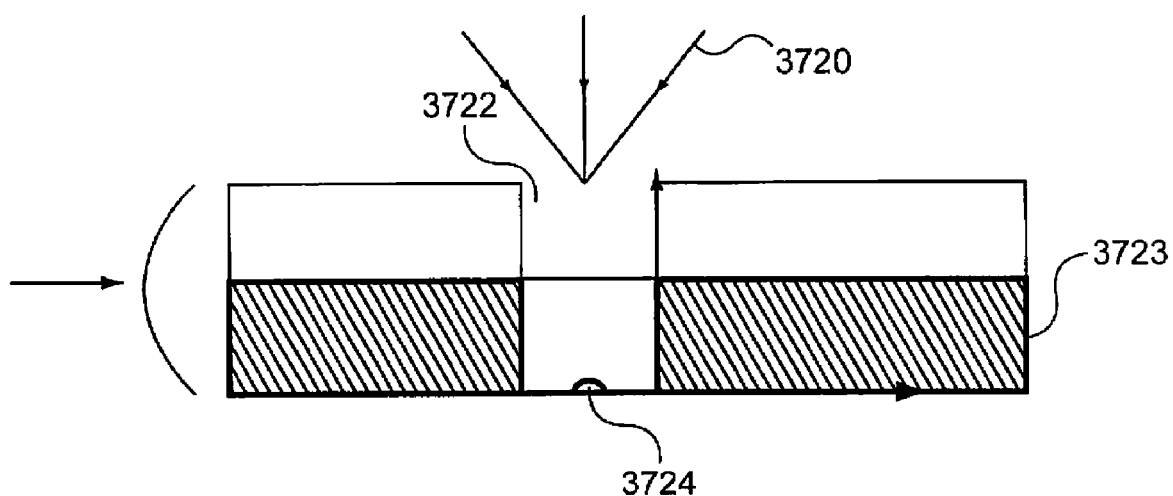

As described above, the reaction regions can be provided in a bilayer of the substrate for enhanced illumination efficiency, where one layer is made of an opaque material, e.g., a layer made of metal (e.g., Al) and the other layer is made of a transparent dielectric material (e.g., SiO2). The transparent dielectric material is present to provide sufficient depth to the reaction region for structural confinement of reagents therein. The thickness of the opaque layer can be chosen to provide the optimal evanescent wave intensity at the portion of the reaction region where illumination is most desirable. An example reaction region bilayer is schematically illustrated in FIG. 37C. As shown, transparent dielectric layer 3728 is provided on the side of bilayer 3730 from which the source of excitation radiation 3702 resides. Opaque layer, e.g, metal layer 3723 is provided on the opposite side with respect to the excitation radiation source.

F. Optical Detectors

The systems of the invention may generally include any of a variety of different detector types useful for detecting optical signals that are directed to the detector. Examples of different types of detectors include photodiodes, avalanche photodiodes, photomultiplier tubes, imaging detectors, such as charge coupled devices, CMOS (complementary metal oxide semiconductor) sensors or imagers, CCD/CMOS hybrid imagers, and the like. In preferred aspects, imaging detectors are employed in the systems of the invention, so as to provide simultaneous detection over larger areas of the substrates, and consequently, larger numbers of discrete signal sources. Charge coupled device based detectors (CCDs) and CMOS image sensors are particularly preferred for their ability to simultaneously detect and/or monitor signals from large numbers of discrete signal sources on the substrate. Because data derived from these types of image or imaging detectors is assigned to discrete pixels, signals from discrete sources that are incident upon different locations of the detector may be separately detected and quantified. Further, in applications where relatively high speed, and relatively low signal levels are prevalent, e.g., where the signal sources comprise single molecule type reactions, highly sensitive detectors are generally preferred, such as electron multiplying CCDs (EMCCD) or intensified CCDs (ICCD). Typically, EMCCDs or CMOS image sensors are preferred for their sensitivity to low signal levels. Further details regarding optical detectors that find use with the substrate analysis and optical systems of the invention can be found in International Publication No. WO/2007/095119 by Lundquist et al. entitled "METHODS AND SYSTEMS FOR SIMULTANEOUS REAL-TIME MONITORING OF OPTICAL SIGNALS FROM MULTIPLE SOURCES", the full disclosure of which is incorporated herein by reference in its entirety for all purposes.

Figure 38:
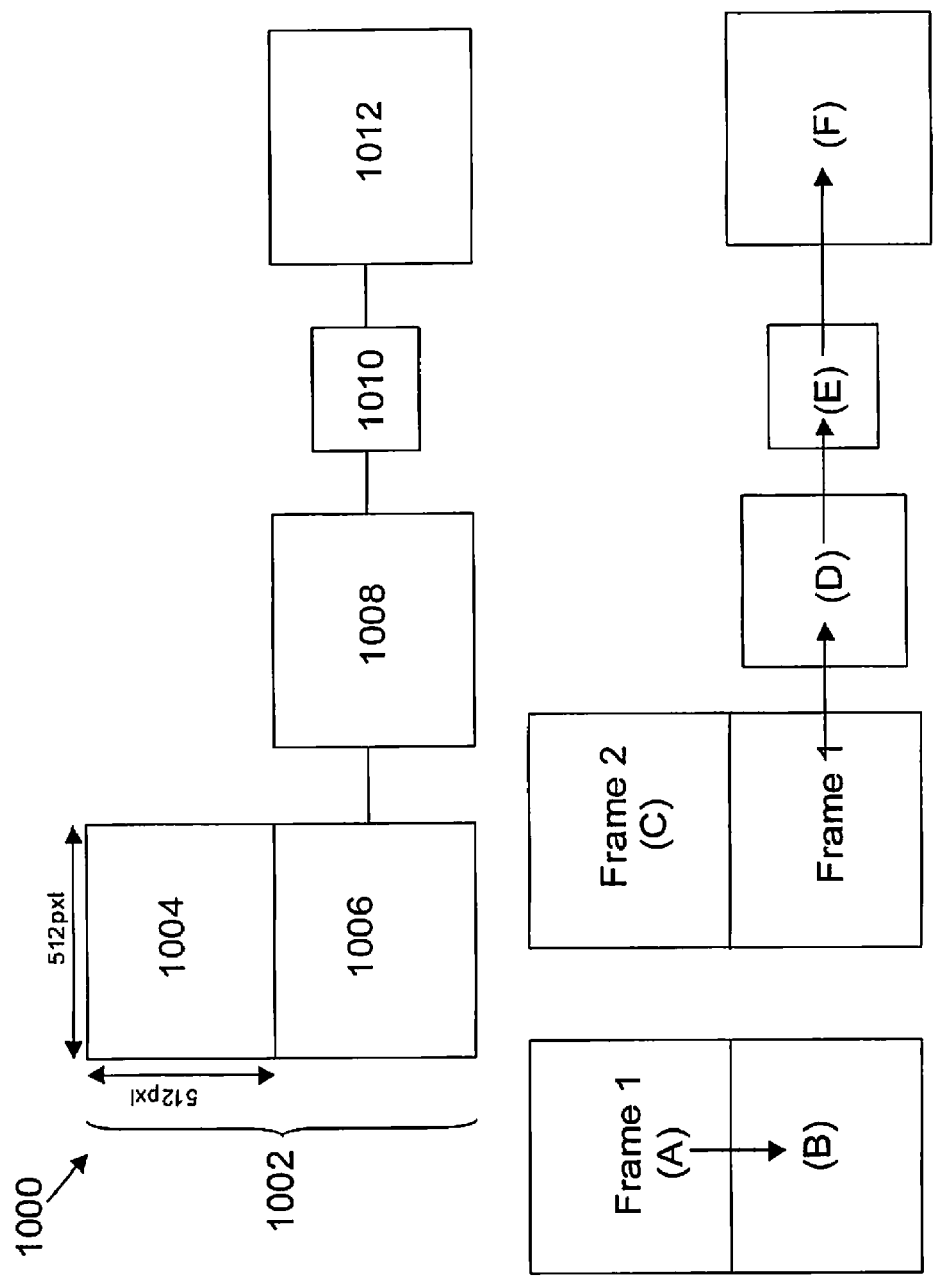
FIG. 38 provides a block diagram illustrating the operation of an EMCCD detector and data processing steps of certain aspects of the invention.

FIG. 38 provides a schematic illustration of the operation of an exemplary EMCCD in processing image data. As shown, an overall system 3800 includes a typical EMCCD chip 3802, which has an image area 3804 and a storage area 3806. The CCD includes an EM gain register 3808 that is operably connected to an appropriate analog:digital converter 3810, which is, in turn, connected to a processor or computer, e.g., computer 3812. As shown, each area comprises a 512× 512 pixel array. As shown in step A, an image is acquired (Step A) (Frame 1) in the image area 3804 and transferred to the storage area 3806 (step B) so that the image area is available for acquiring subsequent images, e.g., Frame 2 (Step C). In the case of some EMCCDs, the frame transfer requires an applied potential of approximately 2V. The frame in the storage area (Frame 1, as shown) is then transferred into the EM Gain register 3808 pipeline (step D) (again, requiring approximately 2V), where the charge associated with the image is passed through approximately 536 stages to achieve a potential gain range, that is software controllable, from 1 to of 2000×. The EM gain register processing typically requires approximately 50V. The amplified image data is then passed through an analog to digital converter 3810 (step E) to be stored or further processed by a computer 3812 (step F).

As with the illumination of signal sources, in preferred aspects, the detection systems in the systems of the invention are typically capable of detecting and/or monitoring signals from at least 2 different signal sources, simultaneously, preferably, at least 1000 discrete signal sources, and in many cases, more than 10,000, more than 50,000 (e.g., 80,000), more than 100,000, or even more than 1,000,000 discrete signal sources, simultaneously. Further, the detectors are likewise capable of monitoring or detecting multiple, spatially separated signals or signal components from each such source. In particular, as noted above, signals from each discrete source are preferably spatially separated, at least partially, into at least two, and preferably, three, four or even more separate signal components, that are directed onto the detector array and are capable of resolution and ultimately being separately detected. In some cases, two different signals that may be emitted from a given signal source may not be completely spatially separable onto different regions of a detector array. However, because such signals differ in their emission wavelength spectra, subjecting such different signals to the wavelength separation components of the optical train, e.g., a prism such as prism 910 in FIG. 9, can yield imaged signals on a detector array that have imaged shapes that are characteristic of the particular emission spectrum, while not being completely spatially separable from another signal components having slightly different emission spectra. In such cases, identifying the signal component that gives rise to a detectable event can sometimes include identification of a characteristic shape of an aggregate group of pixels upon which such signal is incident. As will be appreciated, in those cases that utilize detector arrays as image detectors, e.g., CCDs, CMOS sensors, and the like, detection of image shape will typically refer to detection of signals at the various detector elements, or pixels, that are reflective of an imaged signal of a given shape. Thus, identifying a signals imaged shape will generally refer to detection of signal at pixels underlying that image shape, rather than holistically identifying the shape. Further, the identification of the signal component based upon the imaged shape may not specifically include a step where the shape is identified, but rather that signal is detected that is characteristic of that shape. Thus, with respect to these methods, identification of image shape may not include any step whereby the shape is actually identified, e.g., "shape is circular", but may only be identified by the identification of the pixels upon which the signal is incident.

X. Signal Analysis Modules and Data Management

The systems of the invention also typically include a signal analysis module (e.g., a data processing system) coupled to the one or more detectors for processing and/or recording signals that are incident upon and detected by the detector, and for processing that data to useful information for the user. For example, in the case of single molecule analyses, e.g., where the signal source comprises fluorogenic reactants, the data processing system may assign a value to the incidence of signal on a given location of the detector at a particular time, as being indicative of the occurrence of a given reaction. The data derived from each signal would typically include one or more of (a) the intensity of the signal, (b) the pixel or pixels upon which the signal was incident, (c) relative time that the signal was detected, and the like. Such data may then be processed to indicate relative rates or activities of reactants, order of reactions, a particular signal source from which the signal was derived, and through knowledge of that source's reactants, the nature of an analyte exposed to such reactants.

For ease of discussion, where the signal source includes template directed DNA synthesis using fluorescent nucleotide analogs and DNA polymerase enzyme within an optical confinement, a signal may be indicative of the incorporation of a nucleotide at a given relative position in the synthesis. Further, using the spectral separation aspects of the optical train, and four different nucleotide analogs all bearing dyes or labels having resolvably different spectral characteristics, e.g., that are separated by the optical train and directed to different locations on the one or more detectors (or that possess different imaged shapes) as a result of their differing spectral characteristics, a signal at a given location on the detector (or having a given shape) can be indicative of incorporation of a specific type of analog, and the relative timing of such signal would be indicative that such base occurs in the template sequence before or after another base which gave rise to an earlier or later signal, respectively. Finally, the location on the array where such signals are incident is indicative of the signal source from which the signals derive (e.g., indicating that subsequent signals at the same approximate location (subject to, e.g., spatial separation based upon spectral differences of components of signals from a given source) are likely a result of the continuation of the same reaction). This detection is repeated multiple times to identify the sequence of incorporation of multiple nucleotides. By virtue of the complementarity of incorporation in template directed DNA synthesis, one may then ascertain the underlying sequence of nucleotides in the template sequence. Further details regarding the management of optical signal data can be found in International Publication No. WO 2008/154317 by Maxham et al. entitled "METHODS AND PROCESSES FOR CALLING BASES IN SEQUENCING BY INCORPORATION METHODS", and International Publication No. WO 2007/095119 by Lundquist et al. entitled "METHODS AND SYSTEMS FOR SIMULTANEOUS REAL-TIME MONITORING OF OPTICAL SIGNALS FROM MULTIPLE SOURCES", the full disclosures of which are incorporated herein by reference in their entirety for all purposes.

One may also adjust the methods by which data is acquired and/or assigned to individual sources, based upon those expected optical aberrations. In particular, as noted previously, an amount of distortion of an imaged array can increase as a function of distance from the axial center of the object field. As a result, correlating or assigning individual pixels or groups of pixels to a specific signal source in an imaged array becomes more difficult away from the center of the image. Additionally, optical aberrations may further deform the shape of the imaged signal depending upon the position on the detector array of the imaged signal. For example, certain optical aberrations, i.e., coma, may yield an imaged signal from a circular source that is 'tear-drop' shaped, falling away from the axial center of the imaged field. Alternatively, combinations of astigmatism and field curvature could result in an elliptical signal image shape from a circular signal source, which is more pronounced with increasing distance from the axial center of the object field.

Figure 39B:
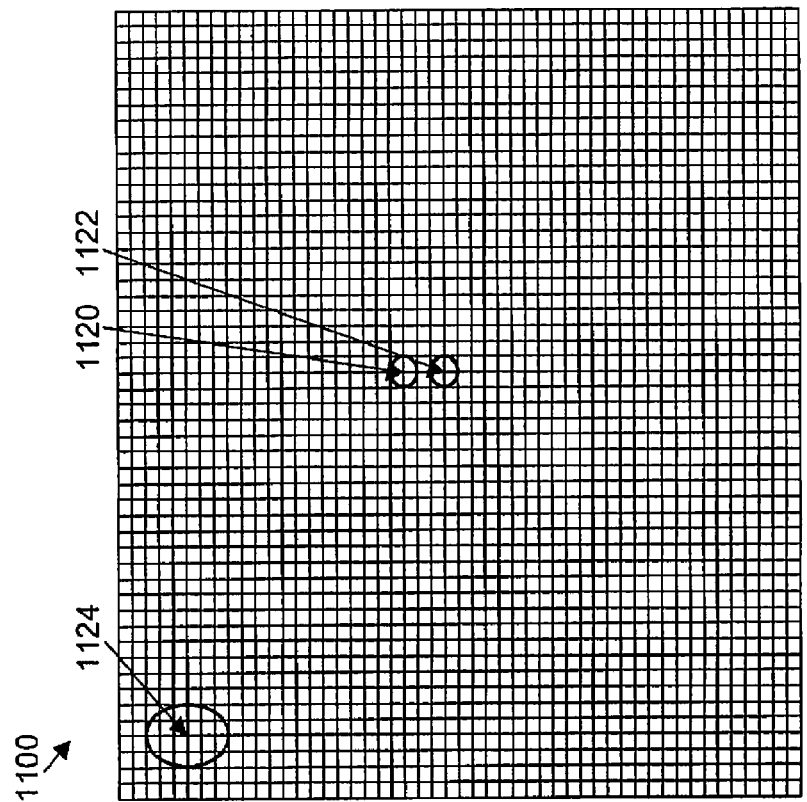
FIG. 39 provides a comparative illustration of signal image correlation methods from a detector array that take into account optical aberrations in the upstream optical train.
Figure 39A:
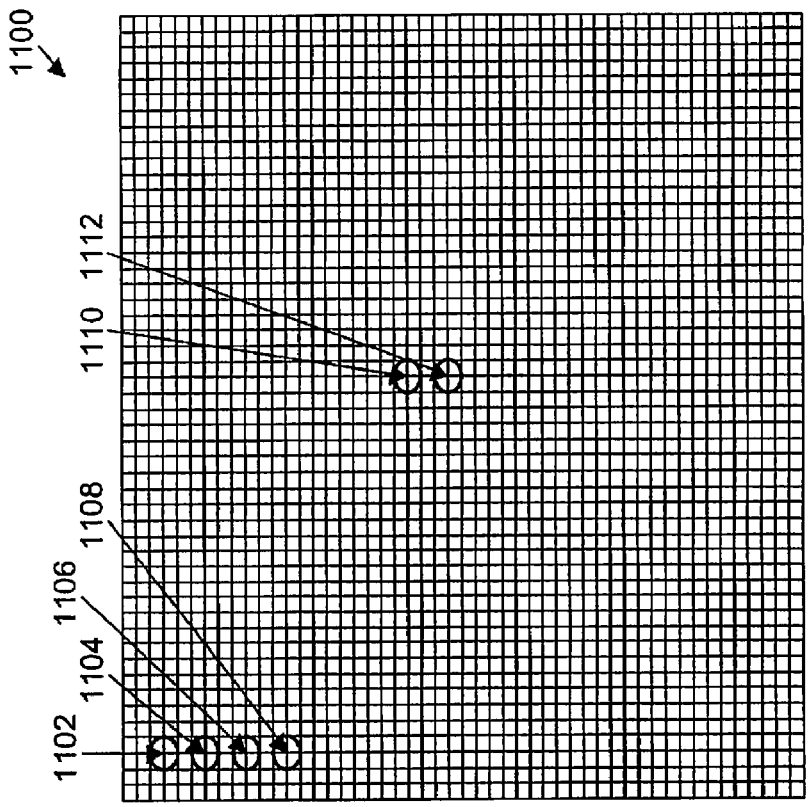

Accordingly, one can accommodate increasing levels of distortion by expanding the number of pixels that are correlated to any given source, in conjunction with a known or expected optical aberration of the system. In a simple form, this involves increasing the number of pixels correlated to a given source being imaged as that image (or its respective image source) is farther away from the center of the image or object field. A schematic illustration of this is shown in FIG. 39. As shown, an array of pixels in an array detector, e.g., a CCD 3900, is provided to image the array of signal sources. As shown in panel A, in the absence of optical aberrations, uniform signal sources yield uniform images upon the CCD, e.g., as indicated by signals 3902-3912, regardless of where in the image field they emanated from. However, in the case of systems sensitive to such optical aberrations, as the distance increases between the center of the imaged field and a given imaged source, e.g., moving from imaged spots 3920 and 3922 to spot 3924, the distortion results in increasing image size, and/or lower resolution. In order to account for this distortion, the pixels correlated to a given image or signal are increased to maximize the data acquired for each imaged signal, e.g., by acquiring as much of the given signal as possible or practicable, e.g., including all of the different pixel regions at the center and periphery of the object field, imaged onto the CCD. The adjustment of correlated or recorded pixels for any given signal image is a particularly useful process when combined with an array of sources that is further arranged to account for such optical aberrations, e.g., see FIG. 3, above. Alternatively, or additionally, and also as shown in FIG. 39, one may adjust the assigned pixels for a particular imaged signal to account for distortions in the shape of the imaged signal, e.g., for an elliptical or tear-drop shaped image. In particular, one may employ a collection of pixels for an individual imaged signal that is larger in one axis than the other, e.g., longer in the y axis as shown in FIG. 39.

In addition to the improved ability to separately monitor signals from discrete sources, the use of such CCD or other array detectors provides additional benefits for analysis of signals from the individual signal sources as well as the aggregate signals from the overall array of signal sources. For example, where a signal from a given discrete source is incident upon multiple pixels, the compartmentalization of data on a pixel basis allows selection of optimal pixels in a given imaged signal, for data analysis, e.g., eliminating edge signals that may have higher levels of noise or distortion. Additionally or alternatively, pixels used to obtain signal data for each discrete signal source may be individually tailored for a variety of different purposes, as discussed elsewhere herein. The management of such pixel data is further described in greater detail below.

In addition to accommodating and/or correcting for optical aberrations, the present invention also provides processes that provide more efficient processing of relevant signals. In at least one general aspect, such processes involve the further processing of only relevant signals, while either discarding or combining less relevant signals. In either case, by reducing the amount of signal data that is subjected to the full range of further processing, one can speed up that processing, reduce processing requirements, e.g., computing power, reduce real estate on an array detector required for image data management, extend the lifespan of detector components, and achieve a variety of other benefits. These processes generally may be carried out either in the context of the CCD chip, or they may be performed in a subsequent, off-chip processes, e.g., using a computer. As will be appreciated, in many cases, preferred implementations are carried out within the image data processing steps on the detector array itself.

In the context of the present invention, it will generally be understood that the term "processing" refers to automated processing of data by a mechanical or solid state processor or system that is programmed to carry out such processes, e.g., in machine readable software or firmware. Thus, the processing steps may be carried out by a single solid state device, e.g., an appropriately configured detector chip such as an EMCCD, or by a connected or integrated computer or other processor.

As alluded to above, in certain aspects, the invention provides for an initial data processing or selection step to avoid the management, storage and/or processing of excessive irrelevant data that is or would be produced by the detection system, as well as the combined processing of certain data from different areas on the detector. In particular, in some cases, one may gain significant advantages, e.g., in terms of speed of data processing and management and usefulness of background signal data, through the selective skipping, removing, or combining of pixel data prior or subsequent to extraction of data, e.g., from a CCD chip. Stated in another way, by ignoring or separately processing data collected from certain pixel areas that do not contain highly relevant data, e.g., they fall outside of a relevant imaged signal, one can speed up the data management process by removing large amounts of irrelevant data from the process or combining into one processible unit, all of the background or less relevant signal data. Additionally, or alternatively, such combined less relevant pixel data may be useful to derive more meaningful background signal levels, or noise, of the system. In either case, the speed and accuracy of the system should benefit.

By way of example, where one is imaging a large number of discrete signal sources or separated signals derived from such sources, on a single detector array, e.g., a CCD, ICCD or EMCCD, space between imaged signals from such discrete sources gives rise to little or no useful data, as it is a "quiet" space. Notwithstanding the lack of useful signal data emanating from these regions of the detector array, the data from such locations has typically been recorded, e.g., as a zero, or some other low level signal value, or other irrelevant value. While such signals can be disregarded as background, their recordation and processing to the point of discard still requires memory space for storage and processing capacity for evaluation and ultimate discard. Accordingly, in certain aspects, the invention provides a masking process for filtering out such quiet locations on the detector array, and thus blocking the data from being recorded.

Figure 40B:
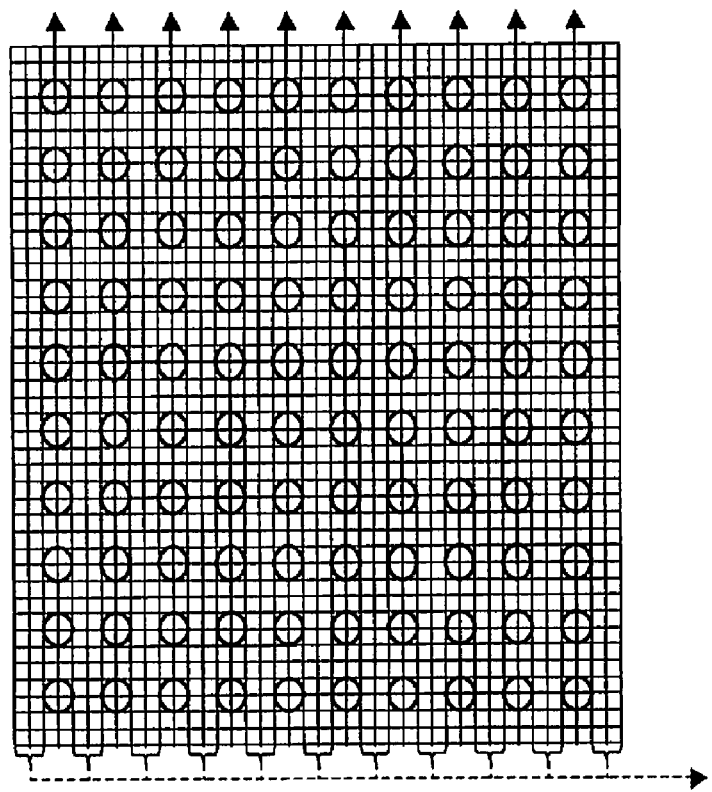
FIG. 40 schematically illustrates a comparison of data extraction processes in conventional image processing versus processes employed in certain aspects of the invention.
Figure 40A:
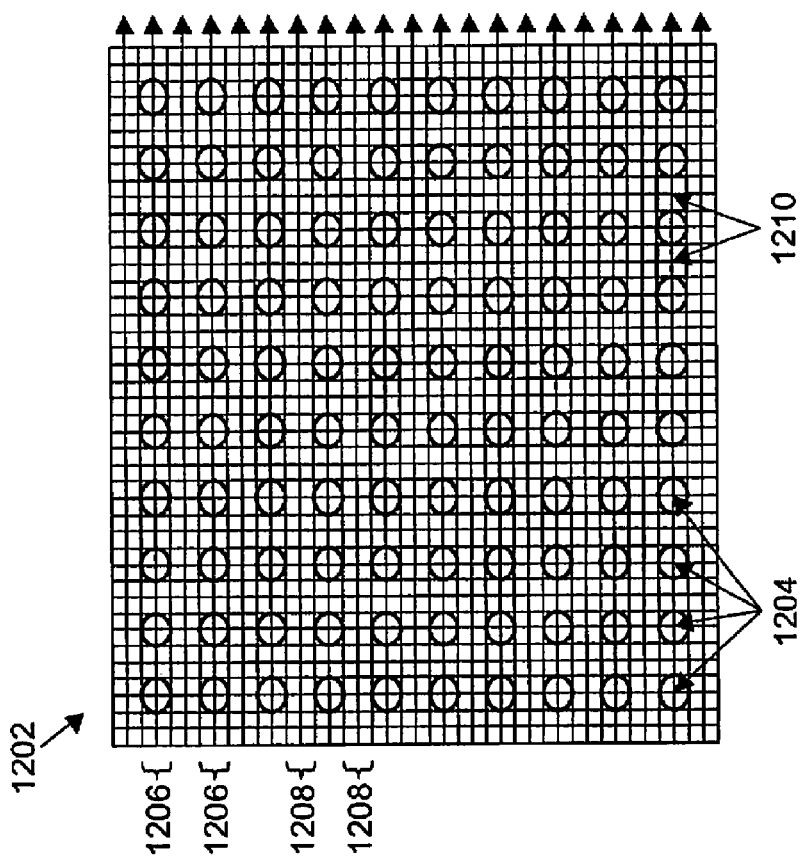

For example, in a first aspect, rows of detector array elements, such as pixels in CCD based detectors, that fall between rows of imaged signals from the discrete signal sources, and thus carry signals that are not as relevant to the desired analysis, may be skipped during data extraction from the detector arrays. FIG. 40 provides a schematic illustration of this data extraction profile in a CCD array. As shown, individual signals 4004 from signal sources (not shown) are imaged onto an array detector, e.g., CCD 4002. As shown, the imaged signals 4004 are imaged upon rows of pixels 4006 that are interspersed with rows of pixels 4008 upon which no relevant signals are being imaged, also generally referred to as "quiet pixels". As will be appreciated, within each row of pixels 4006 upon which are imaged relevant signals, there may exist quiet pixels between each individual imaged signal element, e.g., pixels 4010. For ease of illustration and discussion, the extraction of data from pixel rows and/or columns is generally illustrated with respect to pairs of adjacent rows and/or columns, rather than from individual pixel rows, but such illustration is not indicative of any process requirement or other parameter.

In a typical image extraction process, all of rows 4006 and 4008 would be subjected to the same processing steps, resulting in a substantial amount of resources being dedicated to the processing of the less relevant or quiet pixels. This is schematically illustrated by the arrows emanating from each pixel row (or pair of pixel rows, as shown), e.g., relevant signal rows 4006 and quiet pixel rows 4008.

In accordance with certain aspects of the invention, and as shown in the image in panel B, however, data is extracted from the pixels, e.g., the rows and/or columns that carry imaged signals, e.g., rows 4006, from an array of signal sources, while the intervening rows and/or columns, e.g., rows 4008 (and optionally quiet pixel columns that include, e.g., pixel regions 4010) are ignored from a data extraction standpoint. This is shown in FIG. 40, panel B.

In particular, as shown, an application of the process would involve skipping extraction of data from rows 4008, while extracting data from rows 4006. While data from the analyzed rows is subjected to further processing, e.g., passed through EM gain register and/or the analog-digital converter (ADC), to the computer or processor for subsequent storage and manipulation, the skipped rows are not. This effectively reduces the amount of data that is run through the ADC by more than half, in the example shown. Alternatively or additionally, the data derived from rows 4008 may be separately combined and/or averaged prior to or subsequent to extraction (shown by the dashed arrow in panel B) to provide a more significant determination of background noise levels of the system, which may then be used to further correct the signal data extracted from, e.g., rows 4006. Even with such processing of the quiet pixel data, by binning this data together for processing in a single processible data unit, the efficiencies described above are largely retained.

In other aspects, data from related array elements may be combined or "binned" before being subsequently processed, in order to minimize the number of separate data elements that are subject to processing. For example, with reference to the extracted row data described above, each set of rows and/or columns that corresponds to a particular signal source image, or the space between imaged signal sources, may be separately binned for subsequent processing, reducing the number of data elements that are subjected to processing. Similarly, pixels corresponding to images from individual signal source array elements may be binned together and processed. In each of the foregoing cases, whether alone or in combination, the overall number of data elements is substantially reduced over the extraction and processing of each individual pixel element.

In addition to providing benefits of data management selectively binning pixels of imaged signal components may provide advantages of data analysis. For example, when imaging spatially separated signal components, one can selectively bin those elements that are derived from signal rows that are of similar fidelity, allowing subsequent identification of lower fidelity signals, in aggregate. As noted previously, in certain embodiments, the constituent elements of each signal, e.g., the different signal wavelengths emanating from each signal source, are subjected to spatial separation and are imaged onto different pixels, or collections of pixels, on the detector array. As will be appreciated, because constituent signal wavelengths tend to fall over a range rather than within a precise single wavelength or wavelength range in some cases, and because addition of more signal wavelength components within the signal sources as may occur with various applications and/or multiplexing, spatial separation may yield less than complete separation between different signal constituents along each row, e.g., resulting in spectral overlap of the separated signals.

Figure 41A:
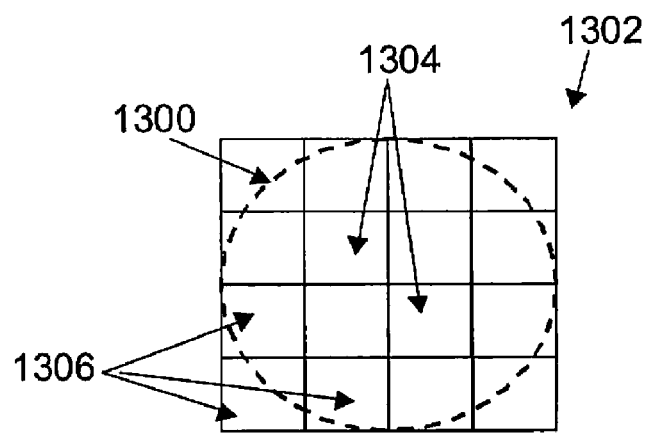
FIGS. 41A and 41B schematically illustrate pixel correlation to imaged signals or signal components to improve the fidelity of data from a given image or set of images.

In accordance with certain aspects of the invention, data that is of higher fidelity is processed separately than lower fidelity data, even within an imaged signal. In its simplest sense, only pixels that correspond to the highest fidelity data, e.g., having the highest intensity relative to a noise level of the system, are processed as relevant signals. Other signal components are then subjected to different processing or are discarded. In general, as will be appreciated, such signal components are those that are within the main portion of the imaged signal, e.g., toward the center of the imaged signal, rather than at its periphery. An example of this is illustrated with reference to FIG. 41A which shows a representation of an imaged signal 4100 upon a set of pixels 4102 in an array detector. In accordance with the signal selection processes described herein, only those signals derived from pixels at or near the central portion of the imaged signal, e.g., pixels in region 4104 (shown without hatching) are subjected to processing as relevant signal data. Signals from pixels at the periphery of the signal, e.g., pixels in region 4106 (shown cross hatching), would be expected to be of lower fidelity, e.g., having lower signal to noise ratios. Accordingly, pixels in region 4104 are subjected to processing as relevant signal while pixels in region 4106 are treated separately which may include discarding or inclusion in determination of an overall system signal to noise ratio. As will be appreciated, the selection of higher confidence signal data or their respective pixels may be carried out by a number of parameters including without limitation, selection of higher intensity signals within an overall imaged signal, and/or selection of signals that are expected to be of higher confidence based upon their position in an overall imaged signal, e.g., they fall within a central portion of the overall imaged portion, where the central portion refers to a signals from a subset of pixels impinged upon by the overall imaged signal, while pixels that are within the overall imaged signal, but fall at the periphery or around the entire edge of the imaged signal, are discarded. For generality, it could be viewed that the signal portion that extends only a portion of the radius of the overall imaged signal, would be viewed as of high confidence, where that portion may vary from, e.g., 25%, to 50% to 75% or even 90% where signal images are highly coherent.

Figure 41B:
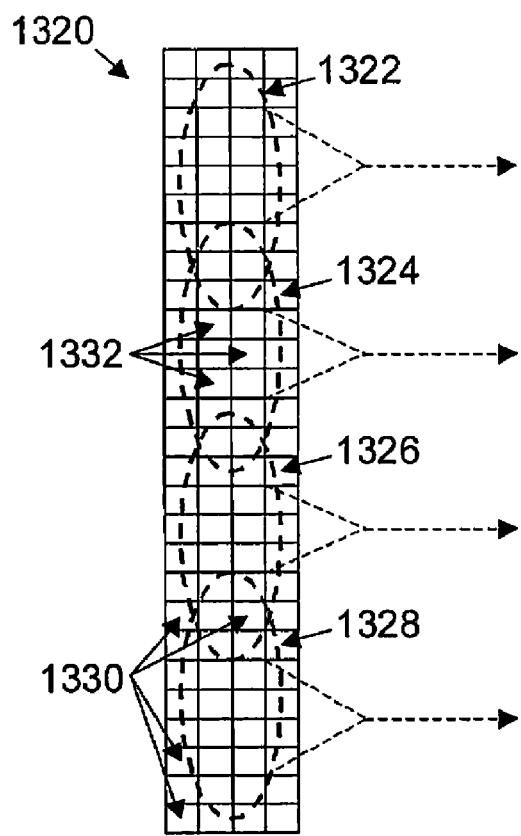
Figure 42:
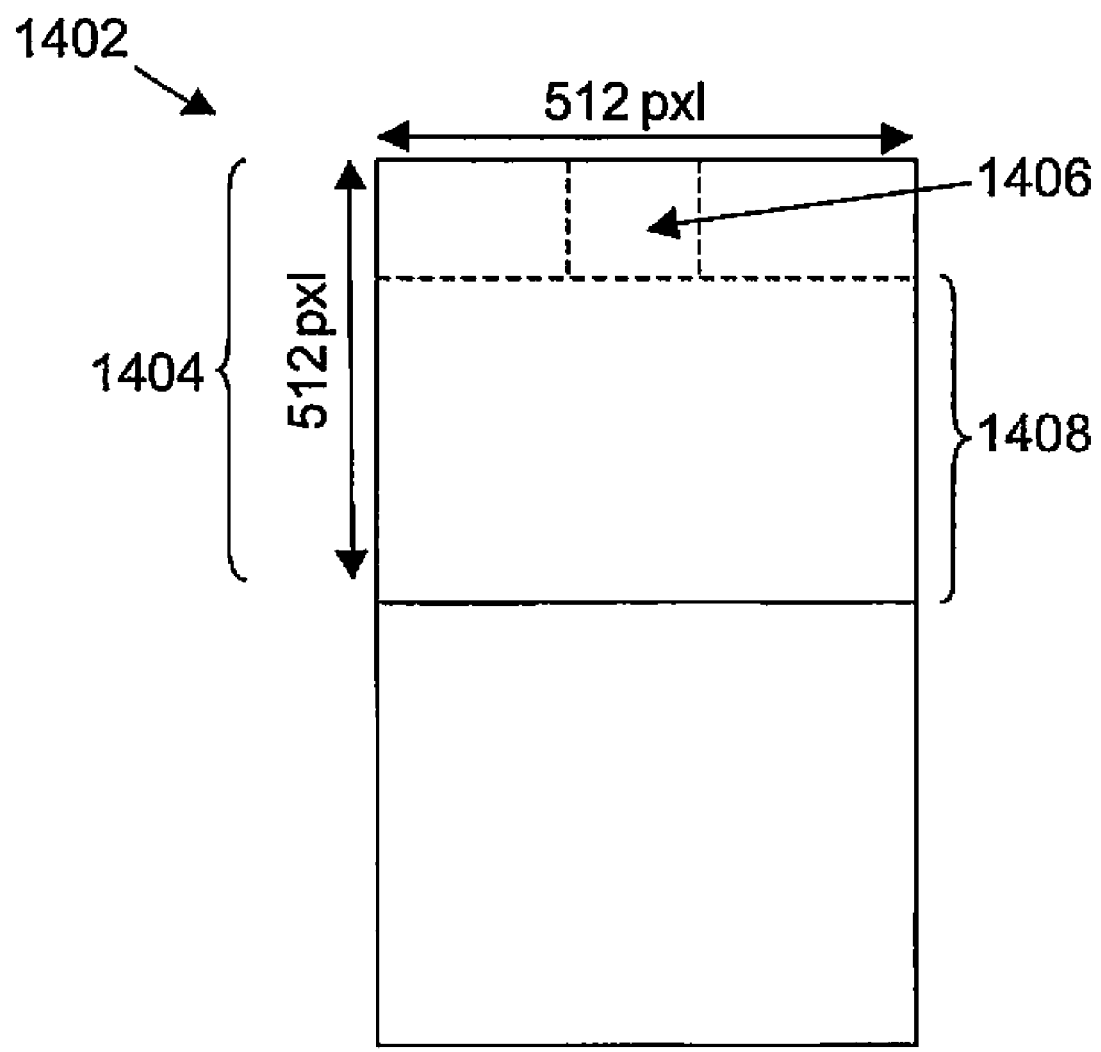
FIG. 42 schematically illustrates data management on an EMCCD detector to enhance efficiencies of the system.

A more complex implementation of this selection process, where a signal from a given source is spatially separated with incomplete separation, e.g., with substantial signal overlap, is shown in FIG. 41B. As shown, a signal is imaged upon a set of pixels 4120 in an overall detector array. As shown, the signal is subjected to spectral separation whereby signal components having different spectral characteristics are directed to different (albeit overlapping) groups of pixels on the array. This is illustrated by signal images 4122, 4124, 4126, and 4128 which show considerable overlap. In accordance with this aspect of the invention, less relevant pixels, such as those that are at the periphery of each signal component or are occupied by overlapping signals, such as pixels 4130 (shown cross hatched), are discarded prior to, or combined for processing. Meanwhile, high fidelity signals upon, e.g., pixels 4132 (shown without hatching) are subjected to further processing as relevant signals.

In accordance with the processing aspects of the invention, relevant data, e.g., from pixels 4132, from each signal, e.g., signals 4122-4128, can be binned together for each signal component and processed as shown by the dashed arrows, e.g., passed through the EM gain register, the A/D conversion, and subsequent processing by the computer. All other, lower fidelity data surrounding the signals, as well as that which is included in the signal overlap regions (e.g., pixels 4130, may be discarded or binned together for simultaneous processing, e.g., A/D conversion, inclusion in background signal calculation, etc.

By binning the lower fidelity data, e.g., that includes excessive levels of mixed signal constituents, one can effectively discard or process all of these signals simultaneously, or at least separately from the relevant pixel data. In accordance with certain aspects of the invention, the data is binned in a manner that combines each set of pixels that includes the same level of spectral overlap (or absence thereof), as shown by arrows 4134 and 4136. As with the quiet detector spaces referred to previously, data from the pixels that fall between the pixels having the highest fidelity signals may be processed separately from the high fidelity signal data. For example, it may be discarded prior to subsequent processing, or it may be binned and processed in merely a separate process operation from the high fidelity data. Alternatively, it may be combined with all other low fidelity data, to generate a background level of spectral overlap signal, or the like.

In accordance with the foregoing and other aspects of the invention, it will be appreciated that rows or columns of pixels may include rows or columns that range from a single pixel width to 2 or more, 5 or more, 10 or more, or 100 or more pixels in width, or any pixel width that falls within these ranges. The specific number of pixels that fall within a given row or column, whether it be a signal row or column or a "quiet" row or column, will depend upon the desired application, and they may be varied from system to system, or even within a given system, e.g., column and row widths in the monitoring of any given substrate may vary across the detector, e.g., one signal row may be two pixels wide while another row is 10 pixels wide. Likewise, in the same application, while a given quiet row may be 2 or 10 pixels wide, another quiet row in the same detection event may be 10 or 20 pixels wide.

Further, any of these signal data manipulation techniques may be applied dynamically, to optimize different parameters, e.g., signal to noise ratio, for each analytical operation that is being performed. In particular, one could adjust the relative spacing of the excluded rows and/or columns, the number of pixels being assigned to each signal event, or any combination of these to achieve a desired signal to noise ratio, e.g., by comparing a standard signal to a background noise. Further, this could be performed using appropriate software programming to be able to optimize for any of a number of different regions or numbers of regions or signal sources imaged onto an array.

In some cases, it may be desirable to provide a physical mask over an array detector to filter any signal derived from areas between the signal sources spaces on the detector array to filter out any noise derived from signal in adjoining signal sources/pixel areas. The physical mask may comprise a separate optical element, e.g., an opaque substrate having optical apertures disposed at regions that correspond with the imaged signals, e.g., similar to photolithographic masks used in semiconductor fabrication. Alternatively, the mask may be provided as a layer over the detector array, e.g., using light absorbing polymers or polymers containing light absorbing materials, photoresists, or the like.

As will be appreciated, noise that derives from the system itself, and that will still be present in the event that a mask is used without other adjustments, may be accounted for and dealt with in any of the methods described above. In a further aspect, one could employ detector arrays that are specifically configured, e.g., through the placement of detector elements, e.g., pixels in a CCD, to correspond to the regions upon the array where signals will be incident, and thus exclude background signal events, e.g., that would be incident on the array between relevant imaged signal events.

A modified EMCCD can be used as the detector array. In particular, conventional EMCCDs use a frame transfer process in moving data to the storage area of the CCD chip, and then use a separate EM Gain register to provide signal gain of up to 100×, 500×, 1000×, 2000× or more before the data is digitized and transferred to the processor, e.g., a connected computer. While this process is effective in the detection of low light level signals, the separate EM Gain register can be quite large, relative to the overall chip footprint, occupying a great deal of CCD chip real estate. In accordance with certain aspects, the EMCCD is configured so that the clocking voltages used for the row shift process are arranged to realize the gain during the transfer of data from the image area to the storage area, rather than post storage via an EM Gain register. In particular, as noted previously, typical frame transfer process to the storage area on the CCD chip, and subsequent transfer to the EM gain register are each carried out with an applied potential of approximately 2V. Processing the charge associated with the signal through the gain protocols in the EM gain register is then done with an applied potential of approximately 50V. By applying the 50V and implementing the gain protocol during the frame transfer process, one can obviate the need for the EM gain register.

In addition to the foregoing, and as further examples of the benefits of the invention, current EMCCD cameras operate by adding a long string of "pixels" (several hundred) and applying a very high voltage (50V or more) to move the data from one pixel to the next. 50 V is sufficient to cause a small probability of creating spurious charges—for example if one electron is being moved from one pixel to the next, there is a 1% chance that an extra electron will be created, thus doubling the apparent signal strength. Simple statistics can be used to show that a gain of 1000× can be achieved with a 1% probability per pixel and approximately 400 pixels. The drawback of this approach is that there is typically only one gain amplifying channel for the entire EMCCD chip—this means that data from every single pixel must be funneled through the same gain amplifier. In a particular exemplary EMCCD camera, the data is passed through this single gain amplifier and then digitized at a rate of 10 Megahertz, meaning a maximum frame rate of the camera is 33 Hz (512×512 pixels divided by 10 Megahertz).

In the context of the invention, however, applying a higher voltage to the frame transfer process, e.g. similar voltage level to that used in the gain amplifier of conventional EMCCDs, one could attain similar or greater amplification. Further, and with reference to an exemplary EMCCD chip having 512 rows of pixels (512×512), the frame transfer process would include 512 transfers from one pixel to the next. A voltage less than 50V, with a probability a bit less than 1%, would provide the 1000 gain that is available through a integrated gain register. As a result of negating the need for a gain register and its associated bottle neck and chip area requirements, the EMCCD according to the instant invention would be much faster, and the real estate required could be about half, which would be expected to cut the chip cost in half.

Thus, in certain aspects, signal analysis modules of the invention can process image data from a CCD, and particularly an ICCD or EMCCD, that include applying gain voltage during a frame transfer process, and CCD based detectors that are configured to carry out this process. By utilizing the frame transfer process as the gain amplification process, one significantly increases the processing speed for signal data, significantly reduces the chip real estate, and consequently the chip cost associated with a typical EMCCD camera or other such detector.

Another aspect of the signal image data processing aspects of the invention provides benefits in terms of preservation of system performance, in addition to providing advantages in efficiency of data processing. In particular, as noted above, CCD detectors, and particularly, high sensitivity CCDs, such as EMCCDs are preferred for use as detector arrays in the systems of the invention, because they can offer a combination of high gain, parallel readout and fast framerate. These attributes make such detectors particularly well suited for use in applications that are temporally monitoring operations that yield very low level optical signals, such as single molecule analyses. However, as a result of possessing these attributes, the EMCCDs may be subject to degradation of performance. In particular, in the case of EMCCDs, the EM gain register may be subject to rapid degradation when large amplitude signals are passed trough it.

In preventing such degradation, it is generally desirable to limit the amplitude of signals being processed by the EM gain register. However, even limiting such amplitudes to within manufacturer recommendations still can yield substantial degradation. Without being bound to a particular theory of operation, it is believed that a contributing factor to gain degradation is the combination of signals on the CCD chip, when a subset of pixels of the array in a region of interest on an array is read out from the chip. This operating mode can be implemented differently on different EMCCD configurations, but for at least some configurations, the pixel rows that are outside of the region of interest are combined together and then passed through the EM gain register. This can lead to substantial variation in the amplitude of the signals being passed through the register, leading to degradation. Accordingly, the present invention also provides methods for reducing or eliminating the large amplitude variation of signals being processed by the gain register.

In certain aspects, this is achieved applying the processes described elsewhere herein. In particular, the excess charge that derives from regions of the CCD that are not used to image relevant signals, e.g., those regions of the CCD that fall between or outside imaged signals from signal sources, are cleared before passing the overall signals through the gain register. In particular, a number of EMCCD configurations are available e.g., EMCCDs from E2V Technologies, Inc., that include electrical taps that may be used to bypass the gain register and send the signal output from these other regions to a separate destination, e.g., as shown by the dashed arrow in FIG. 12, panel B, but leading to a separate output from the EM gain register. These taps may be configured on a per frame basis, and may, along with the control pins, be integrated into the CCD design.

In an alternative or additional method, and as alluded to above, one may also only subject certain highly relevant array regions to subsequent processing, e.g., disregarding regions where little or no relevant signal is imaged, e.g., spaces between or surrounding relevant signal regions on the array.

By avoiding passing data from these regions through the EM Gain register, at least one source of large amplitude variations, e.g., the variation from relevant signal bearing pixels and pixels that are just communicating noise, in the signal data can be avoided. This is generally accomplished by providing for a readout of the chip on a segmented basis, e.g., pixel by pixel, or sub-region by sub-region. This is a particularly useful solution where the imaging frame rate is not required to be fast, e.g., greater than 33 Hz, allowing for the slower processing methods.

For higher framerate applications, the charge combination effect can be mitigated by reducing the number of rows that can be combined together. For example, and with reference to FIG. 39, in a 512×512 pixel EMCCD 4202, where within the image area 4204, an 80×80 sub-region 4206 is read out, over up to 432 rows of irrelevant or quiet pixels 4208 can be combined together. If these rows are combined in groups of ten, instead of as a single group, the damage effect will be reduced by a factor of 43, while maintaining a relatively high framerate, e.g., 100 Hz or greater.

Figure 43:
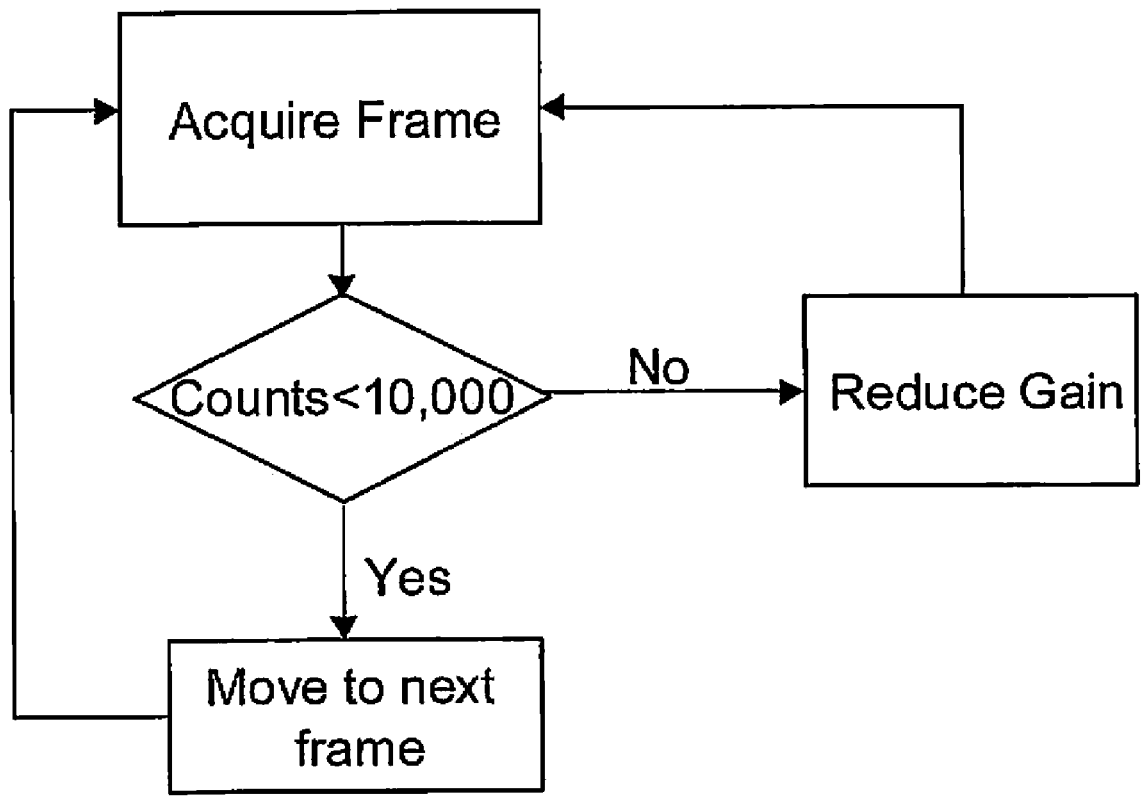
FIG. 43 provides a flowchart of data processing from CCD detector arrays to minimize effects of large signal variations.

In yet another aspect, a CCD may be programmed to adjust the EM gain, dynamically as it recognizes large signal amplitude variations. In such applications, the voltages of the EM gain register would be reduced when processing charge from outside of the region of interest on the array. Alternatively, software can be implemented to monitor the maximum signal, and reduce the EM gain automatically when that signal exceeds a proscribed level. This is schematically illustrated in the process flow chart provided in FIG. 43. This can also be extended to signal packets that come through the EM gain register. Finally, masking techniques, e.g., knife edge masks, can be employed to mask off rows on the CCD that are outside of the regions of interest that would otherwise be combined.

Relatedly, the detectors and/or systems of the invention may provide for the automatic measurement and/or calibration of the gain, by automatically determining the gain in the absence of actual signals. In particular, in many multiplying image detectors, such as EMCCDs, degradation of gain over time can create issues of signal and data quality, unless the gain is regularly measured and calibrated, so as to provide amplified signal data within a desired range. In the past, this measurement has been carried out manually, requiring significant time and effort, and introducing potential avenues for human variation into an overall process.

In accordance with this aspect of the invention, the gain is measured during a period where no signal data is incident upon the detector. Typically, this may be accomplished by automatically closing the shutter of the optical system so as to block signal data from impinging on the detector. Likewise, this could be accomplished by turning off any light sources that might provide such signals. In any event, the gain measured in the absence of signal is then used to calibrate the gain register so as to fall within a desired gain range, and/or to provide signal data that will fall within a desired amplified signal range. These processes may generally be programmed into the controlling computer, e.g., that initiates closure of the shutter, records measured gain and recalibrates gain register.

XI. User Interface

Substrate analysis systems of the invention optionally include a user interface that accepts user instructions to control the various components and corresponding functions of the systems. For example, the user interface can accept user instructions to control the substrate preparation station, gripper, substrate analysis mount, environmental control module, low vibration cooling element, and the like. In preferred embodiments, the user interface is a touch screen interface, permitting the user to control the above components and functions of the system by touching appropriate portions of a screen, e.g., a touch-sensitive LCD or other suitable screen, obviating the need for more cumbersome input devices (e.g., a keyboard or separate computer). In particularly preferred aspects, the user interface is attached the cabinet of the system and operatively coupled to one or more control modules of the system. Alternatively, remote user interfaces may also be provided that are in communication worth the overall system via a wireless network. Such user input devices may include other purposed devices, such as notepad computers, e.g., Apple iPad, or smartphones running a user interface application. Optionally, the user interface includes a component, e.g., a data port, from which the user can receive data obtained by the analysis system to a portable electronic storage medium for use at location other than the location of the substrate analysis system.

XII. Exemplary Applications

A. Sequencing by Synthesis

One example of an analytical operation in which the present invention is particularly applicable is in the determination of nucleic acid sequence information using sequence-by-synthesis processes. Briefly, sequencing-by-synthesis exploits the template-directed synthesis of nascent DNA strands, e.g., using polymerase-mediated strand extension, and monitors the addition of individual bases to that nascent strand. By identifying each added base, one can deduce the complementary sequence that is the sequence of the template nucleic acid strand. A number of "sequence-by-synthesis" strategies have been described, including pyrosequencing methods that detect the production of pyrophosphate upon the incorporation of a given base into the nascent strand using a luminescent luciferase enzyme system as the indicating event. Because the indicator system is generic for all four bases, the process requires that the polymerase/template/primer complex be interrogated with only one base at a time.

Other reported sequence-by-synthesis methods employ uniquely labeled nucleotides or nucleotide analogs such that the labels provide both an indication of incorporation of a base, as well as indicate the identity of the base (See, e.g., U.S. Pat. No. 6,787,308, incorporated herein by reference in its entirety for all purposes). Briefly, these methods employ a similar template/primer/polymerase complex, typically immobilized upon a solid support, such as a planar or other substrate, and interrogate it with nucleotides or nucleotide analogs that may include all four bases, but where each type of base bears an optically detectable label that is distinguishable from the other bases. These systems employ terminator bases, e.g., bases that, upon incorporation, prevent further strand extension by the polymerase. Once the complex is interrogated with a base or mixture of bases, the complex is washed to remove any non-incorporated bases. The washed extended complex is then analyzed using, e.g., four color fluorescent detection systems, to identify which base was incorporated in the process. Following additional processing to remove the terminating group, e.g., using photochemistry, and in many cases, the detectable label, the process is repeated to identify the next base in the sequence. In some cases, the immobilized complex is provided upon the surface as a group of substantially identical complexes, e.g., having the same primer and template sequence, such that the template mediated extension results in extension of a large number of identical molecules in a substantially identical fashion, on a step wise basis. In other strategies, complexes are immobilized in a way that allows observation of individual complexes resulting in a monitoring of the activity of individual polymerases against individual templates.

In another sequencing-by-synthesis process, one monitors the stepwise addition of differently labeled nucleotides as they are added to the nascent strand and without the use of terminator chemistries. Further, rather than through a one-base-at-a-time addition strategy, monitoring of the incorporation of bases is done in real time, e.g., without the need for any intervening wash steps, deprotection steps or separate de-labeling steps. Such processes typically rely upon optical strategies that illuminate and detect fluorescence from confined reaction volumes, such that individual complexes are observed without excessive interference from labeled bases in solution that are not being incorporated (See U.S. Pat. Nos. 6,991,726, 7,013,054, 7,052,847, 7,033,764, 7,056,661, and 7,056,676, the full disclosures of which are incorporated herein by reference in their entireties for all purposes), or upon labeling strategies that provide fluorescent signals that are indicative of the actual incorporation event, using, e.g., FRET dye pair members on a base and on a polymerase or template/primer (See U.S. Pat. Nos. 7,052,847, 7,033,764, 7,056,661, and 7,056,676, the full disclosures of which are incorporated herein by reference in their entireties for all purposes).

In accordance with the foregoing sequence-by-synthesis methods, one may optionally provide the complexes over an entire surface of a substrate, or one may selectively pattern the immobilized complexes within structurally and/or optically confined reaction regions disposed upon or within the substrate, e.g., zero mode waveguides. Patterning of complexes may be accomplished in a number of ways using selectively patternable chemical linking groups, and/or selective removal or ablation of complexes not in the desired regions. In some cases, one can employ the waveguides in selectively patterning such complexes using photoactivatable chemistries within the illumination region. Such strategies are described in detail in U.S. patent application Ser. No. 11/394,352 filed Mar. 30, 2006, the disclosure of which is incorporated herein by reference in its entirety for all purposes.

In addition to selective immobilization, and as noted above, in some cases it is desirable to immobilize the complexes such that individual complexes may be optically resolvable, e.g., distinguished from other complexes. In such cases, the complexes may be immobilized using highly dilute solutions, e.g., having low concentrations of the portion of the complex that is to be immobilized, e.g., the template sequence, the polymerase or the primer. Alternatively, the surface activation for coupling of the complex component(s) may be carried out to provide a low density active surface to which the complex will be bound. Such surfaces have been described in U.S. patent application Ser. No. 11/240,662, filed Sep. 30, 2005, which is incorporated herein by reference in its entirety for all purposes.

While described in terms of real-time nucleic acid sequencing-by-synthesis, it will be appreciated that a wide variety of real-time, fluorescence based assays may be enhanced using the systems of the invention. In particular, the systems provided herein facilitate simultaneous illumination and detection of multiple fluorophores of multiple different wavelengths in real time for a variety of experimental systems. These systems have broad applicability in a variety of biological analyses, including monitoring RNA synthesis and expression analysis, as well as monitoring ribosomal activity in translation/protein synthesis, as well as any of a variety of other analyses where it is desirable to observe the real time activity of enzymes or other biologically or otherwise relevant reactions.

B. Molecular Arrays and Other Surface Associated Assays

Another exemplary application of the invention is in the analysis of molecular arrays. Such array systems typically employ a number of immobilized binding agents that are each specific for a different binding partner. The different binding agents are immobilized in different known or readily determinable locations on a substrate. When a fluorescently labeled material is challenged against the allay, the location to which the fluorescently labeled material binds is indicative of its identity. This may be used in protein-protein interactions, e.g., antibody/antigen, receptor-ligand interactions, chemical interactions, or more commonly in nucleic acid hybridization interactions. See, U.S. Pat. Nos. 5,143,854, 5,405,783 and related patents, and GeneChip® systems from Affymetrix, Inc.

C. Cellular Observation and Analysis

In still another exemplary application, cell-based assays or analyses may be carried out by providing cells adhered to the substrate surface. As a result, one could directly monitor fluorescently labeled biological functions, e.g., the uptake of fluorescent components, the generation of fluorescent products from fluorogenic substrates, the binding of fluorescent materials to cell components, e.g., surface or other membrane coupled receptors, or the like.

D. Other Applications

It will be appreciated by those of ordinary skill that the substrates of the invention may be broadly applicable in a wider variety of applications that monitor analytical processes, including but not limited to those provided in U.S. Patent Application Nos. 61/186,645 and 61/186,661, both of which were filed Jun. 12, 2009 and are incorporated herein by reference in their entireties for all purposes. In addition, such substrates and methods may be employed in the identification of location of materials on surfaces, the interrogation of quality of a given process provided upon the surface, the photo-manipulation of surface bound materials, e.g., photo-activation, photo-conversion and/or photo-ablation. As such, while some of the most preferred applications of the present invention relate to analytical operations and particularly in the fields of chemistry, biochemistry, molecular biology and biology, the discussion of such applications in no way limits the broad applicability of the invention.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An automated high-throughput substrate analysis system, comprising:

a substrate container storage tray configured to accept a plurality of substrate containers;

a substrate preparation station configured to deliver one or more reactant to at least one reaction site on at least one substrate;

an automated gripper configured to puncture a seal on a substrate container mounted in the storage tray, and to grasp the substrate inside of the container, wherein, during operation of the system, the gripper removes the substrate from the container and delivers it to the substrate preparation station;

an optional incubation station that incubates the substrate, wherein the automated gripper moves the substrate from the substrate preparation station to the incubation station;

an analysis mount configured to accept at least one substrate from the substrate preparation station or the incubation station for analysis;

an environmental control module that controls one or more environmental parameters of the substrate preparation station, incubation station, or the analysis mount;

a machine vision system that monitors one or more of: substrate transport, substrate positioning, gripper position, gripper movement, or activity of the substrate preparation station, the incubation station, or the analysis mount;

at least one optical train configured to illuminate the substrate in the substrate mount and to receive optical signals from the substrate, the substrate holder or the optical train being adjustable relative to one another;

an autofocus module configured to monitor the quality of optical signal detection and adjust the relative positions of the substrate and one or more components of the optical train to enhance detection of optical signals from the substrate;

an output that delivers optical signal data from the optical train to an analysis module;

at least one low vibration cooling element that cools the substrate when mounted in the substrate mount, or that cools the substrate mount, or that cools the optical train, or a combination thereof; and, a user interface that accepts user instructions to control the substrate preparation station, gripper, analysis mount, environmental control module, or low vibration cooling element.

2. The system of claim 1, comprising a cabinet, the cabinet comprising an upper region and a lower region, the upper region housing the substrate container storage tray, the substrate preparation station, the automated gripper, and the analysis mount; the lower region housing the optical train; wherein, during operation of the system, the environmental control system maintains a positive cabinet pressure in at least a portion of the cabinet.

3. The system of claim 1, wherein the optical train or the mount comprises one or more leveling or vibration damping components.

4. The system of claim 1 wherein the autofocus module comprises:
an optical energy source;
an optical element that blocks a portion of a beam of optical energy emanating from the optical energy source;
an objective lens configured to focus optical energy not blocked by the optical element onto a surface of the substrate, which focused optical energy is reflected off the surface of the substrate; and,
an optical detector that detects the optical energy reflected off the surface of the substrate.

5. The system of claim 4 comprising a dichroic mirror that directs the optical energy reflected off the surface of the substrate toward the optical detector.

6. The system of claim 4 comprising a lens that optically couples the dichroic mirror and the optical detector.

7. The system of claim 1, wherein the optical train comprises one or more fluid cooling structures and the substrate analysis mount comprises or is coupled proximal to at least one heat sink or Peltier cooling structure.

8. The system of claim 1, wherein the substrate comprises one or more zero mode waveguide.

9. The system of claim 8, wherein the one or more zero mode waveguide comprises about 80,000 or more zero mode waveguides.

10. The of claim 1, having two or more beamlets of excitation radiation and comprising an alignment module that aligns the two or more beamlets of excitation radiation with the two or more reaction regions on the substrate.

11. The system of claim 10, comprising one or more micromirror disposed proximal to each of the two or more reaction regions on the substrate.

12. The system of claim 11, wherein the alignment module comprises:
an optical energy source that directs optical energy toward the substrate; and,
an optical energy detector configured to detect optical energy reflected from the one or more micromirror disposed proximal to each of the two or more reaction regions of the substrate.

13. The system of claim 12, comprising a lens through which optical energy reflected from the one or more micromirror passes prior to reaching the optical energy detector.

14. The system of claim 12, wherein the optical energy detector is configured to detect the positions of the two or more beamlets of excitation radiation on the substrate.

15. The system of claim 14, wherein the alignment module compares the position on the detector of the detected optical energy reflected from the one or more micromirror and the positions of the two or more beamlets of excitation radiation on the substrate to align the two or more beamlets with the two or more reaction regions.

* * * * *